US007811598B2

(12) United States Patent
Carozzi et al.

(10) Patent No.: US 7,811,598 B2
(45) Date of Patent: Oct. 12, 2010

(54) AXMI-028 AND AXMI-029, A FAMILY OF NOVEL DELTA-ENDOTOXIN GENES AND METHODS FOR THEIR USE

(75) Inventors: Nadine Carozzi, Raleigh, NC (US); Michael G. Koziel, Raleigh, NC (US); Tracy Hargiss, Kernersville, NC (US); Nicholas B. Duck, Apex, NC (US)

(73) Assignee: Athenix Corp., Research Triangle Park, NC (US)

( * ) Notice: Subject to any disclaimer, the term of this patent is extended or adjusted under 35 U.S.C. 154(b) by 181 days.

(21) Appl. No.: 12/166,253

(22) Filed: Jul. 1, 2008

(65) Prior Publication Data

US 2009/0054335 A1 Feb. 26, 2009

Related U.S. Application Data

(62) Division of application No. 11/416,261, filed on May 2, 2006, now Pat. No. 7,622,572.

(60) Provisional application No. 60/676,809, filed on May 2, 2005.

(51) Int. Cl.
*A01N 25/00* (2006.01)
*A61K 38/16* (2006.01)
*C12P 21/02* (2006.01)
(52) U.S. Cl. .................. 424/405; 514/12; 435/71.3; 435/69.1
(58) Field of Classification Search .................. 424/405; 514/12; 435/71.3, 69.1
See application file for complete search history.

(56) References Cited

U.S. PATENT DOCUMENTS

2007/0044178 A1 2/2007 Carozzi et al.

FOREIGN PATENT DOCUMENTS

EP 0 382 990 A1 8/1990

(Continued)

OTHER PUBLICATIONS

Result 4, alignment of instant SEQ ID No. 4 with SEQ ID No. 4 of Payne et al., US 5,286,486, CryVIIA(b) delta endotoxin, Uniprot record No. Q45708, Uniprot database search performed on Mar. 31, 2010.*

(Continued)

*Primary Examiner*—Karen Cochrane Carlson
*Assistant Examiner*—Rosane Kosson
(74) *Attorney, Agent, or Firm*—Destiny M. Davenport

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2, 4, 15, 17, or 19, or the nucleotide sequence set forth in SEQ ID NO:1, 3, 14, 16, or 18, as well as variants and fragments thereof.

8 Claims, 6 Drawing Sheets

FOREIGN PATENT DOCUMENTS

| | | |
|---|---|---|
| WO | WO 93/08693 A1 | 5/1993 |
| WO | WO 2004/074462 A2 | 9/2004 |

OTHER PUBLICATIONS

Guo, H.H., et al., "Protein Tolerance to Random Amino Acid Change," *PNAS*, Jun. 22, 2004, pp. 9205-9210, vol. 101, No. 25.

Result 1, Geneseq Database Search, Alignment of SEQ ID No. 1 with SEQ ID No. 3 of Mycogen Corp. WO 93/08693 A1, Searched on Jun. 10, 2007.

Pre-OG Notice, "Examination of Patent Applications Containing Nucleotide Sequences," (http://www.uspto.gov/seb/offices/pac/dapp/opla/preognotice/sequence02212007.pdf), printed on Jun. 13, 2007.

NCBI Database Report for Accession No. Q03749, Mar. 21, 2006 (referenced in "Novel bacillus thuringiensis insecticidal crystal protein with a silent activity against coleopteran larvae," Appl. Environ. Microbiol. 58(8), 2536-2542.

NCBI Database Report for Accession No. Q45707, Mar. 21, 2006 (referenced in US Patent No. 5,286,486 and characterized by the database as being a "Pesticidal crystal protein cry7Ab").

NCBI Database Report for Accession No. Q45708, Mar. 21, 2006 (referenced in US Patent No. 5,286,486 and characterized by the database as being a "Pesticidal crystal protein cry7Ab").

\* cited by examiner

Fig. 1A

```
axmi029 : KVDQVSILVDCVSGELYPMEKREFQNLIKYAKRLSYSRNLLLDPTFDSIMSSDENGWYGSNGIAICSGNIVFKGNYLIFSGTMDEQYPTYLYQKID :  730
axmi028 : KVDQVSILVDCVSGELYPMEKREELSLVKYAKRLSYSRNLLLDPTFDSIMSPEMGWYGSNGIAICSGNIVFKGNYLIFSGTMDEQYPTYLYQKID :  759
          KVDQVSILVDCVSGELYPMEKREL L6KYAKRLSYSRNLLLDPTFDSIMS  EMGWYGSNGIAICSGNIVFKGNYLIFSGTMDEQYPTYLYQKID axmi029 : ESKLKEYTRYKLRGFIESSQDIEAYVIRYDAKHQTMDVSNNLFSDITPVMACGFPMRCAALPYLDENPRLECSSIQDGILSDSHSFSLHIDTGSID :  826
axmi028 : ETKIKEYMNKLRGFIESSQDIEAYVIRYDAKHQTMDVSNNLFSDITPVMACGFPMRCAALPYLDENPRLECSSIQDGILSDSHSFSLHIDTGSID :  855
          E3KLKEYTRYKLRGFIESSQDIEAYVIRYDAKHQTMDVSNNLFSDITPVMACGFPMRCAALPYLDENPRLECSSIQDGILSDSHSFSLHIDTGSID axmi029 : FMENVGIQWLFKISTLEGYARPGMLEVIEDGPVIGEALARVKRQETKQRMKLTQLRETQAIYTRAKQAIDMLFTMDQDSHLKICTFALIVAARK  :  922
axmi028 : FMENVGIQWLFKISTPEGYARPGMLEVIEDGPVIQELMEJLQQAFQLYDWFANVVRNGRFQSGTSDMIVTSDVRNQDEMGMNVLVLSMDAQVLQCMTLYQDRGYIL :  951
          FMENVGIQWLFKIST EGYA4FGNLEVIEDGPVIGEALARVKR QETKQRMKLTQLRETQAIYTRAKQAIDNLFTN QDSHLKIG TFA IVAARK axmi029 : IVQSIREAVMSDLSIVPGVNYPIFTELMERVQQAFQLYDWFANVVRNGRFQSGTSDMIVTSDVKQDENGMNVLVLSMDAQVLQCMTLYQDRGYIL : 1018
axmi028 : IVQSIREAVMSDLSIVPGVNYPITELNERGQQAFQLYDWFANVVRNGRFQSGTSDMIVTSDVRQDEMGMNVLVLSMDAQVLQCMTLYQDRGYIL : 1047
          IVQSIREAVMSDLSIVPGVNYPI TELNER6QQAFQLYDWFANVVRNGRFQSGTSDV4VQEENGMNVLVLSMDAQVLQCMTLYQDRGYIL axmi029 : RVTARKEGLGEGYVTITDEEGMTDQLRFGGCEEIDASMSFWSTGYWTKELEFPDTEKVRIEIGETEGFQVSWELFLMEDLC- : 1102
axmi028 : RVTARKEGLGEGYVTITDEEGMTDQLRFGGCEEIDASMSFWSTGYWTKELEFPDTEKVRIEIGETEGFQVSWELFLMEDLC  : 1131
          RVTARKEGLGEGYVTITDEEGMTDQLRFGGCEEIDASMSFWSTGYGTKELEFPDTEKVRIEIGETEG FQV SWELFLMEDLC
```

AXMI-028 AND AXMI-029, A FAMILY OF NOVEL DELTA-ENDOTOXIN GENES AND METHODS FOR THEIR USE

CROSS REFERENCE TO RELATED APPLICATION

This application is a divisional of U.S. patent application Ser. No. 11/416,261, filed May 2, 2006, now U.S. Pat. No. 7,622,572, issued on Nov. 24, 2009, which claims the benefit of U.S. Provisional Application Ser. No. 60/676,809, filed May 2, 2005, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "345431_SequenceListing.txt", created on Jun. 19, 2008, and having a size of 163 KB, and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring pesticide resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in SEQ ID NO:2, 4, 15, 17, or 19, a nucleotide sequence set forth in SEQ ID NO:1, 3, 14, 16, or 18, or the delta-endotoxin nucleotide sequence deposited in a bacterial host as Accession No. NRRL B-30807 or NRRL B-30806, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran or coleopteran pest. Methods and kits for detecting the nucleic acids and polypeptides of the invention in a sample are also included.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DESCRIPTION OF FIGURES

Figure 1A:
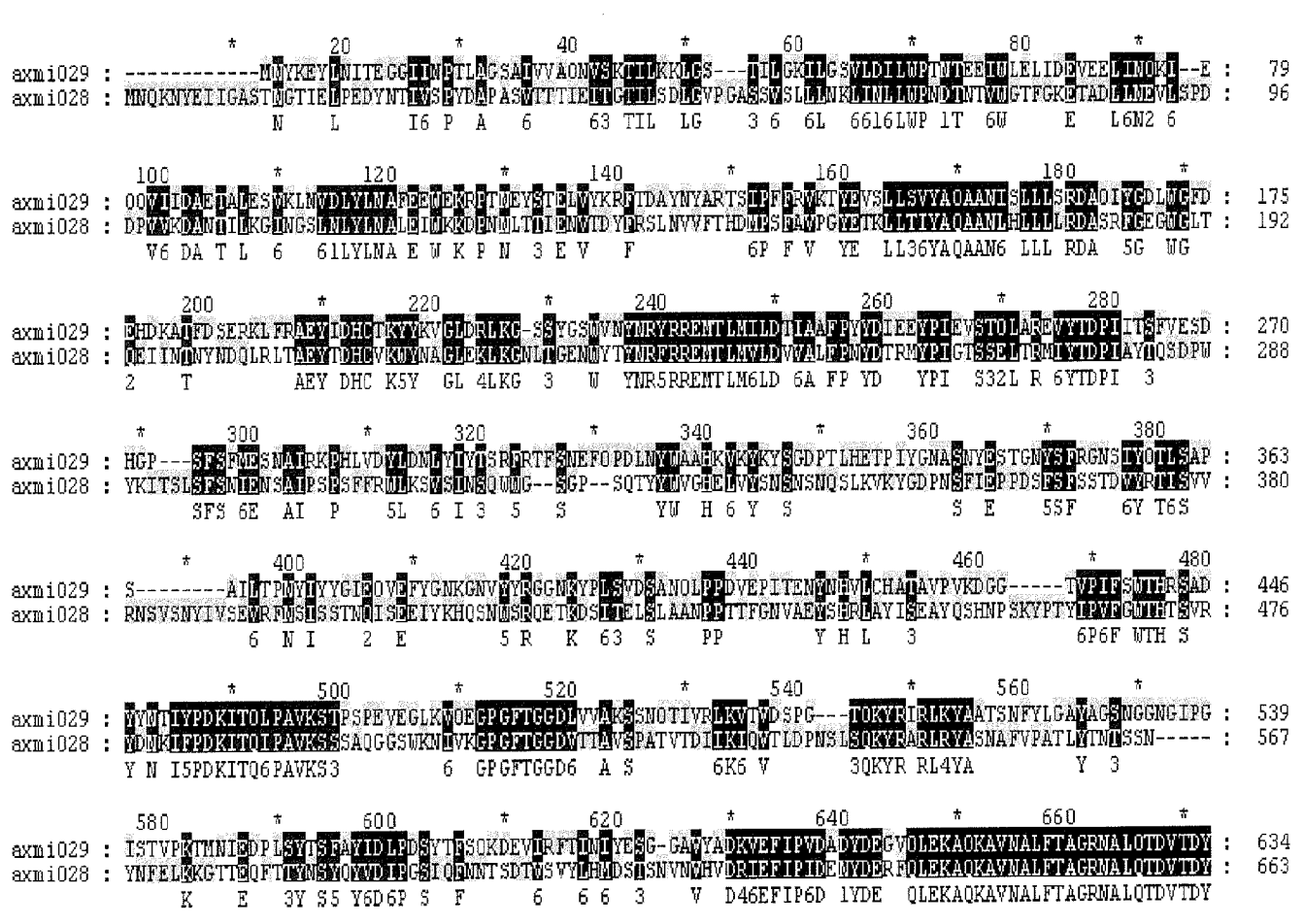

FIG. 1 shows an alignment of AXMI-028 (SEQ ID NO:2) and AXMI-029 (SEQ ID NO:4). Their C-terminal domains shows an amino acid identity of 96% while the predicted toxic N-terminus shows only 30% identity. The alignment shows the most highly conserved amino acid residues highlighted in black, and highly conserved amino acid residues highlighted in gray.

FIG. 2 shows an alignment of the artificially truncated portion of AXMI-028 with cry7Aa (SEQ ID NO:7), cry7Ab (SEQ ID NO:11), cry8Aa (SEQ ID NO:8), cry8Ba (SEQ ID NO:10), cry8Ca (SEQ ID NO:12), cry1Ba (SEQ ID NO:13) and cry1Ca (SEQ ID NO:9). All of the toxins have C-terminal non-toxic domains, and therefore were artificially truncated to represent only the active domains. The alignment shows the most highly conserved amino acid residues highlighted in black and highly conserved amino acid residues highlighted in gray. Conserved group 1 in AXMI-028 is found from about amino acid residue 160 to about 189 of SEQ ID NO:2. Conserved group 2 is found from about amino acid residue 234 to about 278 of SEQ ID NO:2. Conserved group 3 is found from about amino acid residue 468 to about 517 of SEQ ID NO:2. Conserved group 4 is found from about amino acid residue 542 to about 553 of SEQ ID NO:2. Conserved group 5 is found from about amino acid residue 618 to about 627 of SEQ ID NO:2.

FIG. 3 shows an alignment of the naturally truncated protein of AXMI-029 with the artificially truncated proteins of cry7Aa (SEQ ID NO:7), cry7Ab (SEQ ID NO:11), cry3Bb (SEQ ID NO:6), cry3Aa (SEQ ID NO:5), cry8Aa (SEQ ID NO:8), cry8Ba (SEQ ID NO:10) and cry8Ca (SEQ ID NO:12). The alignment shows the most highly conserved amino acid residues highlighted in black, and highly conserved amino acid residues highlighted in gray. Conserved group 1 in AXMI-029 is found from about amino acid residue 143 to about 172 of SEQ ID NO:4. Conserved group 2 is found from about amino acid residue 216 to about 270 of SEQ ID NO:4. Conserved group 3 is found from about amino acid residue 438 to about 487 of SEQ ID NO:4. Conserved group 4 is found from about amino acid residue 509 to about 520 of SEQ ID NO:4. Conserved group 5 is found from about amino acid residue 589 to about 598 of SEQ ID NO:4.

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran or coleopteran pest populations and for producing compositions with pesticidal activity.

Plasmids containing the herbicide resistance nucleotide sequences of the invention were deposited in the permanent collection of the Agricultural Research Service Culture Collection, Northern Regional Research Laboratory (NRRL), 1815 North University Street, Peoria, Ill. 61604, United States of America, on Jan. 13, 2005, and assigned Accession Nos. NRRL B-30807 (for AXMI-028) and NRRL B-30806 (for AXMI-029). These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

By "delta-endotoxin" is intended a toxin from *Bacillus thuringiensis* that has toxic activity against one or more pests, including, but not limited to, members of the Lepidoptera, Diptera, and Coleoptera orders, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www-.biols.susx.ac.uk/Home/Neil_Crickmore/Bt/index.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

Isolated Nucleic Acid Molecules, and Variants and Fragments Thereof

One aspect of the invention pertains to isolated nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 3, 14, 16, or 18, the delta endotoxin nucleotide sequences deposited in bacterial hosts as Accession Nos. NRRL B-30807 and NRRL B-30806, and variants, fragments, and complements thereof (for example, SEQ ID NOS:14, 16, and 18). By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:2, 4, 15, 17, or 19.

Nucleic acid molecules that are fragments of these delta-endotoxin encoding nucleotide sequences are also encompassed by the present invention (for example, SEQ ID NOS: 14 and 16). By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein (for example, 3393 nucleotides for SEQ ID NO:1 and 3306 nucleotides for SEQ ID NO:3) depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, 80%, 90%, 95% or higher of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention (for example, 1131 amino acids for SEQ ID NO:2 and 1102 amino acids for SEQ ID NO:4).

Preferred delta-endotoxin proteins of the present invention are encoded by a nucleotide sequence sufficiently identical to the nucleotide sequence of SEQ ID NO:1, 3, 14, 16, or 18. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules (for example, SEQ ID NO:18). "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignments of FIGS. 2 and 3. Examples of residues that are conserved but that may allow conservative amino acid substitutions and still retain activity include, for example, residues that have only conservative substitutions between all proteins contained in the alignments of FIGS. 2 and 3. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.)

and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:2, 4, 15, 17, or 19. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:2 or 4, and that exhibit pesticidal activity (for example, SEQ ID NOS:15 and 17). A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 4, 15, 17, or 19. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, or 1100 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2 or 4 (for example, SEQ ID NO:19). Variants also include polypeptides encoded by a nucleic acid molecule that hybridizes to the nucleic acid molecule of SEQ ID NO:1, 3, 14, 16, or 18, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743, 477, all of which are herein incorporated by reference in their entirety.

Bacterial genes, such as the axmi-028 and axmi-029 genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions. Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997)

*Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence (for example, SEQ ID NO:18). Often, such constructs will also contain a 3' untranslated region. Such constructs may contain a "signal sequence" or "leader sequence" (i.e., SEQ ID NO:20) to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence (i.e., SEQ ID NO:21) sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene).

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and *Diptera*.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrimidae. Superfamily Hydrophiloidea includes the family Hydrophilidae. Superfamily Staphylinoidea includes the families Silphidae and Staphylimidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The following examples are offered by way of illustration and not by way of limitation.

EXPERIMENTAL

Example 1

Extraction of Plasmid DNA

A pure culture of strain ATX15723 was grown in large quantities of rich media. The culture was spun to harvest the cell pellet. The cell pellet was then prepared by treatment with SDS by methods known in the art, resulting in breakage of the cell wall and release of DNA. Proteins and large genomic DNA were then precipitated by a high salt concentration. The plasmid DNA was then precipitated by standard ethanol precipitation. The plasmid DNA was separated from any remaining chromosomal DNA by high-speed centrifugation through a cesium chloride gradient. The DNA was visualized in the gradient by UV light and the band of lower density (i.e. the lower band) was extracted using a syringe. This band contained the plasmid DNA from Strain ATX15723. The quality of the DNA was checked by visualization on an agarose gel.

Example 2

Cloning of Genes

The purified plasmid DNA was sheared into 5-10 kb sized fragments and the 5' and 3' single stranded overhangs repaired using T4 DNA polymerase and Klenow fragment in the presence of all four dNTPs. Phosphates were then attached to the 5' ends by treatment with T4 polynucleotide kinase. The repaired DNA fragments were then ligated overnight into a standard high copy vector (i.e. pBluescript SK+), suitably prepared to accept the inserts as known in the art (for example by digestion with a restriction enzyme producing blunt ends).

The quality of the library was analyzed by digesting a subset of clones with a restriction enzyme known to have a cleavage site flanking the cloning site. A high percentage of clones were determined to contain inserts, with an average insert size of 5-6 kb.

Example 3

High Throughput Sequencing of Library Plates

Once the shotgun library quality was checked and confirmed, colonies were grown in a rich broth in 2 ml 96-well blocks overnight at 37° C. at a shaking speed of 350 rpm. The blocks were spun to harvest the cells to the bottom of the block. The blocks were then prepared by standard alkaline lysis prep in a high throughput format.

The end sequences of clones from this library were then determined for a large number of clones from each block in the following way: The DNA sequence of each clone chosen for analysis was determined using the fluorescent dye terminator sequencing technique (Applied Biosystems) and standard primers flanking each side of the cloning site. Once the reactions had been carried out in the thermocycler, the DNA was precipitated using standard ethanol precipitation. The DNA was resuspended in water and loaded onto a capillary sequencing machine. Each library plate of DNA was sequenced from either end of the cloning site, yielding two reads per plate over each insert.

Example 4

Assembly and Screening of Sequencing Data

DNA sequences obtained were compiled into an assembly project and aligned together to form contigs. This can be done efficiently using a computer program, such as Vector NTI, or alternatively by using the Phred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further. Among the sequences obtained, clones pAX028 and pAX029 contained DNA identified as having homology to known endotoxin genes. Therefore, clones pAX028 and pAX029 were selected for further sequencing.

Example 5

Sequencing of pAX028 and pAX029

Primers were designed to anneal to the clones of interest (pAX028 and pAX029) in a manner such that DNA sequences generated from such primers will overlap existing DNA sequence of the clone(s). This process, known as "oligo walking," is well known in the art. This process was utilized to determine the entire DNA sequence of the region exhibiting homology to a known endotoxin gene. In the case of pAX028 and pAX029, this process was used to determine the DNA sequence of the entire clones, resulting in a single nucleotide sequence for each. The completed DNA sequence was then placed back into the original large assembly for further validation. This allowed incorporation of more DNA sequence reads into the contig, resulting in multiple reads of coverage over the entire region.

Analysis of the DNA sequence of each clone by methods known in the art identified an open reading frame on each insert with homology to known delta endotoxin genes. The open reading frames found in pAX028 and pAX029 were designated as AXMI-028 and AXMI-029, respectively. The DNA sequence of axmi-028 is provided in SEQ ID NO:1, and the amino acid sequence of the predicted protein is provided in SEQ ID NO:2. The DNA sequence of axmi-029 is provided in SEQ ID NO:3 and its predicted protein sequence is provided in SEQ ID NO:4.

Example 6

Homology Between AXMI-028 and AXMI-029

The novel ORFs found in strain ATX15723 which showed homology to known delta-endotoxin genes also showed high homology to each other, with most changes occurring in the N-terminal domain. When the full length proteins of the genes were aligned with one another, the amino acid identity was 59% across the entire gene. However, there was only 30% amino acid identity between the toxic N-termini. Most of the conserved amino acids were found in the C-terminal domain, which were 96% identical.

Example 7

Homology of AXMI-028 and AXMI-029 to Known Endotoxin Genes

A search of DNA and protein databases with the DNA sequences and amino acid sequences of AXMI-028 and AXMI-029 revealed that they are homologous to known delta-endotoxin proteins.

Figure 2A:
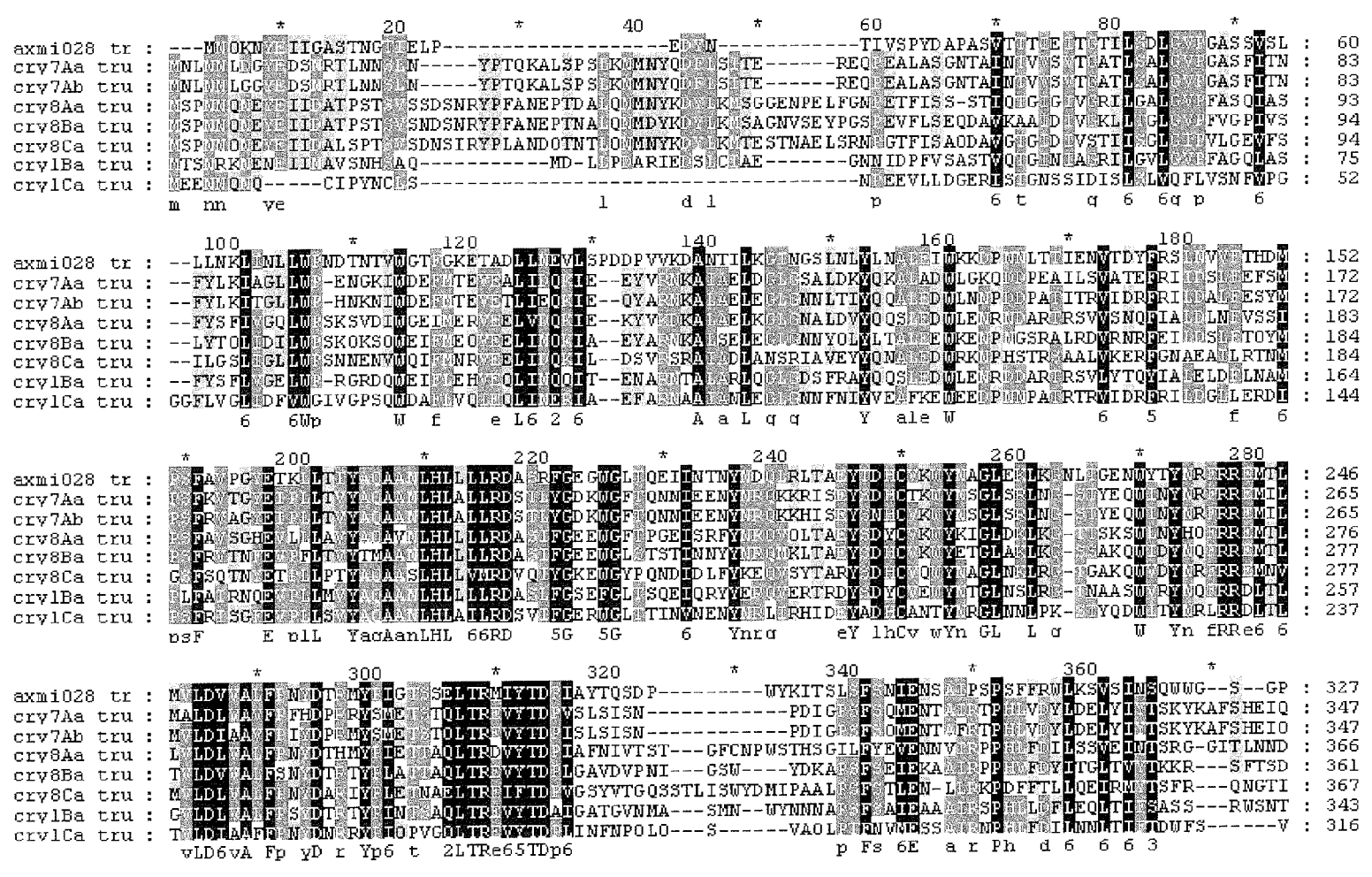
Figure 2B:
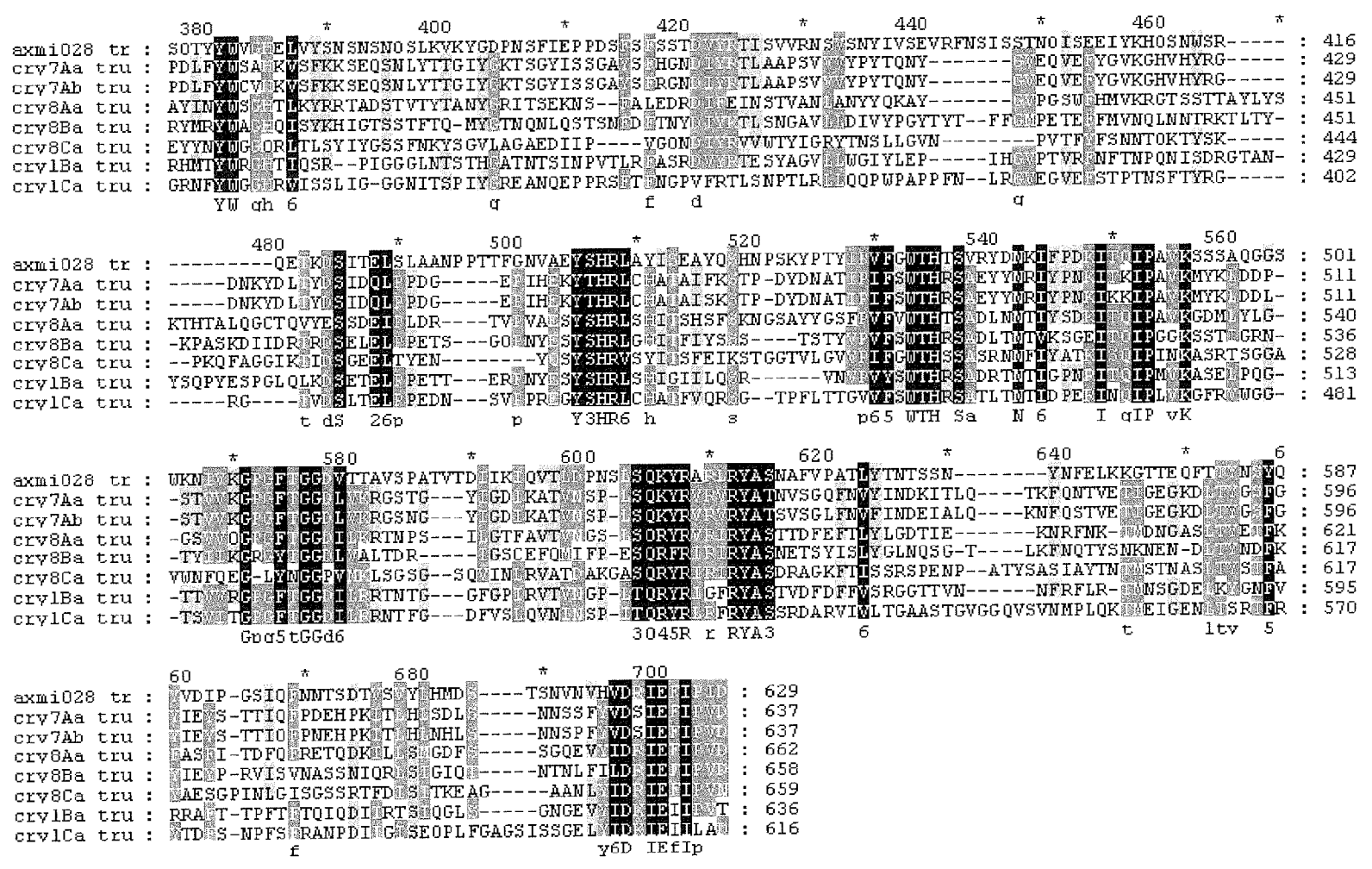

FIG. 2 shows an alignment of AXMI-028 with several endotoxins. Blast searches identified cry7Ab as having the strongest block of homology to AXMI-028. Aligning the AXMI-028 protein (SEQ ID NO:2) to a large set of endotoxin proteins confirmed that cry7Aa (SEQ ID NO:7) and cry7Ab (SEQ ID NO:11) are most homologous to AXMI-028 protein (54% amino acid identity; see Table 1). The higher homology of AXMI-028 to cry7Ab as compared to other endotoxins is due in large part to the high homology of the non-toxic C-terminal domain of AXMI-028 to cry7Aa and cry7Ab toxins. The second column of Table 1 shows the amino acid identity to the untrimmed, full-length proteins. The endotoxins cry7Ab (SEQ ID NO:11) and cry8Aa (SEQ ID NO:8) show the highest homology to AXMI-028 within the N-terminal toxic domain (33% amino acid identity; see Table 1). The third column reflects the true identity of the active portion of the protein by aligning only the toxic domains.

TABLE 1

Amino Acid Identity of AXMI-028 with Exemplary Endotoxin Classes

| Endotoxin | Percent Amino Acid Identity to AXMI-028 | Percent Amino Acid Identity of truncated Toxins to AXMI-028 |
| --- | --- | --- |
| cry7Aa | 54% | 32% |
| cry7Ab | 54% | 33% |
| cry8Aa | 38% | 33% |
| cry8Ba | 35% | 32% |
| cry8Ca | 34% | 29% |
| cry1Ba | 35% | 31% |
| cry1Ca | 34% | 29% |

Figure 3A:
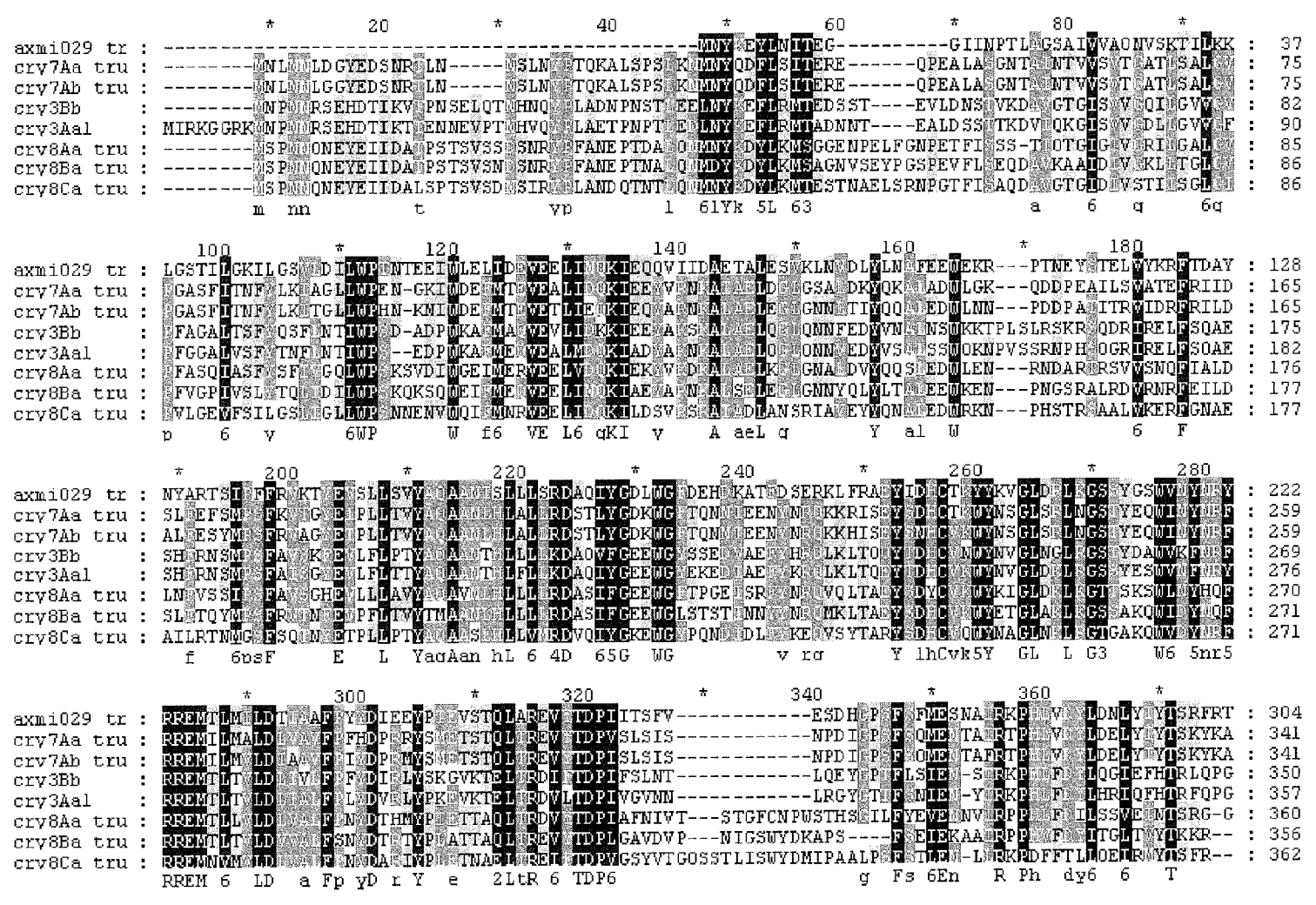
Figure 3B:
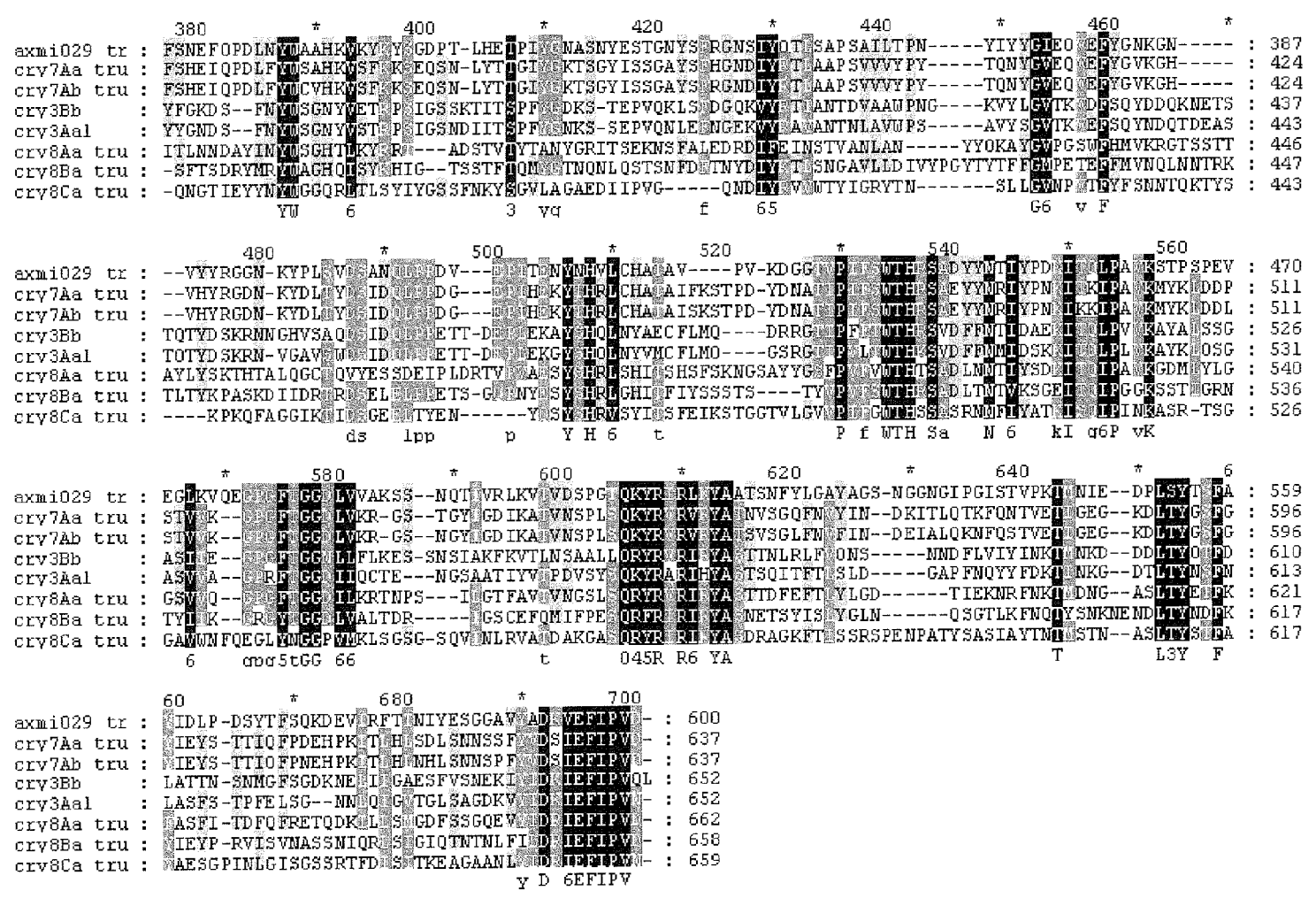

FIG. 3 shows an alignment of AXMI-029 with several endotoxins. Blast searches identified cry7Aa as having the strongest block of homology to AXMI-029. Alignment of AMXI-029 protein (SEQ ID NO:4) to a large set of endotoxin proteins identified cry7Aa (SEQ ID NO:7) as the most homologous endotoxin (61% amino acid identity; see Table 2). Similarly, the cry7Ab amino acid sequence (SEQ ID NO:11) has 61% identity to AXMI-029. The higher homology of AXMI-029 to cry7Ab compared to other endotoxins is due in large part to the high homology of the non-toxic C-terminal domain of AXMI-029 to the C-terminal domain of the cry7Aa and cry7Ab toxins. The second column of Table 2 shows the amino acid identity to the untrimmed, full-length proteins. The endotoxin with highest homology through the N-terminal active portion of the gene is cry7Ab. The amino acid identity of the truncated cry7Ab to the truncated AXMI-029 is 43% (see Table 2). The third column reflects the true identity of the active portion of the protein by aligning only the toxic domains.

TABLE 2

Amino Acid Identity of AXMI-029 with Exemplary Endotoxin Classes

| Endotoxin | Percent Amino Acid Identity to AXMI-029 | Percent Amino Acid Identity of truncated Toxins to AXMI-029 |
| --- | --- | --- |
| cry7Aa | 61% | 42% |
| cry7Ab | 61% | 43% |
| cry3Bb | 16% | 31% |
| cry3Aa | 16% | 31% |
| cry8Aa | 36% | 29% |
| cry8Ba | 35% | 31% |
| cry8Ca | 35% | 27% |

A search of the PFAM database identified AXMI-028 as having homology to a delta endotoxin. An Endotoxin_N domain (PFAM Accession No. PF03945) is found between amino acid residues 36 and 262 of the protein (SEQ ID NO:2). An Endotoxin_M domain (PFAM Accession No. PF00555) is found between amino acid residues 267 and 476 of the protein (SEQ ID NO:2). An Endotoxin_C domain (PFAM Accession No. PF03944) is found between amino acid residues 486 and 629 of the protein (SEQ ID NO:2).

This family contains insecticidal toxins produced by *Bacillus* species of bacteria. The N terminus of the crystallized protein is cleaved after insect ingestion, resulting in an activated protein. The C terminal extension is cleaved in some protein members. This activated region of the delta endotoxin is composed of three structural domains. The N-terminal helical domain is involved in membrane insertion and pore formation. The second and third domains (M and C) are involved in receptor binding.

Example 8

Insecticidal Activity of AXMI-028 and AXMI-029 on Western Corn Rootworm

AXMI-028 and AXMI-029 were tested for activity against western corn rootworm (WCR) by bioassay. *E. coli* clones pAX971 and pAX972 containing axmi-028 and axmi-029, respectively, were grown for 3 days as a liquid culture and tested as a whole culture of cells and media. A 3 day culture of *E. coli* cells containing the vector only was used as a negative control. The culture was tested as a surface contamination on artificial diet, and assays were reviewed at five days for growth inhibition compared to the control. In three independent tests, both cultures resulted in stunting of WCRW larvae, whereas the negative controls were unaffected.

TABLE 3

| Clone | Gene | Stunting of WCRW |
| --- | --- | --- |
| pAX971 | AXMI-028 | ++ |
| pAX972 | AXMI-029 | ++ |
| Vector only | Negative Control | − |

Example 9

Insecticidal Activity of AXI-028 and AXMI-029 on Southern Corn Rootworm (SCRW)

The AXMI-028 and AXMI-029 were tested for activity against southern corn rootworm (SCRW) by bioassay. *E. coli* clones pAX971 and pAX972 containing AXMI-028 and AXMI-029 respectively were grown for 3 days in liquid culture and tested as a whole culture of cells and media. A 3 day culture of *E. coli* cells containing the vector only was used as a negative control. The culture was tested as a surface contamination on artificial diet, and assays were reviewed at five days for growth inhibition compared to the control. In three independent tests, both cultures resulted in stunting of SCRW larvae, whereas the negative controls were unaffected.

TABLE 4

| Clone | Gene | Stunting of SCRW |
| --- | --- | --- |
| pAX971 | AXMI-028 | ++ |
| pAX972 | AXMI-029 | ++ |
| Vector only | Negative Control | – |

Example 10

Expression of AXMI-028 and AXMI-029 in *Bacillus*

The insecticidal genes AXMI-028 and AXMI-029 are amplified by PCR from pAX028 and pAX029, respectively. The PCR products are then cloned into the *Bacillus* expression vector pAX916 by methods well known in the art. The resulting *Bacillus* strains, containing the vector with either AXMI-028 or AXMI-029 are cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared, and AXMI-028 and AXMI-029 proteins are tested for insecticidal activity in bioassays against important insect pests.

Example 11

Additional Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

Example 12

Vectoring of axmi-028 and axmi-029 for Plant Expression

The coding regions of axmi-028 and axmi-029 are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic axmi-028 and axmi-029 sequences are generated, for example synaxmi-028 (SEQ ID NO:14) and synaxmi-029 (SEQ ID NO:16). These synthetic sequences have altered nucleotide sequence relative to the axmi-028 and axmi-029 sequences, and encode proteins that are collinear with the original AXMI protein, but lack the C-terminal "crystal domain" present in both AXMI-028 and AXMI-029. The synaxmi-028 gene sequence encodes SYNAXMI-028 protein (SEQ ID NO:15), which comprises the first 630 amino acids of the AXMI-028 protein. The synaxmi-029 gene encodes the SYNAXMI-029 protein (SEQ ID NO:17), which comprises the first 700 amino acids of the AXMI-029 protein.

In another aspect of the invention, modified versions of the synaxmi-028 and synaxmi-029 genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENEBANK® ID GI: 14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (ie the "KDEL" motif) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, the synaxmi-029ER gene (SEQ ID NO:18) encodes a fusion protein that contains the N-terminal thirty one amino acids of the acid phosphatase gene from the White Lupin *Lupinus albus* (Genebank ID GI: 14276838, Miller et al., 2001, supra) fused to the N-terminus of AXMI-029, as well as the KDEL sequence at the C-terminus. Thus, the resulting protein AXMI-029ER (SEQ ID NO: 19), is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vec-

Example 13

Transformation of axmi-028 into Plant Cells by Agrobacterium-Mediated Transformation pAX1849 contains the synaxmi-28 gene (SEQ ID NO:14), a TripPro5 promoter for plant expression (U.S. patent application Ser. No. 11/377,318, filed Mar. 16, 2006), a transcriptional termination region, and a selectable marker in a vector capable of transfer to plants by Agrobacterium-mediated transformation methods. synaxmi-028 (SEQ ID NO:15) is a synthetic gene that results in expression of the AXMI-028 protein.

Ears were collected 8-12 days after pollination. Embryos were isolated from the ears, and those embryos 0.8-1.5 mm in size used in transformation. Embryos were plated scutellum side-up on a suitable incubation medium, and incubated overnight at 25° C. in the dark. However, it is not necessary per se to incubate the embryos overnight. Embryos were contacted with an Agrobacterium strain pAG1849 containing the pAX1849 vector for about 5-10 min, and then plated onto co-cultivation media for about 3 days (25° C. in the dark). After co-cultivation, explants were transferred to recovery period media for about five days (at 25° C. in the dark). Explants were incubated in selection media for up to eight weeks, and the resulting callus was transferred to embryo maturation media, until the formation of mature somatic embryos was observed. The resulting mature somatic embryos were placed under low light, and the process of regeneration was initiated as known in the art. The resulting shoots were allowed to root on rooting media, and the resulting plants transferred to nursery pots and propagated as transgenic plants.

In this manner independent events containing axmi-028 under the control of a plant promoter were isolated, and the presence of axmi-028 confirmed by PCR. Expression of AXMI-028 was confirmed by Western blot analysis.

Example 14

Soil infestation of AXMI-028 Plants with Western Corn Rootworm

Transgenic plants containing axmi-028 under the control of a plant promoter were tested for resistance to infestation by Western corn rootworm (WCRW). Plantlets were transplanted from tissue culture media to root trainer (clamshell) pots known in the art to be useful for growth of plantlets in soil. Plants were grown for about 2 weeks in a greeenhouse. AXMI-028 positive plants, as well as untransformed controls were infested with approximately 1,000 WCRW eggs. WCRW eggs were preincubated such that eggs were at the point of hatching when infested onto the plants. Plants were held for about four weeks, or until until controls exhibited obvious damage due to the rootworms. At this stage, plants were pulled from pots, roots were washed, and damage evaluated. Several independent AXMI-028 events exhibited reduced damage from WCRW infestation relative to non-transformed control plants.

Example 15

Transformation of Maize Cells with AXMI-028 and AXMI-029 by an Aerosol Beam

As an alternative method to Agrobacterium-mediated transformation, maize may be transformed using other methods, such as for example, an aerosol beam method. Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the pesticidal polypeptides of the invention in plant cells are accelerated into plant tissue using an aerosol beam accelerator, using conditions essentially as described in PCT Publication No. WO/0138514. After beaming, embryos are incubated for about 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for about 5 days at 25° C. in the dark, then transferred to selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) up to 3 g/L is added, and the mixture is autoclaved. After cooling to 50° C., 2 ml/L of a 5 mg/ml stock solution of Silver Nitrate (Phytotechnology Labs) is added. The recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polypeptide with insecticidal activity, selected from the group consisting of:
   a) a polypeptide comprising the amino acid sequence of SEQ ID NO:4;
   b) a polypeptide comprising an amino acid sequence having at least 95% sequence identity to the amino acid sequence of SEQ ID NO:4;
   c) a polypeptide that is encoded by the nucleotide sequence of SEQ ID NO:3;
   d) a polypeptide that is encoded by a nucleotide sequence having at least 95% sequence identity to the nucleotide sequence of SEQ ID NO:3 and,
   e) a polypeptide encoded by the delta endotoxin nucleotide sequence of the DNA insert of the plasmid deposited as Accession No. NRRL B-30806.

2. The polypeptide of claim 1 further comprising heterologous amino acid sequences.

3. A composition comprising the polypeptide of claim 1.

4. The composition of claim 3, wherein said composition is selected from the group consisting of a powder, dust, pellet, granule, spray, emulsion, colloid, and solution.

5. The composition of claim 3, wherein said composition is prepared by desiccation, lyophilization, homogenization, extraction, filtration, centrifugation, sedimentation, or concentration of a culture of *Bacillus thuringiensis* cells.

6. The composition of claim 3, comprising from about 1% to about 99% by weight of said polypeptide.

7. A method for controlling a lepidopteran or coleopteran pest population comprising contacting said population with an insecticidally effective amount of a polypeptide of claim 1.

8. A method for killing a lepidopteran or coleopteran pest, comprising contacting said pest with, or feeding to said pest, an insecticidally effective amount of a polypeptide of claim 1.

* * * * *

```
                             SEQUENCE LISTING

<160> NUMBER OF SEQ ID NOS: 21

<210> SEQ ID NO 1
<211> LENGTH: 3393
<212> TYPE: DNA
<213> ORGANISM: Bacillus thuringiensis
<220> FEATURE:
<221> NAME/KEY: CDS
<222> LOCATION: (1)...(3393)

<400> SEQUENCE: 1 atg aat caa aaa aac tat gaa att ata ggt gct tca aca aac ggc aca      48
Met Asn Gln Lys Asn Tyr Glu Ile Ile Gly Ala Ser Thr Asn Gly Thr
 1               5                  10                  15 att gaa tta cct gaa gat tac aac act ata gtc agc ccc tat gat gct      96
Ile Glu Leu Pro Glu Asp Tyr Asn Thr Ile Val Ser Pro Tyr Asp Ala
            20                  25                  30 cca gca tcc gtt act aca act att gaa att act gga acc ata cta agc    144
Pro Ala Ser Val Thr Thr Thr Ile Glu Ile Thr Gly Thr Ile Leu Ser
        35                  40                  45 gat tta ggt gtt cca gga gca tca tca gtt agt tta ctt ttg aat aaa    192
Asp Leu Gly Val Pro Gly Ala Ser Ser Val Ser Leu Leu Leu Asn Lys
    50                  55                  60 ctt ata aat cta tta tgg cca aat gat acc aat act gtg tgg ggg aca    240
Leu Ile Asn Leu Leu Trp Pro Asn Asp Thr Asn Thr Val Trp Gly Thr
 65                  70                  75                  80 ttc gga aaa gaa acc gct gat ctt cta aat gaa gtg tta tct cca gat    288
Phe Gly Lys Glu Thr Ala Asp Leu Leu Asn Glu Val Leu Ser Pro Asp
                 85                  90                  95 gat cca gta gta aaa gat gca aat acc att tta aaa gga ata aac gga    336
Asp Pro Val Val Lys Asp Ala Asn Thr Ile Leu Lys Gly Ile Asn Gly
            100                 105                 110 tcc ctt aac tta tat tta aat gca ctt gaa ata tgg aaa aaa gac ccc    384
Ser Leu Asn Leu Tyr Leu Asn Ala Leu Glu Ile Trp Lys Lys Asp Pro
        115                 120                 125 aac aac tta act acc ata gag aat gtc aca gat tac ttt cgt agt ttg    432
Asn Asn Leu Thr Thr Ile Glu Asn Val Thr Asp Tyr Phe Arg Ser Leu
    130                 135                 140 aat gtg gtt ttt aca cat gat atg cct tca ttt gct gta cct gga tat    480
Asn Val Val Phe Thr His Asp Met Pro Ser Phe Ala Val Pro Gly Tyr
145                 150                 155                 160 gaa acg aag tta tta aca att tat gca caa gct gca aat ctt cat tta    528
Glu Thr Lys Leu Leu Thr Ile Tyr Ala Gln Ala Ala Asn Leu His Leu
                165                 170                 175 ctt tta tta aga gat gct tct agg ttt gga gaa ggt tgg gga ctg act    576
Leu Leu Leu Arg Asp Ala Ser Arg Phe Gly Glu Gly Trp Gly Leu Thr
            180                 185                 190 caa gaa atc ata aat act aac tat aat gat caa tta cga ttg aca gca    624
Gln Glu Ile Ile Asn Thr Asn Tyr Asn Asp Gln Leu Arg Leu Thr Ala
        195                 200                 205 gaa tac acg gac cat tgt gta aag tgg tac aac gca gga tta gaa aaa    672
Glu Tyr Thr Asp His Cys Val Lys Trp Tyr Asn Ala Gly Leu Glu Lys
    210                 215                 220 tta aaa ggg aat tta act ggg gaa aat tgg tat act tat aat aga ttt    720
```

-continued

```
Leu Lys Gly Asn Leu Thr Gly Glu Asn Trp Tyr Thr Tyr Asn Arg Phe
225                 230                 235                 240 cgt aga gaa atg acg tta atg gtg tta gac gta gtt gca tta ttt cca        768
Arg Arg Glu Met Thr Leu Met Val Leu Asp Val Val Ala Leu Phe Pro
                245                 250                 255 aac tac gat aca cga atg tac ccg atc gga acg tca tca gaa ctt aca        816
Asn Tyr Asp Thr Arg Met Tyr Pro Ile Gly Thr Ser Ser Glu Leu Thr
            260                 265                 270 aga atg atc tat aca gat cca att gct tat aca caa agc gat cca tgg        864
Arg Met Ile Tyr Thr Asp Pro Ile Ala Tyr Thr Gln Ser Asp Pro Trp
        275                 280                 285 tac aag ata aca tct ctt tct ttt tca aat att gaa aac agt gcg att        912
Tyr Lys Ile Thr Ser Leu Ser Phe Ser Asn Ile Glu Asn Ser Ala Ile
    290                 295                 300 cca agt cct tct ttc ttc agg tgg cta aaa tcc gtt tca att aat agc        960
Pro Ser Pro Ser Phe Phe Arg Trp Leu Lys Ser Val Ser Ile Asn Ser
305                 310                 315                 320 cag tgg tgg ggc agt ggt cct agt caa acc tac tat tgg gtt gga cat       1008
Gln Trp Trp Gly Ser Gly Pro Ser Gln Thr Tyr Tyr Trp Val Gly His
                325                 330                 335 gaa ttg gta tat tct aat tca aat tct aat caa tca ctt aaa gtt aaa       1056
Glu Leu Val Tyr Ser Asn Ser Asn Ser Asn Gln Ser Leu Lys Val Lys
            340                 345                 350 tat gga gac cct aat tct ttt att gag ccc cct gat tct ttc agt ttt       1104
Tyr Gly Asp Pro Asn Ser Phe Ile Glu Pro Pro Asp Ser Phe Ser Phe
        355                 360                 365 tct tct acg gat gtt tac aga aca ata tct gtt gtt aga aat tca gta       1152
Ser Ser Thr Asp Val Tyr Arg Thr Ile Ser Val Val Arg Asn Ser Val
    370                 375                 380 agt aat tat ata gta agt gaa gtt cga ttc aat tca att agt agt aca       1200
Ser Asn Tyr Ile Val Ser Glu Val Arg Phe Asn Ser Ile Ser Ser Thr
385                 390                 395                 400 aat caa att agt gaa gaa att tat aaa cat caa tca aat tgg agt aga       1248
Asn Gln Ile Ser Glu Glu Ile Tyr Lys His Gln Ser Asn Trp Ser Arg
                405                 410                 415 caa gaa acc aaa gat tca att aca gaa cta tcc tta gct gct aat ccc       1296
Gln Glu Thr Lys Asp Ser Ile Thr Glu Leu Ser Leu Ala Ala Asn Pro
            420                 425                 430 cca aca aca ttt gga aat gta gca gaa tac agt cat aga tta gca tat       1344
Pro Thr Thr Phe Gly Asn Val Ala Glu Tyr Ser His Arg Leu Ala Tyr
        435                 440                 445 att tca gag gca tac caa agt cac aac cca tca aaa tac cca acc tac       1392
Ile Ser Glu Ala Tyr Gln Ser His Asn Pro Ser Lys Tyr Pro Thr Tyr
    450                 455                 460 att cct gta ttc ggt tgg acg cat aca agc gta cgt tac gat aat aaa       1440
Ile Pro Val Phe Gly Trp Thr His Thr Ser Val Arg Tyr Asp Asn Lys
465                 470                 475                 480 atc ttc ccg gac aaa atc act caa att cca gct gtt aaa agc tcc tca       1488
Ile Phe Pro Asp Lys Ile Thr Gln Ile Pro Ala Val Lys Ser Ser Ser
                485                 490                 495 gcc caa ggt gga tca tgg aaa aat ata gtg aaa ggc ccc ggg ttt act       1536
Ala Gln Gly Gly Ser Trp Lys Asn Ile Val Lys Gly Pro Gly Phe Thr
            500                 505                 510 gga gga gat gtg aca act gca gtt tcg cca gca act gta acc gac ata       1584
Gly Gly Asp Val Thr Thr Ala Val Ser Pro Ala Thr Val Thr Asp Ile
        515                 520                 525 ata aaa ata caa gtt act cta gat cca aat tca ctt tca caa aaa tat       1632
Ile Lys Ile Gln Val Thr Leu Asp Pro Asn Ser Leu Ser Gln Lys Tyr
    530                 535                 540
```

```
                                                    -continued cgt gca cga ctt cgc tat gct tcc aat gca ttt gta cca gct aca ttg   1680
Arg Ala Arg Leu Arg Tyr Ala Ser Asn Ala Phe Val Pro Ala Thr Leu
545                 550                 555                 560 tat aca aat aca agt agt aat tat aat ttt gaa ctt aaa aaa ggt aca   1728
Tyr Thr Asn Thr Ser Ser Asn Tyr Asn Phe Glu Leu Lys Lys Gly Thr
                565                 570                 575 act gaa cag ttt aca aca tat aat tca tac cag tat gta gat atc cca   1776
Thr Glu Gln Phe Thr Thr Tyr Asn Ser Tyr Gln Tyr Val Asp Ile Pro
            580                 585                 590 ggt tca ata caa ttt aat aat act tct gat aca gtc tct gtt tat ttg   1824
Gly Ser Ile Gln Phe Asn Asn Thr Ser Asp Thr Val Ser Val Tyr Leu
        595                 600                 605 cat atg gat tca aca tct aat gta aac gtt cat gta gat aga att gaa   1872
His Met Asp Ser Thr Ser Asn Val Asn Val His Val Asp Arg Ile Glu
610                 615                 620 ttc att cca ata gat gaa aat tac gat gaa aga ttt caa tta gaa aaa   1920
Phe Ile Pro Ile Asp Glu Asn Tyr Asp Glu Arg Phe Gln Leu Glu Lys
625                 630                 635                 640 gca cag aaa gcc gtg aat gcc ttg ttt aca gcg gga aga aat gca ctc   1968
Ala Gln Lys Ala Val Asn Ala Leu Phe Thr Ala Gly Arg Asn Ala Leu
                645                 650                 655 caa aca gat gta aca gat tac aaa gtg gat cag gtt tca att tta gtg   2016
Gln Thr Asp Val Thr Asp Tyr Lys Val Asp Gln Val Ser Ile Leu Val
            660                 665                 670 gat tgt gta tca ggg gag tta tat cca aat gag aaa cgc gaa cta cta   2064
Asp Cys Val Ser Gly Glu Leu Tyr Pro Asn Glu Lys Arg Glu Leu Leu
        675                 680                 685 agt tta gtc aaa tat gca aaa cgt tta agc tat tcg cgg aat tta ctt   2112
Ser Leu Val Lys Tyr Ala Lys Arg Leu Ser Tyr Ser Arg Asn Leu Leu
690                 695                 700 ctg gat cca aca ttc gac tct atc aat tcg cct gag gag aat ggc tgg   2160
Leu Asp Pro Thr Phe Asp Ser Ile Asn Ser Pro Glu Glu Asn Gly Trp
705                 710                 715                 720 tac gga agt aat ggt att gca att ggc agt ggg aat att gta ttc aaa   2208
Tyr Gly Ser Asn Gly Ile Ala Ile Gly Ser Gly Asn Ile Val Phe Lys
                725                 730                 735 gga aac tat tta att ttc tca ggt acc aat gat gaa cag tat cca acg   2256
Gly Asn Tyr Leu Ile Phe Ser Gly Thr Asn Asp Glu Gln Tyr Pro Thr
            740                 745                 750 tat ctc tat caa aaa ata gac gaa act aag tta aaa gaa tat aca cgt   2304
Tyr Leu Tyr Gln Lys Ile Asp Glu Thr Lys Leu Lys Glu Tyr Thr Arg
        755                 760                 765 tat aaa ctg aga ggt ttt atc gag agt agt cag gat tta gaa gca tac   2352
Tyr Lys Leu Arg Gly Phe Ile Glu Ser Ser Gln Asp Leu Glu Ala Tyr
770                 775                 780 gtg att cgt tat gat gca aaa cat caa aca atg gat gta tcc aat aat   2400
Val Ile Arg Tyr Asp Ala Lys His Gln Thr Met Asp Val Ser Asn Asn
785                 790                 795                 800 cta ttc tca gat att act cct gta aat gca tgc gga gaa cca aat cgt   2448
Leu Phe Ser Asp Ile Thr Pro Val Asn Ala Cys Gly Glu Pro Asn Arg
                805                 810                 815 tgt gcg gca cta cca tac ctg gat gaa aat cca aga tta gaa tgt agt   2496
Cys Ala Ala Leu Pro Tyr Leu Asp Glu Asn Pro Arg Leu Glu Cys Ser
            820                 825                 830 tcg ata caa gat ggt att tta tct gat tcg cat tcg ttt tct ctc cat   2544
Ser Ile Gln Asp Gly Ile Leu Ser Asp Ser His Ser Phe Ser Leu His
        835                 840                 845 ata gat aca ggt tca att gat ttc aat gag aac gta gga att tgg gtg   2592
Ile Asp Thr Gly Ser Ile Asp Phe Asn Glu Asn Val Gly Ile Trp Val
850                 855                 860
```

-continued

```
ttg ttt aaa att tct aca cct gaa gga tat gcg aga ttt gga aac cta      2640
Leu Phe Lys Ile Ser Thr Pro Glu Gly Tyr Ala Arg Phe Gly Asn Leu
865                 870                 875                 880 gaa gtg att gaa gat ggc cca gtc att gga gaa gca tta gcc cgt gtg      2688
Glu Val Ile Glu Asp Gly Pro Val Ile Gly Glu Ala Leu Ala Arg Val
            885                 890                 895 aaa cgc caa gaa acg aag tgg aga aac aag ttg aca caa ctg cga acg      2736
Lys Arg Gln Glu Thr Lys Trp Arg Asn Lys Leu Thr Gln Leu Arg Thr
    900                 905                 910 gaa aca caa gcg att tat aca cga gca aaa caa gcc att gat aat tta      2784
Glu Thr Gln Ala Ile Tyr Thr Arg Ala Lys Gln Ala Ile Asp Asn Leu
915                 920                 925 ttc aca aat gca cag gac tct cac tta aaa ata ggt gct aca ttt gcg      2832
Phe Thr Asn Ala Gln Asp Ser His Leu Lys Ile Gly Ala Thr Phe Ala
930                 935                 940 tca att gtg gct gca aga aag att gtc caa tcc ata cgt gaa gcg tat      2880
Ser Ile Val Ala Ala Arg Lys Ile Val Gln Ser Ile Arg Glu Ala Tyr
945                 950                 955                 960 atg tca tgg tta tct att gtc cca ggt gta aat tat cct ata gtt aca      2928
Met Ser Trp Leu Ser Ile Val Pro Gly Val Asn Tyr Pro Ile Val Thr
            965                 970                 975 gaa ttg aat gag aga ata cag caa gca ttt caa tta tat gat gta cga      2976
Glu Leu Asn Glu Arg Ile Gln Gln Ala Phe Gln Leu Tyr Asp Val Arg
    980                 985                 990 aat gtc gta cgt aat ggc cga ttc cag agt gga aca tcc gat tgg att      3024
Asn Val Val Arg Asn Gly Arg Phe Gln Ser Gly Thr Ser Asp Trp Ile
995                 1000                1005 gta acc tct gac gta agg gta caa gaa gaa aat ggg aat aac gta tta      3072
Val Thr Ser Asp Val Arg Val Gln Glu Glu Asn Gly Asn Asn Val Leu
1010                1015                1020 gtt ctt tcc aat tgg gat gcg caa gta tta caa tgc atg acg ctc tac      3120
Val Leu Ser Asn Trp Asp Ala Gln Val Leu Gln Cys Met Thr Leu Tyr
1025                1030                1035                1040 caa gac cgt ggg tat atc tta cgc gta aca gca cgt aaa gaa gga ctg      3168
Gln Asp Arg Gly Tyr Ile Leu Arg Val Thr Ala Arg Lys Glu Gly Leu
            1045                1050                1055 ggc gaa ggg tat gta aca atc act gat gaa gaa gga aat aca gat caa      3216
Gly Glu Gly Tyr Val Thr Ile Thr Asp Glu Glu Gly Asn Thr Asp Gln
    1060                1065                1070 ttg aga ttt ggt gga tgc gag gag ata gat gca tct aac tcg ttc gta      3264
Leu Arg Phe Gly Gly Cys Glu Glu Ile Asp Ala Ser Asn Ser Phe Val
1075                1080                1085 tcc aca ggt tat atg aca aaa gaa cta gag ttt ttc cca gat aca gag      3312
Ser Thr Gly Tyr Met Thr Lys Glu Leu Glu Phe Phe Pro Asp Thr Glu
1090                1095                1100 aaa gtg cgt ata gaa att gga gaa aca gaa gga aca ttc cag gtg gaa      3360
Lys Val Arg Ile Glu Ile Gly Glu Thr Glu Gly Thr Phe Gln Val Glu
1105                1110                1115                1120 agt gtt gaa tta ttc ttg atg gaa gat cta tgt                          3393
Ser Val Glu Leu Phe Leu Met Glu Asp Leu Cys
            1125                1130
```

<210> SEQ ID NO 2
<211> LENGTH: 1131
<212> TYPE: PRT
<213> ORGANISM: Bacillus thuringiensis

<400> SEQUENCE: 2

Met Asn Gln Lys Asn Tyr Glu Ile Ile Gly Ala Ser Thr Asn Gly Thr
1               5                   10                  15

-continued

```
Ile Glu Leu Pro Glu Asp Tyr Asn Thr Ile Val Ser Pro Tyr Asp Ala
             20                  25                  30

Pro Ala Ser Val Thr Thr Thr Ile Glu Ile Thr Gly Thr Ile Leu Ser
         35                  40                  45

Asp Leu Gly Val Pro Gly Ala Ser Ser Val Ser Leu Leu Leu Asn Lys
     50                  55                  60

Leu Ile Asn Leu Leu Trp Pro Asn Asp Thr Asn Thr Val Trp Gly Thr
 65                  70                  75                  80

Phe Gly Lys Glu Thr Ala Asp Leu Leu Asn Glu Val Leu Ser Pro Asp
                 85                  90                  95

Asp Pro Val Val Lys Asp Ala Asn Thr Ile Leu Lys Gly Ile Asn Gly
             100                 105                 110

Ser Leu Asn Leu Tyr Leu Asn Ala Leu Glu Ile Trp Lys Lys Asp Pro
         115                 120                 125

Asn Asn Leu Thr Thr Ile Glu Asn Val Thr Asp Tyr Phe Arg Ser Leu
     130                 135                 140

Asn Val Val Phe Thr His Asp Met Pro Ser Phe Ala Val Pro Gly Tyr
145                 150                 155                 160

Glu Thr Lys Leu Leu Thr Ile Tyr Ala Gln Ala Ala Asn Leu His Leu
                 165                 170                 175

Leu Leu Leu Arg Asp Ala Ser Arg Phe Gly Glu Gly Trp Gly Leu Thr
             180                 185                 190

Gln Glu Ile Ile Asn Thr Asn Tyr Asn Asp Gln Leu Arg Leu Thr Ala
         195                 200                 205

Glu Tyr Thr Asp His Cys Val Lys Trp Tyr Asn Ala Gly Leu Glu Lys
     210                 215                 220

Leu Lys Gly Asn Leu Thr Gly Glu Asn Trp Tyr Thr Tyr Asn Arg Phe
225                 230                 235                 240

Arg Arg Glu Met Thr Leu Met Val Leu Asp Val Val Ala Leu Phe Pro
                 245                 250                 255

Asn Tyr Asp Thr Arg Met Tyr Pro Ile Gly Thr Ser Ser Glu Leu Thr
             260                 265                 270

Arg Met Ile Tyr Thr Asp Pro Ile Ala Tyr Thr Gln Ser Asp Pro Trp
         275                 280                 285

Tyr Lys Ile Thr Ser Leu Ser Phe Ser Asn Ile Glu Asn Ser Ala Ile
     290                 295                 300

Pro Ser Pro Ser Phe Phe Arg Trp Leu Lys Ser Val Ser Ile Asn Ser
305                 310                 315                 320

Gln Trp Trp Gly Ser Gly Pro Ser Gln Thr Tyr Tyr Trp Val Gly His
                 325                 330                 335

Glu Leu Val Tyr Ser Asn Ser Asn Ser Gln Ser Leu Lys Val Lys
             340                 345                 350

Tyr Gly Asp Pro Asn Ser Phe Ile Glu Pro Pro Asp Ser Phe Ser Phe
         355                 360                 365

Ser Ser Thr Asp Val Tyr Arg Thr Ile Ser Val Val Arg Asn Ser Val
     370                 375                 380

Ser Asn Tyr Ile Val Ser Glu Val Arg Phe Asn Ser Ile Ser Ser Thr
385                 390                 395                 400

Asn Gln Ile Ser Glu Glu Ile Tyr Lys His Gln Ser Asn Trp Ser Arg
                 405                 410                 415

Gln Glu Thr Lys Asp Ser Ile Thr Glu Leu Ser Leu Ala Ala Asn Pro
             420                 425                 430
```

-continued

```
Pro Thr Thr Phe Gly Asn Val Ala Glu Tyr Ser His Arg Leu Ala Tyr
        435                 440                 445

Ile Ser Glu Ala Tyr Gln Ser His Asn Pro Ser Lys Tyr Pro Thr Tyr
450                 455                 460

Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
                485                 490                 495

Ala Gln Gly Gly Ser Trp Lys Asn Ile Val Lys Gly Pro Gly Phe Thr
            500                 505                 510

Gly Gly Asp Val Thr Thr Ala Val Ser Pro Ala Thr Val Thr Asp Ile
        515                 520                 525

Ile Lys Ile Gln Val Thr Leu Asp Pro Asn Ser Leu Ser Gln Lys Tyr
    530                 535                 540

Arg Ala Arg Leu Arg Tyr Ala Ser Asn Ala Phe Val Pro Ala Thr Leu
545                 550                 555                 560

Tyr Thr Asn Thr Ser Ser Asn Tyr Asn Phe Glu Leu Lys Lys Gly Thr
                565                 570                 575

Thr Glu Gln Phe Thr Thr Tyr Asn Ser Tyr Gln Tyr Val Asp Ile Pro
            580                 585                 590

Gly Ser Ile Gln Phe Asn Asn Thr Ser Asp Thr Val Ser Val Tyr Leu
        595                 600                 605

His Met Asp Ser Thr Ser Asn Val Asn Val His Val Asp Arg Ile Glu
    610                 615                 620

Phe Ile Pro Ile Asp Glu Asn Tyr Asp Glu Arg Phe Gln Leu Glu Lys
625                 630                 635                 640

Ala Gln Lys Ala Val Asn Ala Leu Phe Thr Ala Gly Arg Asn Ala Leu
                645                 650                 655

Gln Thr Asp Val Thr Asp Tyr Lys Val Asp Gln Val Ser Ile Leu Val
            660                 665                 670

Asp Cys Val Ser Gly Glu Leu Tyr Pro Asn Glu Lys Arg Glu Leu Leu
        675                 680                 685

Ser Leu Val Lys Tyr Ala Lys Arg Leu Ser Tyr Ser Arg Asn Leu Leu
    690                 695                 700

Leu Asp Pro Thr Phe Asp Ser Ile Asn Ser Pro Glu Glu Asn Gly Trp
705                 710                 715                 720

Tyr Gly Ser Asn Gly Ile Ala Ile Gly Ser Gly Asn Ile Val Phe Lys
                725                 730                 735

Gly Asn Tyr Leu Ile Phe Ser Gly Thr Asn Asp Glu Gln Tyr Pro Thr
            740                 745                 750

Tyr Leu Tyr Gln Lys Ile Asp Glu Thr Lys Leu Lys Glu Tyr Thr Arg
        755                 760                 765

Tyr Lys Leu Arg Gly Phe Ile Glu Ser Ser Gln Asp Leu Glu Ala Tyr
    770                 775                 780

Val Ile Arg Tyr Asp Ala Lys His Gln Thr Met Asp Val Ser Asn Asn
785                 790                 795                 800

Leu Phe Ser Asp Ile Thr Pro Val Asn Ala Cys Gly Glu Pro Asn Arg
                805                 810                 815

Cys Ala Ala Leu Pro Tyr Leu Asp Glu Asn Pro Arg Leu Glu Cys Ser
            820                 825                 830

Ser Ile Gln Asp Gly Ile Leu Ser Asp Ser His Ser Phe Ser Leu His
        835                 840                 845

Ile Asp Thr Gly Ser Ile Asp Phe Asn Glu Asn Val Gly Ile Trp Val
```

```
                850             855             860
Leu Phe Lys Ile Ser Thr Pro Glu Gly Tyr Ala Arg Phe Gly Asn Leu
865                 870                 875                 880

Glu Val Ile Glu Asp Gly Pro Val Ile Gly Glu Ala Leu Ala Arg Val
            885                 890                 895

Lys Arg Gln Glu Thr Lys Trp Arg Asn Lys Leu Thr Gln Leu Arg Thr
            900                 905                 910

Glu Thr Gln Ala Ile Tyr Thr Arg Ala Lys Gln Ala Ile Asp Asn Leu
            915                 920                 925

Phe Thr Asn Ala Gln Asp Ser His Leu Lys Ile Gly Ala Thr Phe Ala
930                 935                 940

Ser Ile Val Ala Ala Arg Lys Ile Val Gln Ser Ile Arg Glu Ala Tyr
945                 950                 955                 960

Met Ser Trp Leu Ser Ile Val Pro Gly Val Asn Tyr Pro Ile Val Thr
                965                 970                 975

Glu Leu Asn Glu Arg Ile Gln Gln Ala Phe Gln Leu Tyr Asp Val Arg
            980                 985                 990

Asn Val Val Arg Asn Gly Arg Phe Gln Ser Gly Thr Ser Asp Trp Ile
            995                 1000                1005

Val Thr Ser Asp Val Arg Val Gln Glu Glu Asn Gly Asn Asn Val Leu
    1010                1015                1020

Val Leu Ser Asn Trp Asp Ala Gln Val Leu Gln Cys Met Thr Leu Tyr
1025                1030                1035                1040

Gln Asp Arg Gly Tyr Ile Leu Arg Val Thr Ala Arg Lys Glu Gly Leu
                1045                1050                1055

Gly Glu Gly Tyr Val Thr Ile Thr Asp Glu Glu Gly Asn Thr Asp Gln
                1060                1065                1070

Leu Arg Phe Gly Gly Cys Glu Glu Ile Asp Ala Ser Asn Ser Phe Val
            1075                1080                1085

Ser Thr Gly Tyr Met Thr Lys Glu Leu Glu Phe Phe Pro Asp Thr Glu
            1090                1095                1100

Lys Val Arg Ile Glu Ile Gly Glu Thr Glu Gly Thr Phe Gln Val Glu
1105                1110                1115                1120

Ser Val Glu Leu Phe Leu Met Glu Asp Leu Cys
                1125                1130

<210> SEQ ID NO 3
<211> LENGTH: 3306
<212> TYPE: DNA
<213> ORGANISM: Bacillus thuringiensis
<220> FEATURE:
<221> NAME/KEY: CDS
<222> LOCATION: (1)...(3306)

<400> SEQUENCE: 3 atg aat tat aaa gaa tat ctg aat att act gaa ggg ggg att att aac      48
Met Asn Tyr Lys Glu Tyr Leu Asn Ile Thr Glu Gly Gly Ile Ile Asn
 1               5                  10                  15 ccg acc ctt gcg ggg agc gct att gta gtt gcg cag aat gtt agt aag      96
Pro Thr Leu Ala Gly Ser Ala Ile Val Val Ala Gln Asn Val Ser Lys
                20                  25                  30 aca atc ctt aaa aaa tta ggg agt aca att ttg ggg aag att ctt ggt     144
Thr Ile Leu Lys Lys Leu Gly Ser Thr Ile Leu Gly Lys Ile Leu Gly
            35                  40                  45 agt gtt cta gat att tta tgg cca act aat act gaa gaa ata tgg ttg     192
Ser Val Leu Asp Ile Leu Trp Pro Thr Asn Thr Glu Glu Ile Trp Leu
    50                  55                  60
```

```
gaa tta ata gat gag gta gaa gaa ctg att aat caa aaa ata gag caa    240
Glu Leu Ile Asp Glu Val Glu Glu Leu Ile Asn Gln Lys Ile Glu Gln
 65              70                  75                  80 cag gta ata att gat gca gaa aca gct tta gag tca gta aaa tta aat    288
Gln Val Ile Ile Asp Ala Glu Thr Ala Leu Glu Ser Val Lys Leu Asn
                 85                  90                  95 gtt gat tta tat tta aat gca ttt gaa gaa tgg gaa aaa aga cct act    336
Val Asp Leu Tyr Leu Asn Ala Phe Glu Glu Trp Glu Lys Arg Pro Thr
            100                 105                 110 aat gaa tac agt aca gaa ctg gtc tat aaa agg ttt act gat gcg tat    384
Asn Glu Tyr Ser Thr Glu Leu Val Tyr Lys Arg Phe Thr Asp Ala Tyr
        115                 120                 125 aat tat gcg cga act agt ata cca ttt ttt aga gtt aaa act tat gaa    432
Asn Tyr Ala Arg Thr Ser Ile Pro Phe Phe Arg Val Lys Thr Tyr Glu
    130                 135                 140 gtt tct cta tta tca gtg tat gca caa gct gct aat att agt ttg ctt    480
Val Ser Leu Leu Ser Val Tyr Ala Gln Ala Ala Asn Ile Ser Leu Leu
145                 150                 155                 160 tta tcg aga gat gcg caa ata tat gga gat ttg tgg gga ttt gac gaa    528
Leu Ser Arg Asp Ala Gln Ile Tyr Gly Asp Leu Trp Gly Phe Asp Glu
                165                 170                 175 cat gac aaa gcc act ttt gat agt gaa cga aaa tta ttt aga gct gaa    576
His Asp Lys Ala Thr Phe Asp Ser Glu Arg Lys Leu Phe Arg Ala Glu
            180                 185                 190 tat ata gat cat tgc act aaa tat tat aaa gtt gga ctt gat aga cta    624
Tyr Ile Asp His Cys Thr Lys Tyr Tyr Lys Val Gly Leu Asp Arg Leu
        195                 200                 205 aaa gga tct tct tac gga tct tgg gta aat tat aat cgt tat cgt aga    672
Lys Gly Ser Ser Tyr Gly Ser Trp Val Asn Tyr Asn Arg Tyr Arg Arg
    210                 215                 220 gaa atg aca tta atg ata tta gat acc ata gca gca ttc cca tat tat    720
Glu Met Thr Leu Met Ile Leu Asp Thr Ile Ala Ala Phe Pro Tyr Tyr
225                 230                 235                 240 gac att gaa gag tac cca ata gag gtt agt act cag tta gca aga gag    768
Asp Ile Glu Glu Tyr Pro Ile Glu Val Ser Thr Gln Leu Ala Arg Glu
                245                 250                 255 gtt tat act gat cca ata ata acg tca ttt gtt gaa tca gat cat gga    816
Val Tyr Thr Asp Pro Ile Ile Thr Ser Phe Val Glu Ser Asp His Gly
            260                 265                 270 cca agt ttt tct ttc atg gaa agt aac gca att cga aaa cca cac ctt    864
Pro Ser Phe Ser Phe Met Glu Ser Asn Ala Ile Arg Lys Pro His Leu
        275                 280                 285 gtt gat tat tta gat aat ctt tat ata tat aca tcg aga ttc aga aca    912
Val Asp Tyr Leu Asp Asn Leu Tyr Ile Tyr Thr Ser Arg Phe Arg Thr
    290                 295                 300 ttt tca aat gaa ttt caa cct gat cta aat tat tgg gct gct cat aaa    960
Phe Ser Asn Glu Phe Gln Pro Asp Leu Asn Tyr Trp Ala Ala His Lys
305                 310                 315                 320 gtc aaa tat aaa tat tct ggg gat cct act tta cat gaa aca ccc ata   1008
Val Lys Tyr Lys Tyr Ser Gly Asp Pro Thr Leu His Glu Thr Pro Ile
                325                 330                 335 tat ggt aat gca tct aat tat gaa agt aca ggg aac tac tca ttt aga   1056
Tyr Gly Asn Ala Ser Asn Tyr Glu Ser Thr Gly Asn Tyr Ser Phe Arg
            340                 345                 350 ggt aat agt att tat caa acg tta tca gct cct tct gca ata ctt aca   1104
Gly Asn Ser Ile Tyr Gln Thr Leu Ser Ala Pro Ser Ala Ile Leu Thr
        355                 360                 365 ccc aat tac atc tat tat ggt ata gag caa gtt gag ttt tat ggt aac   1152
Pro Asn Tyr Ile Tyr Tyr Gly Ile Glu Gln Val Glu Phe Tyr Gly Asn
```

-continued

|  |  |  |  |  |  |  |  |  |  |  |  |  |  |  |  |
|---|---|---|---|---|---|---|---|---|---|---|---|---|---|---|---|
|  | 370 |  |  |  | 375 |  |  |  | 380 |  |  |  |  |  |  |
| aaa | ggt | aat | gta | tat | tat | aga | gga | ggt | aat | aaa | tac | cct | ctg | agt | gtg | 1200 |
| Lys | Gly | Asn | Val | Tyr | Tyr | Arg | Gly | Gly | Asn | Lys | Tyr | Pro | Leu | Ser | Val |  |
| 385 |  |  |  |  | 390 |  |  |  |  | 395 |  |  |  |  | 400 |  |
| gat | tct | gct | aat | caa | tta | cca | cca | gat | gta | gaa | cca | ata | aca | gaa | aat | 1248 |
| Asp | Ser | Ala | Asn | Gln | Leu | Pro | Pro | Asp | Val | Glu | Pro | Ile | Thr | Glu | Asn |  |
|  |  |  |  | 405 |  |  |  |  | 410 |  |  |  |  | 415 |  |  |
| tac | aat | cat | gtt | tta | tgt | cat | gct | aca | gct | gtg | cct | gta | aaa | gat | ggt | 1296 |
| Tyr | Asn | His | Val | Leu | Cys | His | Ala | Thr | Ala | Val | Pro | Val | Lys | Asp | Gly |  |
|  |  |  | 420 |  |  |  |  | 425 |  |  |  |  | 430 |  |  |  |
| ggt | aca | gtt | cct | att | ttt | tct | tgg | aca | cat | aga | agt | gcg | gat | tat | tat | 1344 |
| Gly | Thr | Val | Pro | Ile | Phe | Ser | Trp | Thr | His | Arg | Ser | Ala | Asp | Tyr | Tyr |  |
|  |  | 435 |  |  |  |  | 440 |  |  |  |  | 445 |  |  |  |  |
| aat | acc | att | tat | cca | gat | aag | att | acg | caa | ctt | cct | gca | gtc | aaa | agc | 1392 |
| Asn | Thr | Ile | Tyr | Pro | Asp | Lys | Ile | Thr | Gln | Leu | Pro | Ala | Val | Lys | Ser |  |
|  | 450 |  |  |  |  | 455 |  |  |  |  | 460 |  |  |  |  |  |
| act | cct | tct | cca | gaa | gtg | gaa | ggg | ctt | aaa | gtg | caa | gaa | ggt | cca | ggc | 1440 |
| Thr | Pro | Ser | Pro | Glu | Val | Glu | Gly | Leu | Lys | Val | Gln | Glu | Gly | Pro | Gly |  |
| 465 |  |  |  |  | 470 |  |  |  |  | 475 |  |  |  |  | 480 |  |
| ttt | aca | ggt | gga | gat | ctt | gtt | gta | gca | aaa | tca | agt | aat | caa | act | att | 1488 |
| Phe | Thr | Gly | Gly | Asp | Leu | Val | Val | Ala | Lys | Ser | Ser | Asn | Gln | Thr | Ile |  |
|  |  |  |  | 485 |  |  |  |  | 490 |  |  |  |  | 495 |  |  |
| gtt | agg | tta | aag | gtt | acg | gta | gat | tct | ccg | gga | aca | caa | aag | tat | cgt | 1536 |
| Val | Arg | Leu | Lys | Val | Thr | Val | Asp | Ser | Pro | Gly | Thr | Gln | Lys | Tyr | Arg |  |
|  |  |  | 500 |  |  |  |  | 505 |  |  |  |  | 510 |  |  |  |
| ata | aga | cta | aaa | tat | gcg | gct | act | agt | aat | ttt | tat | cta | ggt | gct | tat | 1584 |
| Ile | Arg | Leu | Lys | Tyr | Ala | Ala | Thr | Ser | Asn | Phe | Tyr | Leu | Gly | Ala | Tyr |  |
|  |  | 515 |  |  |  |  | 520 |  |  |  |  | 525 |  |  |  |  |
| gca | gga | agt | aat | ggg | gga | aac | gga | att | cca | ggt | atc | agt | act | gtt | cct | 1632 |
| Ala | Gly | Ser | Asn | Gly | Gly | Asn | Gly | Ile | Pro | Gly | Ile | Ser | Thr | Val | Pro |  |
|  | 530 |  |  |  |  | 535 |  |  |  |  | 540 |  |  |  |  |  |
| aaa | aca | atg | aat | ata | gaa | gat | cct | ctt | tca | tat | act | tca | ttt | gct | tat | 1680 |
| Lys | Thr | Met | Asn | Ile | Glu | Asp | Pro | Leu | Ser | Tyr | Thr | Ser | Phe | Ala | Tyr |  |
| 545 |  |  |  |  | 550 |  |  |  |  | 555 |  |  |  |  | 560 |  |
| att | gat | tta | cct | gat | tca | tat | act | ttt | agt | caa | aaa | gac | gag | gtt | ata | 1728 |
| Ile | Asp | Leu | Pro | Asp | Ser | Tyr | Thr | Phe | Ser | Gln | Lys | Asp | Glu | Val | Ile |  |
|  |  |  |  | 565 |  |  |  |  | 570 |  |  |  |  | 575 |  |  |
| aga | ttc | act | ata | aat | ata | tac | gaa | tca | ggc | gga | gcc | gta | tat | gca | gac | 1776 |
| Arg | Phe | Thr | Ile | Asn | Ile | Tyr | Glu | Ser | Gly | Gly | Ala | Val | Tyr | Ala | Asp |  |
|  |  |  | 580 |  |  |  |  | 585 |  |  |  |  | 590 |  |  |  |
| aaa | gtt | gaa | ttt | atc | ccc | gtg | gat | gct | gat | tac | gat | gaa | gga | gtt | caa | 1824 |
| Lys | Val | Glu | Phe | Ile | Pro | Val | Asp | Ala | Asp | Tyr | Asp | Glu | Gly | Val | Gln |  |
|  |  | 595 |  |  |  |  | 600 |  |  |  |  | 605 |  |  |  |  |
| ttg | gaa | aaa | gca | cag | aaa | gcc | gtg | aat | gcc | ttg | ttt | aca | gcg | gga | aga | 1872 |
| Leu | Glu | Lys | Ala | Gln | Lys | Ala | Val | Asn | Ala | Leu | Phe | Thr | Ala | Gly | Arg |  |
|  | 610 |  |  |  |  | 615 |  |  |  |  | 620 |  |  |  |  |  |
| aac | gca | cta | caa | aca | gat | gtg | aca | gat | tac | aaa | gta | gat | cag | gtg | tca | 1920 |
| Asn | Ala | Leu | Gln | Thr | Asp | Val | Thr | Asp | Tyr | Lys | Val | Asp | Gln | Val | Ser |  |
| 625 |  |  |  |  | 630 |  |  |  |  | 635 |  |  |  |  | 640 |  |
| att | tta | gtg | gat | tgt | gta | tca | ggg | gag | tta | tac | ccc | aat | gag | aaa | cgc | 1968 |
| Ile | Leu | Val | Asp | Cys | Val | Ser | Gly | Glu | Leu | Tyr | Pro | Asn | Glu | Lys | Arg |  |
|  |  |  |  | 645 |  |  |  |  | 650 |  |  |  |  | 655 |  |  |
| gaa | cta | caa | aat | cta | atc | aaa | tac | gca | aaa | cgt | ttg | agc | tat | tcc | cgt | 2016 |
| Glu | Leu | Gln | Asn | Leu | Ile | Lys | Tyr | Ala | Lys | Arg | Leu | Ser | Tyr | Ser | Arg |  |
|  |  |  | 660 |  |  |  |  | 665 |  |  |  |  | 670 |  |  |  |
| aat | tta | ctc | cta | gat | cca | aca | ttc | gat | tct | atc | aat | tca | tca | gat | gag | 2064 |
| Asn | Leu | Leu | Leu | Asp | Pro | Thr | Phe | Asp | Ser | Ile | Asn | Ser | Ser | Asp | Glu |  |
|  |  | 675 |  |  |  |  | 680 |  |  |  |  | 685 |  |  |  |  |
| aat | ggc | tgg | tac | gga | agt | aat | ggt | att | gca | atc | ggc | agt | ggg | aat | att | 2112 |

```
                Asn Gly Trp Tyr Gly Ser Asn Gly Ile Ala Ile Gly Ser Gly Asn Ile
                    690                 695                 700 gta ttc aaa ggg aac tac tta att ttc tca ggt acc aat gat gaa caa       2160
Val Phe Lys Gly Asn Tyr Leu Ile Phe Ser Gly Thr Asn Asp Glu Gln
705                 710                 715                 720 tat cca acc tat ctc tat caa aaa ata gac gaa tct aag tta aaa gaa       2208
Tyr Pro Thr Tyr Leu Tyr Gln Lys Ile Asp Glu Ser Lys Leu Lys Glu
                725                 730                 735 tat aca cgt tat aaa ctg aga ggt ttt atc gag agt agt cag gat tta       2256
Tyr Thr Arg Tyr Lys Leu Arg Gly Phe Ile Glu Ser Ser Gln Asp Leu
            740                 745                 750 gaa gca tac gtg att cgt tat gat gca aaa cat caa aca atg gat gta       2304
Glu Ala Tyr Val Ile Arg Tyr Asp Ala Lys His Gln Thr Met Asp Val
        755                 760                 765 tcc aat aat cta ttc tca gat att act cct gta aat gca tgc gga gaa       2352
Ser Asn Asn Leu Phe Ser Asp Ile Thr Pro Val Asn Ala Cys Gly Glu
    770                 775                 780 cca aat cgt tgt gcg gca cta cca tac ctg gat gaa aat cca aga tta       2400
Pro Asn Arg Cys Ala Ala Leu Pro Tyr Leu Asp Glu Asn Pro Arg Leu
785                 790                 795                 800 gaa tgt agt tcg ata caa gat gga att cta tct gat tcg cat tcg ttt       2448
Glu Cys Ser Ser Ile Gln Asp Gly Ile Leu Ser Asp Ser His Ser Phe
                805                 810                 815 tct ctc cat ata gat aca ggt tca att gat ttc aat gag aac gta ggc       2496
Ser Leu His Ile Asp Thr Gly Ser Ile Asp Phe Asn Glu Asn Val Gly
                820                 825                 830 att tgg gtg ttg ttt aaa att tcc aca cta gaa gga tac gcg aaa ttt       2544
Ile Trp Val Leu Phe Lys Ile Ser Thr Leu Glu Gly Tyr Ala Lys Phe
            835                 840                 845 ggg aac cta gaa gtg att gaa gat ggc cca gtc att gga gaa gca tta       2592
Gly Asn Leu Glu Val Ile Glu Asp Gly Pro Val Ile Gly Glu Ala Leu
        850                 855                 860 gcc cgt gtg aaa cgc caa gaa acg aag tgg aga aac aag ttg aca caa       2640
Ala Arg Val Lys Arg Gln Glu Thr Lys Trp Arg Asn Lys Leu Thr Gln
865                 870                 875                 880 ctg cga acg gaa aca caa gcg att tat aca aga gca aaa caa gcc att       2688
Leu Arg Thr Glu Thr Gln Ala Ile Tyr Thr Arg Ala Lys Gln Ala Ile
                885                 890                 895 gat aat tta ttc aca aat gaa cag gac tct cac tta aaa ata ggt acg       2736
Asp Asn Leu Phe Thr Asn Glu Gln Asp Ser His Leu Lys Ile Gly Thr
                900                 905                 910 aca ttt gcg tta att gtg gct gca cga aag att gtc caa tcc ata cgt       2784
Thr Phe Ala Leu Ile Val Ala Ala Arg Lys Ile Val Gln Ser Ile Arg
            915                 920                 925 gaa gcg tat atg tca tgg tta tct atc gtc cca ggt gta aat tat cct       2832
Glu Ala Tyr Met Ser Trp Leu Ser Ile Val Pro Gly Val Asn Tyr Pro
        930                 935                 940 att ttt aca gaa ttg aat gag aga gta cag caa gca ttt caa tta tat       2880
Ile Phe Thr Glu Leu Asn Glu Arg Val Gln Gln Ala Phe Gln Leu Tyr
945                 950                 955                 960 gat gta cga aat gtc gtg cgt aat ggc cga ttc cag agt gga aca tct       2928
Asp Val Arg Asn Val Val Arg Asn Gly Arg Phe Gln Ser Gly Thr Ser
                965                 970                 975 gat tgg att gta acc tct gac gta aag gta caa gaa gaa aat ggg aat       2976
Asp Trp Ile Val Thr Ser Asp Val Lys Val Gln Glu Glu Asn Gly Asn
                980                 985                 990 aac gta tta gtt ctt tcc aat tgg gat gcg caa gta tta caa tgc atg       3024
Asn Val Leu Val Leu Ser Asn Trp Asp Ala Gln Val Leu Gln Cys Met
            995                 1000                1005
```

```
acg ctc tac caa gac cgt ggg tat atc tta cgc gta aca gca cgt aag    3072
Thr Leu Tyr Gln Asp Arg Gly Tyr Ile Leu Arg Val Thr Ala Arg Lys
        1010                1015                1020 gaa gga ctg ggc gaa ggg tat gta aca atc act gat gaa gaa gga aat    3120
Glu Gly Leu Gly Glu Gly Tyr Val Thr Ile Thr Asp Glu Glu Gly Asn
1025                1030                1035                1040 aca gat caa ttg aga ttt ggt gga tgt gag gag ata gat gca tct aac    3168
Thr Asp Gln Leu Arg Phe Gly Gly Cys Glu Glu Ile Asp Ala Ser Asn
        1045                1050                1055 tcg ttc gta tcc aca ggt tat gtt aca aaa gaa cta gaa ttt ttc cca    3216
Ser Phe Val Ser Thr Gly Tyr Val Thr Lys Glu Leu Glu Phe Phe Pro
                1060                1065                1070 gat aca gag aaa gtg cgt ata gaa att gga gaa aca gaa gga ata ttc    3264
Asp Thr Glu Lys Val Arg Ile Glu Ile Gly Glu Thr Glu Gly Ile Phe
        1075                1080                1085 cag gtg gga agt gta gaa tta ttt ttg atg gaa gat cta tgt            3306
Gln Val Gly Ser Val Glu Leu Phe Leu Met Glu Asp Leu Cys
1090                1095                1100

<210> SEQ ID NO 4
<211> LENGTH: 1102
<212> TYPE: PRT
<213> ORGANISM: Bacillus thuringiensis

<400> SEQUENCE: 4

Met Asn Tyr Lys Glu Tyr Leu Asn Ile Thr Glu Gly Gly Ile Ile Asn
1               5                   10                  15

Pro Thr Leu Ala Gly Ser Ala Ile Val Ala Gln Asn Val Ser Lys
            20                  25                  30

Thr Ile Leu Lys Lys Leu Gly Ser Thr Ile Leu Gly Lys Ile Leu Gly
        35                  40                  45

Ser Val Leu Asp Ile Leu Trp Pro Thr Asn Thr Glu Glu Ile Trp Leu
    50                  55                  60

Glu Leu Ile Asp Glu Val Glu Glu Leu Ile Asn Gln Lys Ile Glu Gln
65                  70                  75                  80

Gln Val Ile Ile Asp Ala Glu Thr Ala Leu Glu Ser Val Lys Leu Asn
                85                  90                  95

Val Asp Leu Tyr Leu Asn Ala Phe Glu Glu Trp Glu Lys Arg Pro Thr
            100                 105                 110

Asn Glu Tyr Ser Thr Glu Leu Val Tyr Lys Arg Phe Thr Asp Ala Tyr
        115                 120                 125

Asn Tyr Ala Arg Thr Ser Ile Pro Phe Phe Arg Val Lys Thr Tyr Glu
    130                 135                 140

Val Ser Leu Leu Ser Val Tyr Ala Gln Ala Ala Asn Ile Ser Leu Leu
145                 150                 155                 160

Leu Ser Arg Asp Ala Gln Ile Tyr Gly Asp Leu Trp Gly Phe Asp Glu
                165                 170                 175

His Asp Lys Ala Thr Phe Asp Ser Glu Arg Lys Leu Phe Arg Ala Glu
            180                 185                 190

Tyr Ile Asp His Cys Thr Lys Tyr Tyr Lys Val Gly Leu Asp Arg Leu
        195                 200                 205

Lys Gly Ser Ser Tyr Gly Ser Trp Val Asn Tyr Asn Arg Tyr Arg Arg
    210                 215                 220

Glu Met Thr Leu Met Ile Leu Asp Thr Ile Ala Ala Phe Pro Tyr Tyr
225                 230                 235                 240

Asp Ile Glu Glu Tyr Pro Ile Glu Val Ser Thr Gln Leu Ala Arg Glu
                245                 250                 255
```

```
Val Tyr Thr Asp Pro Ile Ile Thr Ser Phe Val Glu Ser Asp His Gly
            260                 265                 270

Pro Ser Phe Ser Phe Met Glu Ser Asn Ala Ile Arg Lys Pro His Leu
            275                 280                 285

Val Asp Tyr Leu Asp Asn Leu Tyr Ile Tyr Thr Ser Arg Phe Arg Thr
            290                 295                 300

Phe Ser Asn Glu Phe Gln Pro Asp Leu Asn Tyr Trp Ala Ala His Lys
305                 310                 315                 320

Val Lys Tyr Lys Tyr Ser Gly Asp Pro Thr Leu His Glu Thr Pro Ile
                325                 330                 335

Tyr Gly Asn Ala Ser Asn Tyr Glu Ser Thr Gly Asn Tyr Ser Phe Arg
            340                 345                 350

Gly Asn Ser Ile Tyr Gln Thr Leu Ser Ala Pro Ser Ala Ile Leu Thr
            355                 360                 365

Pro Asn Tyr Ile Tyr Tyr Gly Ile Glu Gln Val Glu Phe Tyr Gly Asn
            370                 375                 380

Lys Gly Asn Val Tyr Tyr Arg Gly Gly Asn Lys Tyr Pro Leu Ser Val
385                 390                 395                 400

Asp Ser Ala Asn Gln Leu Pro Pro Asp Val Glu Pro Ile Thr Glu Asn
                405                 410                 415

Tyr Asn His Val Leu Cys His Ala Thr Ala Val Pro Val Lys Asp Gly
            420                 425                 430

Gly Thr Val Pro Ile Phe Ser Trp Thr His Arg Ser Ala Asp Tyr Tyr
            435                 440                 445

Asn Thr Ile Tyr Pro Asp Lys Ile Thr Gln Leu Pro Ala Val Lys Ser
            450                 455                 460

Thr Pro Ser Pro Glu Val Glu Gly Leu Lys Val Gln Glu Gly Pro Gly
465                 470                 475                 480

Phe Thr Gly Gly Asp Leu Val Val Ala Lys Ser Ser Asn Gln Thr Ile
                485                 490                 495

Val Arg Leu Lys Val Thr Val Asp Ser Pro Gly Thr Gln Lys Tyr Arg
            500                 505                 510

Ile Arg Leu Lys Tyr Ala Ala Thr Ser Asn Phe Tyr Leu Gly Ala Tyr
            515                 520                 525

Ala Gly Ser Asn Gly Gly Asn Gly Ile Pro Gly Ile Ser Thr Val Pro
            530                 535                 540

Lys Thr Met Asn Ile Glu Asp Pro Leu Ser Tyr Thr Ser Phe Ala Tyr
545                 550                 555                 560

Ile Asp Leu Pro Asp Ser Tyr Thr Phe Ser Gln Lys Asp Glu Val Ile
                565                 570                 575

Arg Phe Thr Ile Asn Ile Tyr Glu Ser Gly Gly Ala Val Tyr Ala Asp
            580                 585                 590

Lys Val Glu Phe Ile Pro Val Asp Ala Asp Tyr Asp Glu Gly Val Gln
            595                 600                 605

Leu Glu Lys Ala Gln Lys Ala Val Asn Ala Leu Phe Thr Ala Gly Arg
            610                 615                 620

Asn Ala Leu Gln Thr Asp Val Thr Asp Tyr Lys Val Asp Gln Val Ser
625                 630                 635                 640

Ile Leu Val Asp Cys Val Ser Gly Glu Leu Tyr Pro Asn Glu Lys Arg
                645                 650                 655

Glu Leu Gln Asn Leu Ile Lys Tyr Ala Lys Arg Leu Ser Tyr Ser Arg
            660                 665                 670
```

```
Asn Leu Leu Leu Asp Pro Thr Phe Asp Ser Ile Asn Ser Ser Asp Glu
            675                 680                 685
Asn Gly Trp Tyr Gly Ser Asn Gly Ile Ala Ile Gly Ser Gly Asn Ile
        690                 695                 700
Val Phe Lys Gly Asn Tyr Leu Ile Phe Ser Gly Thr Asn Asp Glu Gln
705                 710                 715                 720
Tyr Pro Thr Tyr Leu Tyr Gln Lys Ile Asp Glu Ser Lys Leu Lys Glu
                725                 730                 735
Tyr Thr Arg Tyr Lys Leu Arg Gly Phe Ile Glu Ser Ser Gln Asp Leu
            740                 745                 750
Glu Ala Tyr Val Ile Arg Tyr Asp Ala Lys His Gln Thr Met Asp Val
        755                 760                 765
Ser Asn Asn Leu Phe Ser Asp Ile Thr Pro Val Asn Ala Cys Gly Glu
    770                 775                 780
Pro Asn Arg Cys Ala Ala Leu Pro Tyr Leu Asp Glu Asn Pro Arg Leu
785                 790                 795                 800
Glu Cys Ser Ser Ile Gln Asp Gly Ile Leu Ser Asp Ser His Ser Phe
                805                 810                 815
Ser Leu His Ile Asp Thr Gly Ser Ile Asp Phe Asn Glu Asn Val Gly
            820                 825                 830
Ile Trp Val Leu Phe Lys Ile Ser Thr Leu Glu Gly Tyr Ala Lys Phe
        835                 840                 845
Gly Asn Leu Glu Val Ile Glu Asp Gly Pro Val Ile Gly Glu Ala Leu
    850                 855                 860
Ala Arg Val Lys Arg Gln Glu Thr Lys Trp Arg Asn Lys Leu Thr Gln
865                 870                 875                 880
Leu Arg Thr Glu Thr Gln Ala Ile Tyr Thr Arg Ala Lys Gln Ala Ile
                885                 890                 895
Asp Asn Leu Phe Thr Asn Glu Gln Asp Ser His Leu Lys Ile Gly Thr
            900                 905                 910
Thr Phe Ala Leu Ile Val Ala Ala Arg Lys Ile Val Gln Ser Ile Arg
        915                 920                 925
Glu Ala Tyr Met Ser Trp Leu Ser Ile Val Pro Gly Val Asn Tyr Pro
    930                 935                 940
Ile Phe Thr Glu Leu Asn Glu Arg Val Gln Gln Ala Phe Gln Leu Tyr
945                 950                 955                 960
Asp Val Arg Asn Val Val Arg Asn Gly Arg Phe Gln Ser Gly Thr Ser
                965                 970                 975
Asp Trp Ile Val Thr Ser Asp Val Lys Val Gln Glu Glu Asn Gly Asn
            980                 985                 990
Asn Val Leu Val Leu Ser Asn Trp Asp Ala Gln Val Leu Gln Cys Met
        995                 1000                1005
Thr Leu Tyr Gln Asp Arg Gly Tyr Ile Leu Arg Val Thr Ala Arg Lys
    1010                1015                1020
Glu Gly Leu Gly Glu Gly Tyr Val Thr Ile Thr Asp Glu Glu Gly Asn
1025                1030                1035                1040
Thr Asp Gln Leu Arg Phe Gly Gly Cys Glu Glu Ile Asp Ala Ser Asn
                1045                1050                1055
Ser Phe Val Ser Thr Gly Tyr Val Thr Lys Glu Leu Glu Phe Phe Pro
            1060                1065                1070
Asp Thr Glu Lys Val Arg Ile Glu Ile Gly Glu Thr Glu Gly Ile Phe
        1075                1080                1085
Gln Val Gly Ser Val Glu Leu Phe Leu Met Glu Asp Leu Cys
```

-continued

```
             1090                1095                1100
```

<210> SEQ ID NO 5
<211> LENGTH: 652
<212> TYPE: PRT
<213> ORGANISM: Bacillus thuringiensis

<400> SEQUENCE: 5

```
Met Ile Arg Lys Gly Gly Arg Lys Met Asn Pro Asn Asn Arg Ser Glu
 1               5                  10                  15

His Asp Thr Ile Lys Thr Thr Glu Asn Asn Glu Val Pro Thr Asn His
            20                  25                  30

Val Gln Tyr Pro Leu Ala Glu Thr Pro Asn Pro Thr Leu Glu Asp Leu
        35                  40                  45

Asn Tyr Lys Glu Phe Leu Arg Met Thr Ala Asp Asn Asn Thr Glu Ala
    50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
            100                 105                 110

Pro Trp Lys Ala Phe Met Glu Gln Val Glu Ala Leu Met Asp Gln Lys
        115                 120                 125

Ile Ala Asp Tyr Ala Lys Asn Lys Ala Leu Ala Glu Leu Gln Gly Leu
    130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu
                165                 170                 175

Leu Phe Ser Gln Ala Glu Ser His Phe Arg Asn Ser Met Pro Ser Phe
            180                 185                 190

Ala Ile Ser Gly Tyr Glu Val Leu Phe Leu Thr Thr Tyr Ala Gln Ala
        195                 200                 205

Ala Asn Thr His Leu Phe Leu Leu Lys Asp Ala Gln Ile Tyr Gly Glu
    210                 215                 220

Glu Trp Gly Tyr Glu Lys Glu Asp Ile Ala Glu Phe Tyr Lys Arg Gln
225                 230                 235                 240

Leu Lys Leu Thr Gln Glu Tyr Thr Asp His Cys Val Lys Trp Tyr Asn
                245                 250                 255

Val Gly Leu Asp Lys Leu Arg Gly Ser Ser Tyr Glu Ser Trp Val Asn
            260                 265                 270

Phe Asn Arg Tyr Arg Arg Glu Met Thr Leu Thr Val Leu Asp Leu Ile
        275                 280                 285

Ala Leu Phe Pro Leu Tyr Asp Val Arg Leu Tyr Pro Lys Glu Val Lys
    290                 295                 300

Thr Glu Leu Thr Arg Asp Val Leu Thr Asp Pro Ile Val Gly Val Asn
305                 310                 315                 320

Asn Leu Arg Gly Tyr Gly Thr Thr Phe Ser Asn Ile Glu Asn Tyr Ile
                325                 330                 335

Arg Lys Pro His Leu Phe Asp Tyr Leu His Arg Ile Gln Phe His Thr
            340                 345                 350

Arg Phe Gln Pro Gly Tyr Tyr Gly Asn Asp Ser Phe Asn Tyr Trp Ser
        355                 360                 365
```

-continued

Gly Asn Tyr Val Ser Thr Arg Pro Ser Ile Gly Ser Asn Asp Ile Ile
    370                 375                 380

Thr Ser Pro Phe Tyr Gly Asn Lys Ser Ser Glu Pro Val Gln Asn Leu
385                 390                 395                 400

Glu Phe Asn Gly Glu Lys Val Tyr Arg Ala Val Ala Asn Thr Asn Leu
                405                 410                 415

Ala Val Trp Pro Ser Ala Val Tyr Ser Gly Val Thr Lys Val Glu Phe
            420                 425                 430

Ser Gln Tyr Asn Asp Gln Thr Asp Glu Ala Ser Thr Gln Thr Tyr Asp
        435                 440                 445

Ser Lys Arg Asn Val Gly Ala Val Ser Trp Asp Ser Ile Asp Gln Leu
450                 455                 460

Pro Pro Glu Thr Thr Asp Glu Pro Leu Glu Lys Gly Tyr Ser His Gln
465                 470                 475                 480

Leu Asn Tyr Val Met Cys Phe Leu Met Gln Gly Ser Arg Gly Thr Ile
                485                 490                 495

Pro Val Leu Thr Trp Thr His Lys Ser Val Asp Phe Phe Asn Met Ile
            500                 505                 510

Asp Ser Lys Lys Ile Thr Gln Leu Pro Leu Val Lys Ala Tyr Lys Leu
        515                 520                 525

Gln Ser Gly Ala Ser Val Val Ala Gly Pro Arg Phe Thr Gly Gly Asp
530                 535                 540

Ile Ile Gln Cys Thr Glu Asn Gly Ser Ala Ala Thr Ile Tyr Val Thr
545                 550                 555                 560

Pro Asp Val Ser Tyr Ser Gln Lys Tyr Arg Ala Arg Ile His Tyr Ala
                565                 570                 575

Ser Thr Ser Gln Ile Thr Phe Thr Leu Ser Leu Asp Gly Ala Pro Phe
            580                 585                 590

Asn Gln Tyr Tyr Phe Asp Lys Thr Ile Asn Lys Gly Asp Thr Leu Thr
        595                 600                 605

Tyr Asn Ser Phe Asn Leu Ala Ser Phe Ser Thr Pro Phe Glu Leu Ser
610                 615                 620

Gly Asn Asn Leu Gln Ile Gly Val Thr Gly Leu Ser Ala Gly Asp Lys
625                 630                 635                 640

Val Tyr Ile Asp Lys Ile Glu Phe Ile Pro Val Asn
                645                 650

<210> SEQ ID NO 6
<211> LENGTH: 652
<212> TYPE: PRT
<213> ORGANISM: Bacillus thuringiensis

<400> SEQUENCE: 6

Met Asn Pro Asn Asn Arg Ser Glu His Asp Thr Ile Lys Val Thr Pro
1               5                   10                  15

Asn Ser Glu Leu Gln Thr Asn His Asn Gln Tyr Pro Leu Ala Asp Asn
            20                  25                  30

Pro Asn Ser Thr Leu Glu Glu Leu Asn Tyr Lys Glu Phe Leu Arg Met
        35                  40                  45

Thr Glu Asp Ser Ser Thr Glu Val Leu Asp Asn Ser Thr Val Lys Asp
50                  55                  60

Ala Val Gly Thr Gly Ile Ser Val Val Gly Gln Ile Leu Gly Val Val
65                  70                  75                  80

Gly Val Pro Phe Ala Gly Ala Leu Thr Ser Phe Tyr Gln Ser Phe Leu
                85                  90                  95

```
Asn Thr Ile Trp Pro Ser Asp Ala Asp Pro Trp Lys Ala Phe Met Ala
            100                 105                 110
Gln Val Glu Val Leu Ile Asp Lys Lys Ile Glu Glu Tyr Ala Lys Ser
        115                 120                 125
Lys Ala Leu Ala Glu Leu Gln Gly Leu Gln Asn Asn Phe Glu Asp Tyr
    130                 135                 140
Val Asn Ala Leu Asn Ser Trp Lys Lys Thr Pro Leu Ser Leu Arg Ser
145                 150                 155                 160
Lys Arg Ser Gln Asp Arg Ile Arg Glu Leu Phe Ser Gln Ala Glu Ser
                165                 170                 175
His Phe Arg Asn Ser Met Pro Ser Phe Ala Val Ser Lys Phe Glu Val
            180                 185                 190
Leu Phe Leu Pro Thr Tyr Ala Gln Ala Ala Asn Thr His Leu Leu Leu
        195                 200                 205
Leu Lys Asp Ala Gln Val Phe Gly Glu Glu Trp Gly Tyr Ser Ser Glu
    210                 215                 220
Asp Val Ala Glu Phe Tyr His Arg Gln Leu Lys Leu Thr Gln Gln Tyr
225                 230                 235                 240
Thr Asp His Cys Val Asn Trp Tyr Asn Val Gly Leu Asn Gly Leu Arg
                245                 250                 255
Gly Ser Thr Tyr Asp Ala Trp Val Lys Phe Asn Arg Phe Arg Arg Glu
            260                 265                 270
Met Thr Leu Thr Val Leu Asp Leu Ile Val Leu Phe Pro Phe Tyr Asp
        275                 280                 285
Ile Arg Leu Tyr Ser Lys Gly Val Lys Thr Glu Leu Thr Arg Asp Ile
    290                 295                 300
Phe Thr Asp Pro Ile Phe Ser Leu Asn Thr Leu Gln Glu Tyr Gly Pro
305                 310                 315                 320
Thr Phe Leu Ser Ile Glu Asn Ser Ile Arg Lys Pro His Leu Phe Asp
                325                 330                 335
Tyr Leu Gln Gly Ile Glu Phe His Thr Arg Leu Gln Pro Gly Tyr Phe
            340                 345                 350
Gly Lys Asp Ser Phe Asn Tyr Trp Ser Gly Asn Tyr Val Glu Thr Arg
        355                 360                 365
Pro Ser Ile Gly Ser Ser Lys Thr Ile Thr Ser Pro Phe Tyr Gly Asp
    370                 375                 380
Lys Ser Thr Glu Pro Val Gln Lys Leu Ser Phe Asp Gly Gln Lys Val
385                 390                 395                 400
Tyr Arg Thr Ile Ala Asn Thr Asp Val Ala Ala Trp Pro Asn Gly Lys
                405                 410                 415
Val Tyr Leu Gly Val Thr Lys Val Asp Phe Ser Gln Tyr Asp Asp Gln
            420                 425                 430
Lys Asn Glu Thr Ser Thr Gln Thr Tyr Asp Ser Lys Arg Asn Asn Gly
        435                 440                 445
His Val Ser Ala Gln Asp Ser Ile Asp Gln Leu Pro Pro Glu Thr Thr
    450                 455                 460
Asp Glu Pro Leu Glu Lys Ala Tyr Ser His Gln Leu Asn Tyr Ala Glu
465                 470                 475                 480
Cys Phe Leu Met Gln Asp Arg Arg Gly Thr Ile Pro Phe Phe Thr Trp
                485                 490                 495
Thr His Arg Ser Val Asp Phe Phe Asn Thr Ile Asp Ala Glu Lys Ile
            500                 505                 510
```

-continued

Thr Gln Leu Pro Val Val Lys Ala Tyr Ala Leu Ser Ser Gly Ala Ser
        515                 520                 525

Ile Ile Glu Gly Pro Gly Phe Thr Gly Gly Asn Leu Leu Phe Leu Lys
    530                 535                 540

Glu Ser Ser Asn Ser Ile Ala Lys Phe Lys Val Thr Leu Asn Ser Ala
545                 550                 555                 560

Ala Leu Leu Gln Arg Tyr Arg Val Arg Ile Arg Tyr Ala Ser Thr Thr
                565                 570                 575

Asn Leu Arg Leu Phe Val Gln Asn Ser Asn Asn Asp Phe Leu Val Ile
            580                 585                 590

Tyr Ile Asn Lys Thr Met Asn Lys Asp Asp Leu Thr Tyr Gln Thr
        595                 600                 605

Phe Asp Leu Ala Thr Thr Asn Ser Asn Met Gly Phe Ser Gly Asp Lys
    610                 615                 620

Asn Glu Leu Ile Ile Gly Ala Glu Ser Phe Val Ser Asn Glu Lys Ile
625                 630                 635                 640

Tyr Ile Asp Lys Ile Glu Phe Ile Pro Val Gln Leu
                645                 650

<210> SEQ ID NO 7
<211> LENGTH: 1138
<212> TYPE: PRT
<213> ORGANISM: Bacillus thuringiensis

<400> SEQUENCE: 7

Met Asn Leu Asn Asn Leu Asp Gly Tyr Glu Asp Ser Asn Arg Thr Leu
1               5                   10                  15

Asn Asn Ser Leu Asn Tyr Pro Thr Gln Lys Ala Leu Ser Pro Ser Leu
            20                  25                  30

Lys Asn Met Asn Tyr Gln Asp Phe Leu Ser Ile Thr Glu Arg Glu Gln
        35                  40                  45

Pro Glu Ala Leu Ala Ser Gly Asn Thr Ala Ile Asn Thr Val Val Ser
    50                  55                  60

Val Thr Gly Ala Thr Leu Ser Ala Leu Gly Val Pro Gly Ala Ser Phe
65                  70                  75                  80

Ile Thr Asn Phe Tyr Leu Lys Ile Ala Gly Leu Leu Trp Pro Glu Asn
                85                  90                  95

Gly Lys Ile Trp Asp Glu Phe Met Thr Glu Val Glu Ala Leu Ile Asp
            100                 105                 110

Gln Lys Ile Glu Glu Tyr Val Arg Asn Lys Ala Ile Ala Glu Leu Asp
        115                 120                 125

Gly Leu Gly Ser Ala Leu Asp Lys Tyr Gln Lys Ala Leu Ala Asp Trp
    130                 135                 140

Leu Gly Lys Gln Asp Asp Pro Glu Ala Ile Leu Ser Val Ala Thr Glu
145                 150                 155                 160

Phe Arg Ile Ile Asp Ser Leu Phe Glu Phe Ser Met Pro Ser Phe Lys
                165                 170                 175

Val Thr Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
        195                 200                 205

Trp Gly Phe Thr Gln Asn Asn Ile Glu Glu Asn Tyr Asn Arg Gln Lys
    210                 215                 220

Lys Arg Ile Ser Glu Tyr Ser Asp His Cys Thr Lys Trp Tyr Asn Ser
225                 230                 235                 240

```
Gly Leu Ser Arg Leu Asn Gly Ser Thr Tyr Glu Gln Trp Ile Asn Tyr
                245                 250                 255

Asn Arg Phe Arg Arg Glu Met Ile Leu Met Ala Leu Asp Leu Val Ala
            260                 265                 270

Val Phe Pro Phe His Asp Pro Arg Tyr Ser Met Glu Thr Ser Thr
        275                 280                 285

Gln Leu Thr Arg Glu Val Tyr Thr Asp Pro Val Ser Leu Ser Ile Ser
    290                 295                 300

Asn Pro Asp Ile Gly Pro Ser Phe Ser Gln Met Glu Asn Thr Ala Ile
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
                340                 345                 350

Trp Ser Ala His Lys Val Ser Phe Lys Lys Ser Glu Gln Ser Asn Leu
            355                 360                 365

Tyr Thr Thr Gly Ile Tyr Gly Lys Thr Ser Gly Tyr Ile Ser Ser Gly
    370                 375                 380

Ala Tyr Ser Phe His Gly Asn Asp Ile Tyr Arg Thr Leu Ala Ala Pro
385                 390                 395                 400

Ser Val Val Val Tyr Pro Tyr Thr Gln Asn Tyr Gly Val Glu Gln Val
                405                 410                 415

Glu Phe Tyr Gly Val Lys Gly His Val His Tyr Arg Gly Asp Asn Lys
            420                 425                 430

Tyr Asp Leu Thr Tyr Asp Ser Ile Asp Gln Leu Pro Pro Asp Gly Glu
    435                 440                 445

Pro Ile His Glu Lys Tyr Thr His Arg Leu Cys His Ala Thr Ala Ile
        450                 455                 460

Phe Lys Ser Thr Pro Asp Tyr Asp Asn Ala Thr Ile Pro Ile Phe Ser
465                 470                 475                 480

Trp Thr His Arg Ser Ala Glu Tyr Tyr Asn Arg Ile Tyr Pro Asn Lys
                485                 490                 495

Ile Thr Lys Ile Pro Ala Val Lys Met Tyr Lys Leu Asp Asp Pro Ser
                500                 505                 510

Thr Val Val Lys Gly Pro Gly Phe Thr Gly Gly Asp Leu Val Lys Arg
            515                 520                 525

Gly Ser Thr Gly Tyr Ile Gly Asp Ile Lys Ala Thr Val Asn Ser Pro
    530                 535                 540

Leu Ser Gln Lys Tyr Arg Val Arg Val Arg Tyr Ala Thr Asn Val Ser
545                 550                 555                 560

Gly Gln Phe Asn Val Tyr Ile Asn Asp Lys Ile Thr Leu Gln Thr Lys
                565                 570                 575

Phe Gln Asn Thr Val Glu Thr Ile Gly Glu Gly Lys Asp Leu Thr Tyr
            580                 585                 590

Gly Ser Phe Gly Tyr Ile Glu Tyr Ser Thr Thr Ile Gln Phe Pro Asp
    595                 600                 605

Glu His Pro Lys Ile Thr Leu His Leu Ser Asp Leu Ser Asn Asn Ser
        610                 615                 620

Ser Phe Tyr Val Asp Ser Ile Glu Phe Ile Pro Val Asp Val Asn Tyr
625                 630                 635                 640

Ala Glu Lys Glu Lys Leu Glu Lys Ala Gln Lys Ala Val Asn Thr Leu
                645                 650                 655
```

-continued

Phe Thr Glu Gly Arg Asn Ala Leu Gln Lys Asp Val Thr Asp Tyr Lys
            660                 665                 670

Val Asp Gln Val Ser Ile Leu Val Asp Cys Ile Ser Gly Asp Leu Tyr
        675                 680                 685

Pro Asn Glu Lys Arg Glu Leu Gln Asn Leu Val Lys Tyr Ala Lys Arg
    690                 695                 700

Leu Ser Tyr Ser Arg Asn Leu Leu Asp Pro Thr Phe Asp Ser Ile
705                 710                 715                 720

Asn Ser Ser Glu Glu Asn Gly Trp Tyr Gly Ser Asn Gly Ile Val Ile
                725                 730                 735

Gly Asn Gly Asp Phe Val Phe Lys Gly Asn Tyr Leu Ile Phe Ser Gly
            740                 745                 750

Thr Asn Asp Thr Gln Tyr Pro Thr Tyr Leu Tyr Gln Lys Ile Asp Glu
        755                 760                 765

Ser Lys Leu Lys Glu Tyr Thr Arg Tyr Lys Leu Lys Gly Phe Ile Glu
770                 775                 780

Ser Ser Gln Asp Leu Glu Ala Tyr Val Ile Arg Tyr Asp Ala Lys His
785                 790                 795                 800

Arg Thr Leu Asp Val Ser Asp Asn Leu Leu Pro Asp Ile Leu Pro Glu
            805                 810                 815

Asn Thr Cys Gly Glu Pro Asn Arg Cys Ala Ala Gln Gln Tyr Leu Asp
        820                 825                 830

Glu Asn Pro Ser Pro Glu Cys Ser Ser Met Gln Asp Gly Ile Leu Ser
    835                 840                 845

Asp Ser His Ser Phe Ser Leu Asn Ile Asp Thr Gly Ser Ile Asn His
850                 855                 860

Asn Glu Asn Leu Gly Ile Trp Val Leu Phe Lys Ile Ser Thr Leu Glu
865                 870                 875                 880

Gly Tyr Ala Lys Phe Gly Asn Leu Glu Val Ile Glu Asp Gly Pro Val
            885                 890                 895

Ile Gly Glu Ala Leu Ala Arg Val Lys Arg Gln Glu Thr Lys Trp Arg
        900                 905                 910

Asn Lys Leu Ala Gln Leu Thr Thr Glu Thr Gln Ala Ile Tyr Thr Arg
    915                 920                 925

Ala Lys Gln Ala Leu Asp Asn Leu Phe Ala Asn Ala Gln Asp Ser His
    930                 935                 940

Leu Lys Arg Asp Val Thr Phe Ala Glu Ile Ala Ala Arg Lys Ile
945                 950                 955                 960

Val Gln Ser Ile Arg Glu Ala Tyr Met Ser Trp Leu Ser Val Val Pro
            965                 970                 975

Gly Val Asn His Pro Ile Phe Thr Glu Leu Ser Gly Val Gln Arg
        980                 985                 990

Ala Phe Gln Leu Tyr Asp Val Arg Asn Val Val Arg Asn Gly Arg Phe
    995                 1000                1005

Leu Asn Gly Leu Ser Asp Trp Ile Val Thr Ser Asp Val Lys Val Gln
    1010                1015                1020

Glu Glu Asn Gly Asn Asn Val Leu Val Leu Asn Asn Trp Asp Ala Gln
1025                1030                1035                1040

Val Leu Gln Asn Val Lys Leu Tyr Gln Asp Arg Gly Tyr Ile Leu His
            1045                1050                1055

Val Thr Ala Arg Lys Ile Gly Ile Gly Glu Gly Tyr Ile Thr Ile Thr
        1060                1065                1070

Asp Glu Glu Gly His Thr Asp Gln Leu Arg Phe Thr Ala Cys Glu Glu

```
                    1075                1080                1085
Ile Asp Ala Ser Asn Ala Phe Ile Ser Gly Tyr Ile Thr Lys Glu Leu
    1090                1095                1100

Glu Phe Phe Pro Asp Thr Glu Lys Val His Ile Glu Ile Gly Glu Thr
1105                1110                1115                1120

Glu Gly Ile Phe Leu Val Glu Ser Ile Glu Leu Phe Leu Met Glu Glu
                1125                1130                1135

Leu Cys

<210> SEQ ID NO 8
<211> LENGTH: 1157
<212> TYPE: PRT
<213> ORGANISM: Bacillus thuringiensis

<400> SEQUENCE: 8

Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
                20                  25                  30

Pro Thr Asp Ala Leu Gln Asn Met Asn Tyr Lys Asp Tyr Leu Lys Met
            35                  40                  45

Ser Gly Gly Glu Asn Pro Glu Leu Phe Gly Asn Pro Glu Thr Phe Ile
        50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
            100                 105                 110

Glu Ile Met Glu Arg Val Glu Glu Leu Val Asp Gln Lys Ile Glu Lys
        115                 120                 125

Tyr Val Lys Asp Lys Ala Leu Ala Glu Leu Lys Gly Leu Gly Asn Ala
    130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
            180                 185                 190

Val Leu Leu Leu Ala Val Tyr Ala Gln Ala Val Asn Leu His Leu Leu
        195                 200                 205

Leu Leu Arg Asp Ala Ser Ile Phe Gly Glu Glu Trp Gly Phe Thr Pro
    210                 215                 220

Gly Glu Ile Ser Arg Phe Tyr Asn Arg Gln Val Gln Leu Thr Ala Glu
225                 230                 235                 240

Tyr Ser Asp Tyr Cys Val Lys Trp Tyr Lys Ile Gly Leu Asp Lys Leu
                245                 250                 255

Lys Gly Thr Thr Ser Lys Ser Trp Leu Asn Tyr His Gln Phe Arg Arg
            260                 265                 270

Glu Met Thr Leu Leu Val Leu Asp Leu Val Ala Leu Phe Pro Asn Tyr
        275                 280                 285

Asp Thr His Met Tyr Pro Ile Glu Thr Thr Ala Gln Leu Thr Arg Asp
    290                 295                 300

Val Tyr Thr Asp Pro Ile Ala Phe Asn Ile Val Thr Ser Thr Gly Phe
```

-continued

```
            305                 310                 315                 320
Cys Asn Pro Trp Ser Thr His Ser Gly Ile Leu Phe Tyr Glu Val Glu
                325                 330                 335
Asn Asn Val Ile Arg Pro Pro His Leu Phe Asp Ile Leu Ser Ser Val
                340                 345                 350
Glu Ile Asn Thr Ser Arg Gly Gly Ile Thr Leu Asn Asn Asp Ala Tyr
                355                 360                 365
Ile Asn Tyr Trp Ser Gly His Thr Leu Lys Tyr Arg Arg Thr Ala Asp
                370                 375                 380
Ser Thr Val Thr Tyr Thr Ala Asn Tyr Gly Arg Ile Thr Ser Glu Lys
385                 390                 395                 400
Asn Ser Phe Ala Leu Glu Asp Arg Asp Ile Phe Glu Ile Asn Ser Thr
                405                 410                 415
Val Ala Asn Leu Ala Asn Tyr Tyr Gln Lys Ala Tyr Gly Val Pro Gly
                420                 425                 430
Ser Trp Phe His Met Val Lys Arg Gly Thr Ser Thr Thr Ala Tyr
                435                 440                 445
Leu Tyr Ser Lys Thr His Thr Ala Leu Gln Gly Cys Thr Gln Val Tyr
450                 455                 460
Glu Ser Ser Asp Glu Ile Pro Leu Asp Arg Thr Val Pro Val Ala Glu
465                 470                 475                 480
Ser Tyr Ser His Arg Leu Ser His Ile Thr Ser His Ser Phe Ser Lys
                485                 490                 495
Asn Gly Ser Ala Tyr Tyr Gly Ser Phe Pro Val Phe Val Trp Thr His
                500                 505                 510
Thr Ser Ala Asp Leu Asn Asn Thr Ile Tyr Ser Asp Lys Ile Thr Gln
                515                 520                 525
Ile Pro Ala Val Lys Gly Asp Met Leu Tyr Leu Gly Gly Ser Val Val
                530                 535                 540
Gln Gly Pro Gly Phe Thr Gly Gly Asp Ile Leu Lys Arg Thr Asn Pro
545                 550                 555                 560
Ser Ile Leu Gly Thr Phe Ala Val Thr Val Asn Gly Ser Leu Ser Gln
                565                 570                 575
Arg Tyr Arg Val Arg Ile Arg Tyr Ala Ser Thr Thr Asp Phe Glu Phe
                580                 585                 590
Thr Leu Tyr Leu Gly Asp Thr Ile Glu Lys Asn Arg Phe Asn Lys Thr
                595                 600                 605
Met Asp Asn Gly Ala Ser Leu Thr Tyr Glu Thr Phe Lys Phe Ala Ser
                610                 615                 620
Phe Ile Thr Asp Phe Gln Phe Arg Glu Thr Gln Asp Lys Ile Leu Leu
625                 630                 635                 640
Ser Met Gly Asp Phe Ser Ser Gly Gln Glu Val Tyr Ile Asp Arg Ile
                645                 650                 655
Glu Phe Ile Pro Val Asp Glu Thr Tyr Glu Ala Glu Gln Asp Leu Glu
                660                 665                 670
Ala Ala Lys Lys Ala Val Asn Ala Leu Phe Thr Asn Thr Lys Asp Gly
                675                 680                 685
Leu Arg Pro Gly Val Thr Asp Tyr Glu Val Asn Gln Ala Ala Asn Leu
                690                 695                 700
Val Glu Cys Leu Ser Asp Asp Leu Tyr Pro Asn Glu Lys Arg Leu Leu
705                 710                 715                 720
Phe Asp Ala Val Arg Glu Ala Lys Arg Leu Ser Gly Ala Arg Asn Leu
                725                 730                 735
```

-continued

```
Leu Gln Asp Pro Asp Phe Gln Glu Ile Asn Gly Glu Asn Gly Trp Ala
            740                 745                 750
Ala Ser Thr Gly Ile Glu Ile Val Glu Gly Asp Ala Val Phe Lys Gly
            755                 760                 765
Arg Tyr Leu Arg Leu Pro Gly Ala Arg Glu Ile Asp Thr Glu Thr Tyr
            770                 775                 780
Pro Thr Tyr Leu Tyr Gln Lys Val Glu Glu Gly Val Leu Lys Pro Tyr
785                 790                 795                 800
Thr Arg Tyr Arg Leu Arg Gly Phe Val Gly Ser Ser Gln Gly Leu Glu
            805                 810                 815
Ile Tyr Thr Ile Arg His Gln Thr Asn Arg Ile Val Lys Asn Val Pro
            820                 825                 830
Asp Asp Leu Leu Pro Asp Val Ser Pro Val Asn Ser Asp Gly Ser Ile
            835                 840                 845
Asn Arg Cys Ser Glu Gln Lys Tyr Val Asn Ser Arg Leu Glu Gly Glu
            850                 855                 860
Asn Arg Ser Gly Asp Ala His Glu Phe Ser Leu Pro Ile Asp Ile Gly
865                 870                 875                 880
Glu Leu Asp Tyr Asn Glu Asn Ala Gly Ile Trp Val Gly Phe Lys Ile
            885                 890                 895
Thr Asp Pro Glu Gly Tyr Ala Thr Leu Gly Asn Leu Glu Leu Val Glu
            900                 905                 910
Glu Gly Pro Leu Ser Gly Asp Ala Leu Glu Arg Leu Gln Arg Glu Glu
            915                 920                 925
Gln Gln Trp Lys Ile Gln Met Thr Arg Arg Arg Glu Glu Thr Asp Arg
            930                 935                 940
Arg Tyr Met Ala Ser Lys Gln Ala Val Asp Arg Leu Tyr Ala Asp Tyr
945                 950                 955                 960
Gln Asp Gln Gln Leu Asn Pro Asp Val Glu Ile Thr Asp Leu Thr Ala
            965                 970                 975
Ala Gln Asp Leu Ile Gln Ser Ile Pro Tyr Val Tyr Asn Glu Met Phe
            980                 985                 990
Pro Glu Ile Pro Gly Met Asn Tyr Thr Lys Phe Thr Glu Leu Thr Asp
            995                 1000                1005
Arg Leu Gln Gln Ala Trp Asn Leu Tyr Asp Gln Arg Asn Ala Ile Pro
            1010                1015                1020
Asn Gly Asp Phe Arg Asn Gly Leu Ser Asn Trp Asn Ala Thr Pro Gly
1025                1030                1035                1040
Val Glu Val Gln Gln Ile Asn His Thr Ser Val Leu Val Ile Pro Asn
            1045                1050                1055
Trp Asp Glu Gln Val Ser Gln Gln Phe Thr Val Gln Pro Asn Gln Arg
            1060                1065                1070
Tyr Val Leu Arg Val Thr Ala Arg Lys Glu Gly Val Gly Asn Gly Tyr
            1075                1080                1085
Val Ser Ile Arg Asp Gly Gly Asn Gln Ser Glu Thr Leu Thr Phe Ser
            1090                1095                1100
Ala Ser Asp Tyr Asp Thr Asn Gly Val Tyr Asn Asp Gln Thr Gly Tyr
1105                1110                1115                1120
Ile Thr Lys Thr Val Thr Phe Ile Pro Tyr Thr Asp Gln Met Trp Ile
            1125                1130                1135
Glu Ile Ser Glu Thr Glu Gly Thr Phe Tyr Ile Glu Ser Val Glu Leu
            1140                1145                1150
```

-continued

```
Ile Val Asp Val Glu
        1155

<210> SEQ ID NO 9
<211> LENGTH: 1189
<212> TYPE: PRT
<213> ORGANISM: Bacillus thuringiensis

<400> SEQUENCE: 9

Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365
```

```
Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
                420                 425                 430

Thr Phe Val Gln Arg Ser Gly Thr Pro Phe Leu Thr Thr Gly Val Val
            435                 440                 445

Phe Ser Trp Thr His Arg Ser Ala Thr Leu Thr Asn Thr Ile Asp Pro
        450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
    530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
        675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780
```

```
Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
            805                 810                 815

Pro Asp Leu Asp Cys Ser Cys Arg Asp Gly Glu Lys Cys Ala His His
        820                 825                 830

Ser His His Phe Thr Leu Asp Ile Asp Val Gly Cys Thr Asp Leu Asn
    835                 840                 845

Glu Asp Leu Gly Val Trp Val Ile Phe Lys Ile Lys Thr Gln Asp Gly
850                 855                 860

His Ala Arg Leu Gly Asn Leu Glu Phe Leu Glu Lys Pro Leu Leu
865                 870                 875                 880

Gly Glu Ala Leu Ala Arg Val Lys Arg Ala Glu Lys Lys Trp Arg Asp
                885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
        915                 920                 925

Gln Val Asp Thr Asn Ile Ala Met Ile His Ala Ala Asp Lys Arg Val
    930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
        995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
        1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
        1155                1160                1165

Glu Ile Gly Glu Thr Glu Gly Thr Phe Ile Val Asp Ser Val Glu Leu
    1170                1175                1180

Leu Leu Met Glu Glu
1185
```

<210> SEQ ID NO 10
<211> LENGTH: 1169
<212> TYPE: PRT
<213> ORGANISM: Bacillus thuringiensis

<400> SEQUENCE: 10

Met Ser Pro Asn Asn Gln Asn Glu Tyr Glu Ile Ile Asp Ala Thr Pro
1               5                   10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Val Ser Glu Tyr Pro Gly Ser Pro Glu Val Phe Leu
50                  55                  60

Ser Glu Gln Asp Ala Val Lys Ala Ala Ile Asp Ile Val Gly Lys Leu
65                  70                  75                  80

Leu Thr Gly Leu Gly Val Pro Phe Val Gly Pro Ile Val Ser Leu Tyr
                85                  90                  95

Thr Gln Leu Ile Asp Ile Leu Trp Pro Ser Lys Gln Lys Ser Gln Trp
            100                 105                 110

Glu Ile Phe Met Glu Gln Val Glu Glu Leu Ile Asn Gln Lys Ile Ala
        115                 120                 125

Glu Tyr Ala Arg Asn Lys Ala Leu Ser Glu Leu Glu Gly Leu Gly Asn
130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Met Ala Ala Asn Leu His Leu
        195                 200                 205

Leu Leu Leu Arg Asp Ala Ser Ile Phe Gly Glu Glu Trp Gly Leu Ser
210                 215                 220

Thr Ser Thr Ile Asn Asn Tyr Tyr Asn Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Ser Ser Ala Lys Gln Trp Ile Asp Tyr Asn Gln Phe Arg
            260                 265                 270

Arg Glu Met Thr Leu Thr Val Leu Asp Val Val Ala Leu Phe Ser Asn
        275                 280                 285

Tyr Asp Thr Arg Thr Tyr Pro Leu Ala Thr Thr Ala Gln Leu Thr Arg
290                 295                 300

Glu Val Tyr Thr Asp Pro Leu Gly Ala Val Asp Val Pro Asn Ile Gly
305                 310                 315                 320

Ser Trp Tyr Asp Lys Ala Pro Ser Phe Ser Glu Ile Glu Lys Ala Ala
                325                 330                 335

Ile Arg Pro Pro His Val Phe Asp Tyr Ile Thr Gly Leu Thr Val Tyr
            340                 345                 350

Thr Lys Lys Arg Ser Phe Thr Ser Asp Arg Tyr Met Arg Tyr Trp Ala
        355                 360                 365

Gly His Gln Ile Ser Tyr Lys His Ile Gly Thr Ser Ser Thr Phe Thr
370                 375                 380

-continued

```
Gln Met Tyr Gly Thr Asn Gln Asn Leu Gln Ser Thr Ser Asn Phe Asp
385                 390                 395                 400

Phe Thr Asn Tyr Asp Ile Tyr Lys Thr Leu Ser Asn Gly Ala Val Leu
            405                 410                 415

Leu Asp Ile Val Tyr Pro Gly Tyr Thr Tyr Thr Phe Phe Gly Met Pro
            420                 425                 430

Glu Thr Glu Phe Phe Met Val Asn Gln Leu Asn Asn Thr Arg Lys Thr
        435                 440                 445

Leu Thr Tyr Lys Pro Ala Ser Lys Asp Ile Ile Asp Arg Thr Arg Asp
    450                 455                 460

Ser Glu Leu Glu Leu Pro Pro Glu Thr Ser Gly Gln Pro Asn Tyr Glu
465                 470                 475                 480

Ser Tyr Ser His Arg Leu Gly His Ile Thr Phe Ile Tyr Ser Ser Ser
            485                 490                 495

Thr Ser Thr Tyr Val Pro Val Phe Ser Trp Thr His Arg Ser Ala Asp
            500                 505                 510

Leu Thr Asn Thr Val Lys Ser Gly Glu Ile Thr Gln Ile Pro Gly Gly
        515                 520                 525

Lys Ser Ser Thr Ile Gly Arg Asn Thr Tyr Ile Ile Lys Gly Arg Gly
530                 535                 540

Tyr Thr Gly Gly Asp Leu Val Ala Leu Thr Asp Arg Ile Gly Ser Cys
545                 550                 555                 560

Glu Phe Gln Met Ile Phe Pro Glu Ser Gln Arg Phe Arg Ile Arg Ile
            565                 570                 575

Arg Tyr Ala Ser Asn Glu Thr Ser Tyr Ile Ser Leu Tyr Gly Leu Asn
            580                 585                 590

Gln Ser Gly Thr Leu Lys Phe Asn Gln Thr Tyr Ser Asn Lys Asn Glu
        595                 600                 605

Asn Asp Leu Thr Tyr Asn Asp Phe Lys Tyr Ile Glu Tyr Pro Arg Val
    610                 615                 620

Ile Ser Val Asn Ala Ser Ser Asn Ile Gln Arg Leu Ser Ile Gly Ile
625                 630                 635                 640

Gln Thr Asn Thr Asn Leu Phe Ile Leu Asp Arg Ile Glu Phe Ile Pro
            645                 650                 655

Val Asp Glu Thr Tyr Glu Ala Glu Thr Asp Leu Glu Ala Ala Lys Lys
            660                 665                 670

Ala Val Asn Ala Leu Phe Thr Asn Thr Lys Asp Gly Leu Gln Pro Gly
        675                 680                 685

Val Thr Asp Tyr Glu Val Asn Gln Ala Ala Asn Leu Val Glu Cys Leu
    690                 695                 700

Ser Asp Asp Leu Tyr Pro Asn Glu Lys Arg Leu Leu Phe Asp Ala Val
705                 710                 715                 720

Arg Glu Ala Lys Arg Leu Ser Glu Ala Arg Asn Leu Leu Gln Asp Pro
            725                 730                 735

Asp Phe Gln Glu Ile Asn Gly Glu Asn Gly Trp Thr Ala Ser Thr Gly
            740                 745                 750

Ile Glu Val Ile Glu Gly Asp Ala Val Phe Lys Gly Arg Tyr Leu Arg
        755                 760                 765

Leu Pro Gly Ala Arg Glu Ile Asp Thr Glu Thr Tyr Pro Thr Tyr Leu
    770                 775                 780

Tyr Gln Lys Val Glu Glu Gly Val Leu Lys Pro Tyr Thr Arg Tyr Arg
785                 790                 795                 800

Leu Arg Gly Phe Val Gly Ser Ser Gln Gly Leu Glu Ile Tyr Thr Ile
```

-continued

```
                805                 810                 815
Arg His Gln Thr Asn Arg Ile Val Lys Asn Val Pro Asp Asp Leu Leu
            820                 825                 830

Pro Asp Val Pro Pro Val Asn Asn Asp Gly Arg Ile Asn Arg Cys Ser
            835                 840                 845

Glu Gln Lys Tyr Val Asn Ser Arg Leu Glu Val Glu Asn Arg Ser Gly
            850                 855                 860

Glu Ala His Glu Phe Ser Ile Pro Ile Asp Thr Gly Glu Leu Asp Tyr
865                 870                 875                 880

Asn Glu Asn Ala Gly Ile Trp Val Gly Phe Lys Ile Thr Asp Pro Glu
                885                 890                 895

Gly Tyr Ala Thr Leu Gly Asn Leu Glu Leu Val Glu Glu Gly Pro Leu
            900                 905                 910

Ser Gly Asp Ala Leu Glu Arg Leu Gln Lys Glu Gln Gln Trp Lys
            915                 920                 925

Ile Gln Met Thr Arg Arg Glu Glu Thr Asp Arg Arg Tyr Met Ala
            930                 935                 940

Ser Lys Gln Ala Val Asp Arg Leu Tyr Ala Asp Tyr Gln Asp Gln Gln
945                 950                 955                 960

Leu Asn Pro Asn Val Glu Ile Thr Asp Leu Thr Ala Ala Gln Asp Leu
            965                 970                 975

Ile Gln Ser Ile Pro Tyr Val Tyr Asn Glu Met Phe Pro Glu Ile Pro
            980                 985                 990

Gly Met Asn Tyr Thr Lys Phe Thr Glu Leu Thr Asp Arg Leu Gln Gln
            995                 1000                1005

Ala Trp Gly Leu Tyr Asp Gln Arg Asn Ala Ile Pro Asn Gly Asp Tyr
    1010                1015                1020

Arg Asn Glu Leu Ser Asn Trp Asn Thr Thr Ser Gly Val Asn Val Gln
1025                1030                1035                1040

Gln Ile Asn His Thr Ser Val Leu Val Ile Pro Asn Trp Asn Glu Gln
                1045                1050                1055

Val Ser Gln Lys Phe Thr Val Gln Pro Asn Gln Arg Tyr Val Leu Arg
            1060                1065                1070

Val Thr Ala Arg Lys Glu Gly Val Gly Asn Gly Tyr Val Ser Ile Arg
            1075                1080                1085

Asp Gly Gly Asn Gln Ser Glu Thr Leu Thr Phe Ser Ala Ser Asp Tyr
            1090                1095                1100

Asp Thr Asn Gly Met Tyr Asp Thr Gln Ala Ser Asn Thr Asn Gly Tyr
1105                1110                1115                1120

Asn Thr Asn Ser Val Tyr Met Ile Lys Pro Ala Ile Ser Arg Lys Thr
                1125                1130                1135

Val Asp Ile Ser Ser Val Tyr Asn Gln Met Trp Ile Glu Ile Ser Glu
            1140                1145                1150

Thr Glu Gly Thr Phe Tyr Ile Glu Ser Val Glu Leu Ile Val Asp Val
            1155                1160                1165

Glu
```

<210> SEQ ID NO 11
<211> LENGTH: 1138
<212> TYPE: PRT
<213> ORGANISM: Bacillus thuringiensis

<400> SEQUENCE: 11

Met Asn Leu Asn Asn Leu Gly Gly Tyr Glu Asp Ser Asn Arg Thr Leu

-continued

```
  1               5                   10                  15
Asn Asn Ser Leu Asn Tyr Pro Thr Gln Lys Ala Leu Ser Pro Ser Leu
             20                  25                  30

Lys Asn Met Asn Tyr Gln Asp Phe Leu Ser Ile Thr Glu Arg Glu Gln
             35                  40                  45

Pro Glu Ala Leu Ala Ser Gly Asn Thr Ala Ile Asn Thr Val Val Ser
             50                  55                  60

Val Thr Gly Ala Thr Leu Ser Ala Leu Gly Val Pro Gly Ala Ser Phe
 65                  70                  75                  80

Ile Thr Asn Phe Tyr Leu Lys Ile Thr Gly Leu Leu Trp Pro His Asn
                 85                  90                  95

Lys Asn Ile Trp Asp Glu Phe Met Thr Glu Val Glu Thr Leu Ile Glu
                100                 105                 110

Gln Lys Ile Glu Gln Tyr Ala Arg Asn Lys Ala Leu Ala Glu Leu Glu
            115                 120                 125

Gly Leu Gly Asn Asn Leu Thr Ile Tyr Gln Gln Ala Leu Glu Asp Trp
        130                 135                 140

Leu Asn Asn Pro Asp Asp Pro Ala Thr Ile Thr Arg Val Ile Asp Arg
145                 150                 155                 160

Phe Arg Ile Leu Asp Ala Leu Phe Glu Ser Tyr Met Pro Ser Phe Arg
                165                 170                 175

Val Ala Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
        195                 200                 205

Trp Gly Phe Thr Gln Asn Asn Ile Glu Glu Asn Tyr Asn Arg Gln Lys
    210                 215                 220

Lys His Ile Ser Glu Tyr Ser Asn His Cys Val Lys Trp Tyr Asn Ser
225                 230                 235                 240

Gly Leu Ser Arg Leu Asn Gly Ser Thr Tyr Glu Gln Trp Ile Asn Tyr
                245                 250                 255

Asn Arg Phe Arg Arg Glu Met Ile Leu Met Val Leu Asp Ile Ala Ala
            260                 265                 270

Val Phe Pro Ile Tyr Asp Pro Arg Met Tyr Ser Met Glu Thr Ser Thr
        275                 280                 285

Gln Leu Thr Arg Glu Val Tyr Thr Asp Pro Ile Ser Leu Ser Ile Ser
    290                 295                 300

Asn Pro Asp Ile Gly Pro Ser Phe Ser Gln Met Glu Asn Thr Ala Phe
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
            340                 345                 350

Trp Cys Val His Lys Val Ser Phe Lys Lys Ser Glu Gln Ser Asn Leu
        355                 360                 365

Tyr Thr Thr Gly Ile Tyr Gly Lys Thr Ser Gly Tyr Ile Ser Ser Gly
    370                 375                 380

Ala Tyr Ser Phe Arg Gly Asn Asp Ile Tyr Arg Thr Leu Ala Ala Pro
385                 390                 395                 400

Ser Val Val Val Tyr Pro Tyr Thr Gln Asn Tyr Gly Val Glu Gln Val
                405                 410                 415

Glu Phe Tyr Gly Val Lys Gly His Val His Tyr Arg Gly Asp Asn Lys
            420                 425                 430
```

```
Tyr Asp Leu Thr Tyr Asp Ser Ile Asp Gln Leu Pro Pro Asp Gly Glu
            435                 440                 445

Pro Ile His Glu Lys Tyr Thr His Arg Leu Cys His Ala Thr Ala Ile
        450                 455                 460

Ser Lys Ser Thr Pro Asp Tyr Asp Asn Ala Thr Ile Pro Ile Phe Ser
465                 470                 475                 480

Trp Thr His Arg Ser Ala Glu Tyr Tyr Asn Arg Ile Tyr Pro Asn Lys
                485                 490                 495

Ile Lys Lys Ile Pro Ala Val Lys Met Tyr Lys Leu Asp Asp Leu Ser
            500                 505                 510

Thr Val Val Lys Gly Pro Gly Phe Thr Gly Gly Asp Leu Val Lys Arg
        515                 520                 525

Gly Ser Asn Gly Tyr Ile Gly Asp Ile Lys Ala Thr Val Asn Ser Pro
    530                 535                 540

Leu Ser Gln Lys Tyr Arg Val Arg Val Arg Tyr Ala Thr Ser Val Ser
545                 550                 555                 560

Gly Leu Phe Asn Val Phe Ile Asn Asp Glu Ile Ala Leu Gln Lys Asn
                565                 570                 575

Phe Gln Ser Thr Val Glu Thr Ile Gly Glu Gly Lys Asp Leu Thr Tyr
            580                 585                 590

Gly Ser Phe Gly Tyr Ile Glu Tyr Ser Thr Thr Ile Gln Phe Pro Asn
        595                 600                 605

Glu His Pro Lys Ile Thr Leu His Leu Asn His Leu Ser Asn Asn Ser
    610                 615                 620

Pro Phe Tyr Val Asp Ser Ile Glu Phe Ile Pro Val Asp Val Asn Tyr
625                 630                 635                 640

Asp Glu Lys Glu Lys Leu Glu Lys Ala Gln Lys Ala Val Asn Thr Leu
                645                 650                 655

Phe Thr Glu Gly Arg Asn Ala Leu Gln Lys Tyr Val Thr Asp Tyr Lys
            660                 665                 670

Val Asp Gln Val Ser Ile Leu Val Asp Cys Ile Ser Gly Asp Leu Tyr
        675                 680                 685

Pro Asn Glu Lys Arg Glu Leu Gln Asn Leu Val Lys Tyr Ala Lys Arg
    690                 695                 700

Leu Ser Tyr Ser Arg Asn Leu Leu Leu Asp Pro Thr Phe Asp Ser Ile
705                 710                 715                 720

Asn Ser Ser Glu Glu Asn Gly Trp Tyr Gly Ser Asn Gly Ile Val Ile
                725                 730                 735

Gly Asn Gly Asp Phe Val Phe Lys Gly Asn Tyr Leu Ile Phe Ser Gly
            740                 745                 750

Thr Asn Asp Thr Gln Tyr Pro Thr Tyr Leu Tyr Gln Lys Ile Asp Glu
        755                 760                 765

Ser Lys Leu Lys Glu Tyr Ser Arg Tyr Lys Leu Lys Gly Phe Ile Glu
    770                 775                 780

Ser Ser Gln Asp Leu Glu Ala Tyr Val Ile Arg Tyr Asp Ala Lys His
785                 790                 795                 800

Arg Thr Leu Asp Val Ser Asp Asn Leu Leu Pro Asp Ile Leu Pro Glu
                805                 810                 815

Asn Thr Cys Gly Glu Pro Asn Arg Cys Ala Ala Gln Gln Tyr Leu Asp
            820                 825                 830

Glu Asn Pro Ser Ser Glu Cys Ser Ser Met Gln Asp Gly Ile Leu Ser
        835                 840                 845
```

-continued

```
Asp Ser His Ser Phe Ser Leu Asn Ile Asp Thr Gly Ser Ile Asn His
    850                 855                 860

Asn Glu Asn Leu Gly Ile Trp Val Leu Phe Lys Ile Ser Thr Leu Glu
865                 870                 875                 880

Gly Tyr Ala Lys Phe Gly Asn Leu Glu Val Ile Glu Asp Gly Pro Val
                885                 890                 895

Ile Gly Glu Ala Leu Ala Arg Val Lys Arg Gln Glu Thr Lys Trp Arg
            900                 905                 910

Asn Lys Leu Ala Gln Met Thr Thr Glu Thr Gln Ala Ile Tyr Thr Arg
        915                 920                 925

Ala Lys Gln Ala Leu Asp Asn Leu Phe Ala Asn Ala Gln Asp Ser His
    930                 935                 940

Leu Lys Ile Asp Val Thr Phe Ala Glu Ile Ala Ala Arg Lys Ile
945                 950                 955                 960

Val Gln Ser Ile Arg Glu Val Tyr Met Ser Trp Leu Ser Val Val Pro
                965                 970                 975

Gly Val Asn His Pro Ile Phe Thr Glu Leu Ser Gly Arg Val Gln Arg
            980                 985                 990

Ala Phe Gln Leu Tyr Asp Val Arg Asn Val Val Arg Asn Gly Arg Phe
        995                 1000                1005

Leu Asn Gly Leu Ser Asp Trp Ile Val Thr Ser Asp Val Asn Val Gln
    1010                1015                1020

Glu Glu Asn Gly Asn Asn Val Leu Val Leu Asn Asn Trp Asp Ala Gln
1025                1030                1035                1040

Val Leu Arg Asn Val Lys Leu Tyr Gln Asp Arg Gly Tyr Val Leu Arg
                1045                1050                1055

Val Thr Ala Arg Lys Ile Gly Ile Gly Glu Gly Tyr Ile Thr Ile Thr
            1060                1065                1070

Asp Glu Glu Gly His Thr Asp Gln Leu Arg Phe Thr Ala Cys Glu Glu
        1075                1080                1085

Ile Asp Ala Ser Asn Ala Phe Ile Ser Gly Tyr Ile Thr Lys Glu Leu
    1090                1095                1100

Glu Phe Phe Pro Asp Thr Glu Lys Val His Ile Glu Ile Gly Glu Thr
1105                1110                1115                1120

Glu Gly Ile Phe Leu Val Glu Ser Ile Glu Leu Phe Leu Met Glu Glu
                1125                1130                1135

Leu Cys
```

```
<210> SEQ ID NO 12
<211> LENGTH: 1160
<212> TYPE: PRT
<213> ORGANISM: Bacillus thuringiensis

<400> SEQUENCE: 12

Met Ser Pro Asn Asn Gln Asn Glu Tyr Glu Ile Ile Asp Ala Leu Ser
  1               5                  10                  15

Pro Thr Ser Val Ser Asp Asn Ser Ile Arg Tyr Pro Leu Ala Asn Asp
                20                  25                  30

Gln Thr Asn Thr Leu Gln Asn Met Asn Tyr Lys Asp Tyr Leu Lys Met
            35                  40                  45

Thr Glu Ser Thr Asn Ala Glu Leu Ser Arg Asn Pro Gly Thr Phe Ile
        50                  55                  60

Ser Ala Gln Asp Ala Val Gly Thr Gly Ile Asp Ile Val Ser Thr Ile
65                  70                  75                  80
```

-continued

```
Ile Ser Gly Leu Gly Ile Pro Val Leu Gly Glu Val Phe Ser Ile Leu
                85                  90                  95

Gly Ser Leu Ile Gly Leu Leu Trp Pro Ser Asn Asn Glu Asn Val Trp
            100                 105                 110

Gln Ile Phe Met Asn Arg Val Glu Glu Leu Ile Asp Gln Lys Ile Leu
        115                 120                 125

Asp Ser Val Arg Ser Arg Ala Ile Ala Asp Leu Ala Asn Ser Arg Ile
    130                 135                 140

Ala Val Glu Tyr Tyr Gln Asn Ala Leu Glu Asp Trp Arg Lys Asn Pro
145                 150                 155                 160

His Ser Thr Arg Ser Ala Ala Leu Val Lys Glu Arg Phe Gly Asn Ala
                165                 170                 175

Glu Ala Ile Leu Arg Thr Asn Met Gly Ser Phe Ser Gln Thr Asn Tyr
            180                 185                 190

Glu Thr Pro Leu Leu Pro Thr Tyr Ala Gln Ala Ser Leu His Leu
        195                 200                 205

Leu Val Met Arg Asp Val Gln Ile Tyr Gly Lys Glu Trp Gly Tyr Pro
    210                 215                 220

Gln Asn Asp Ile Asp Leu Phe Tyr Lys Glu Gln Val Ser Tyr Thr Ala
225                 230                 235                 240

Arg Tyr Ser Asp His Cys Val Gln Trp Tyr Asn Ala Gly Leu Asn Lys
                245                 250                 255

Leu Arg Gly Thr Gly Ala Lys Gln Trp Val Asp Tyr Asn Arg Phe Arg
            260                 265                 270

Arg Glu Met Asn Val Met Val Leu Asp Leu Val Ala Leu Phe Pro Asn
        275                 280                 285

Tyr Asp Ala Arg Ile Tyr Pro Leu Glu Thr Asn Ala Glu Leu Thr Arg
    290                 295                 300

Glu Ile Phe Thr Asp Pro Val Gly Ser Tyr Val Thr Gly Gln Ser Ser
305                 310                 315                 320

Thr Leu Ile Ser Trp Tyr Asp Met Ile Pro Ala Ala Leu Pro Ser Phe
                325                 330                 335

Ser Thr Leu Glu Asn Leu Leu Arg Lys Pro Asp Phe Phe Thr Leu Leu
            340                 345                 350

Gln Glu Ile Arg Met Tyr Thr Ser Phe Arg Gln Asn Gly Thr Ile Glu
        355                 360                 365

Tyr Tyr Asn Tyr Trp Gly Gly Gln Arg Leu Thr Leu Ser Tyr Ile Tyr
    370                 375                 380

Gly Ser Ser Phe Asn Lys Tyr Ser Gly Val Leu Ala Gly Ala Glu Asp
385                 390                 395                 400

Ile Ile Pro Val Gly Gln Asn Asp Ile Tyr Arg Val Val Trp Thr Tyr
                405                 410                 415

Ile Gly Arg Tyr Thr Asn Ser Leu Leu Gly Val Asn Pro Val Thr Phe
            420                 425                 430

Tyr Phe Ser Asn Asn Thr Gln Lys Thr Tyr Ser Lys Pro Lys Gln Phe
        435                 440                 445

Ala Gly Gly Ile Lys Thr Ile Asp Ser Gly Glu Leu Thr Tyr Glu
    450                 455                 460

Asn Tyr Gln Ser Tyr Ser His Arg Val Ser Tyr Ile Thr Ser Phe Glu
465                 470                 475                 480

Ile Lys Ser Thr Gly Gly Thr Val Leu Gly Val Val Pro Ile Phe Gly
                485                 490                 495

Trp Thr His Ser Ser Ala Ser Arg Asn Asn Phe Ile Tyr Ala Thr Lys
```

```
                  500                 505                 510
Ile Ser Gln Ile Pro Ile Asn Lys Ala Ser Arg Thr Ser Gly Gly Ala
            515                 520                 525

Val Trp Asn Phe Gln Glu Gly Leu Tyr Asn Gly Gly Pro Val Met Lys
            530                 535                 540

Leu Ser Gly Ser Gly Ser Gln Val Ile Asn Leu Arg Val Ala Thr Asp
545                 550                 555                 560

Ala Lys Gly Ala Ser Gln Arg Tyr Arg Ile Arg Tyr Ala Ser
            565                 570                 575

Asp Arg Ala Gly Lys Phe Thr Ile Ser Ser Arg Ser Pro Glu Asn Pro
            580                 585                 590

Ala Thr Tyr Ser Ala Ser Ile Ala Tyr Thr Asn Thr Met Ser Thr Asn
            595                 600                 605

Ala Ser Leu Thr Tyr Ser Thr Phe Ala Tyr Ala Glu Ser Gly Pro Ile
            610                 615                 620

Asn Leu Gly Ile Ser Gly Ser Ser Arg Thr Phe Asp Ile Ser Ile Thr
625                 630                 635                 640

Lys Glu Ala Gly Ala Ala Asn Leu Tyr Ile Asp Arg Ile Glu Phe Ile
            645                 650                 655

Pro Val Asn Thr Leu Phe Glu Ala Glu Glu Asp Leu Asp Val Ala Lys
            660                 665                 670

Lys Ala Val Asn Gly Leu Phe Thr Asn Glu Lys Asp Ala Leu Gln Thr
            675                 680                 685

Ser Val Thr Asp Tyr Gln Val Asn Gln Ala Ala Asn Leu Ile Glu Cys
            690                 695                 700

Leu Ser Asp Glu Leu Tyr Pro Asn Glu Lys Arg Met Leu Trp Asp Ala
705                 710                 715                 720

Val Lys Glu Ala Lys Arg Leu Val Gln Ala Arg Asn Leu Leu Gln Asp
            725                 730                 735

Thr Gly Phe Asn Arg Ile Asn Gly Glu Asn Gly Trp Thr Gly Ser Thr
            740                 745                 750

Gly Ile Glu Val Val Glu Gly Asp Val Leu Phe Lys Asp Arg Ser Leu
            755                 760                 765

Arg Leu Thr Ser Ala Arg Glu Ile Asp Thr Glu Thr Tyr Pro Thr Tyr
770                 775                 780

Leu Tyr Gln Gln Ile Asp Glu Ser Leu Leu Lys Pro Tyr Thr Arg Tyr
785                 790                 795                 800

Lys Leu Lys Gly Phe Ile Gly Ser Ser Gln Asp Leu Glu Ile Lys Leu
            805                 810                 815

Ile Arg His Arg Ala Asn Gln Ile Val Lys Asn Val Pro Asp Asn Leu
            820                 825                 830

Leu Pro Asp Val Arg Pro Val Asn Ser Cys Gly Gly Val Asp Arg Cys
            835                 840                 845

Ser Glu Gln Gln Tyr Val Asp Ala Asn Leu Ala Leu Glu Asn Asn Gly
            850                 855                 860

Glu Asn Gly Asn Met Ser Ser Asp Ser His Ala Phe Ser Phe His Ile
865                 870                 875                 880

Asp Thr Gly Glu Ile Asp Leu Asn Glu Asn Thr Gly Ile Trp Ile Val
            885                 890                 895

Phe Lys Ile Pro Thr Thr Asn Gly Asn Ala Thr Leu Gly Asn Leu Glu
            900                 905                 910

Phe Val Glu Glu Gly Pro Leu Ser Gly Glu Thr Leu Glu Trp Ala Gln
            915                 920                 925
```

```
Gln Gln Glu Gln Gln Trp Gln Asp Lys Met Ala Arg Lys Ala Ala
        930                 935                 940

Ser Glu Lys Thr Tyr Tyr Ala Lys Gln Ala Ile Asp Arg Leu Phe
945                 950                 955                 960

Ala Asp Tyr Gln Asp Gln Lys Leu Asn Ser Gly Val Glu Met Ser Asp
            965                 970                 975

Leu Leu Ala Ala Gln Asn Leu Val Gln Ser Ile Pro Tyr Val Tyr Asn
            980                 985                 990

Asp Ala Leu Pro Glu Ile Pro Gly Met Asn Tyr Thr Ser Phe Thr Glu
            995                 1000                1005

Leu Thr Asn Arg Leu Gln Gln Ala Trp Asn Leu Tyr Asp Leu Gln Asn
        1010                1015                1020

Ala Ile Pro Asn Gly Asp Phe Arg Asn Gly Leu Ser Asn Trp Asn Ala
1025                1030                1035                1040

Thr Ser Asp Val Asn Val Gln Gln Leu Ser Asp Thr Ser Val Leu Val
            1045                1050                1055

Ile Pro Asn Trp Asn Ser Gln Val Ser Gln Gln Phe Thr Val Gln Pro
            1060                1065                1070

Asn Tyr Arg Tyr Val Leu Arg Val Thr Ala Arg Lys Glu Gly Val Gly
            1075                1080                1085

Asp Gly Tyr Val Ile Ile Arg Asp Gly Ala Asn Gln Thr Glu Thr Leu
        1090                1095                1100

Thr Phe Asn Ile Cys Asp Asp Thr Gly Val Leu Ser Thr Asp Gln
1105                1110                1115                1120

Thr Ser Tyr Ile Thr Lys Thr Val Glu Phe Thr Pro Ser Thr Glu Gln
            1125                1130                1135

Val Trp Ile Asp Met Ser Glu Thr Glu Gly Val Phe Asn Ile Glu Ser
            1140                1145                1150

Val Glu Leu Val Leu Glu Glu Glu
        1155                1160

<210> SEQ ID NO 13
<211> LENGTH: 1228
<212> TYPE: PRT
<213> ORGANISM: Bacillus thuringiensis

<400> SEQUENCE: 13

Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
```

```
            130                 135                 140
Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Gly Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560
```

-continued

```
Val Asp Phe Asp Phe Val Ser Arg Gly Gly Thr Thr Val Asn Asn
            565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
    610                 615                 620

Val Tyr Ile Asp Lys Ile Glu Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asp Tyr His
                660                 665                 670

Ile Asp Gln Val Ser Asn Leu Val Ala Cys Leu Ser Asp Glu Phe Cys
            675                 680                 685

Leu Asp Glu Lys Arg Glu Leu Leu Glu Lys Val Lys Tyr Ala Lys Arg
    690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
                740                 745                 750

Thr Ile Gln Glu Gly Asn Asp Val Phe Lys Glu Asn Tyr Val Thr Leu
            755                 760                 765

Pro Gly Thr Phe Asn Glu Cys Tyr Pro Thr Tyr Leu Tyr Gln Lys Ile
    770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
                820                 825                 830

Ser Val Glu Ser Pro Ile Gly Arg Cys Gly Glu Pro Asn Arg Cys Ala
            835                 840                 845

Pro His Phe Glu Trp Asn Pro Asp Leu Asp Cys Ser Cys Arg Asp Gly
    850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Phe Lys
                885                 890                 895

Ile Lys Thr Gln Glu Gly His Ala Arg Leu Gly Asn Leu Glu Phe Ile
            900                 905                 910

Glu Glu Lys Pro Leu Leu Gly Glu Ala Leu Ser Arg Val Lys Arg Ala
            915                 920                 925

Glu Lys Lys Trp Arg Asp Lys Arg Glu Lys Leu Gln Leu Glu Thr Lys
    930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975
```

```
Ala Ala Asp Lys Leu Val His Arg Ile Arg Glu Ala Tyr Leu Ser Glu
            980                 985                 990

Leu Pro Val Ile Pro Gly Val Asn Ala Glu Ile Phe Glu Glu Leu Glu
            995                 1000                1005

Gly His Ile Ile Thr Ala Ile Ser Leu Tyr Asp Ala Arg Asn Val Val
            1010                1015                1020

Lys Asn Gly Asp Phe Asn Asn Gly Leu Thr Cys Trp Asn Val Lys Gly
1025                1030                1035                1040

His Val Asp Val Gln Gln Ser His His Arg Ser Asp Leu Val Ile Pro
            1045                1050                1055

Glu Trp Glu Ala Glu Val Ser Gln Ala Val Arg Val Cys Pro Gly Cys
            1060                1065                1070

Gly Tyr Ile Leu Arg Val Thr Ala Tyr Lys Glu Gly Tyr Gly Glu Gly
            1075                1080                1085

Cys Val Thr Ile His Glu Ile Glu Asn Asn Thr Asp Glu Leu Lys Phe
            1090                1095                1100

Lys Asn Arg Glu Glu Glu Val Tyr Pro Thr Asp Thr Gly Thr Cys
1105                1110                1115                1120

Asn Asp Tyr Thr Ala His Gln Gly Thr Ala Gly Cys Ala Asp Ala Cys
            1125                1130                1135

Asn Ser Arg Asn Ala Gly Tyr Glu Asp Ala Tyr Glu Val Asp Thr Thr
            1140                1145                1150

Ala Ser Val Asn Tyr Lys Pro Thr Tyr Glu Glu Glu Thr Tyr Thr Asp
            1155                1160                1165

Val Arg Arg Asp Asn His Cys Glu Tyr Asp Arg Gly Tyr Val Asn Tyr
            1170                1175                1180

Pro Pro Val Pro Ala Gly Tyr Val Thr Lys Glu Leu Glu Tyr Phe Pro
1185                1190                1195                1200

Glu Thr Asp Thr Val Trp Ile Glu Ile Gly Glu Thr Glu Gly Lys Phe
            1205                1210                1215

Ile Val Asp Ser Val Glu Leu Leu Leu Met Glu Glu
            1220                1225

<210> SEQ ID NO 14
<211> LENGTH: 1890
<212> TYPE: DNA
<213> ORGANISM: Artificial Sequence
<220> FEATURE:
<223> OTHER INFORMATION: synaxmi-028
<221> NAME/KEY: CDS
<222> LOCATION: (1)...(1890)

<400> SEQUENCE: 14 atg aac cag aag aac tac gag atc atc ggc gcg tcc acc aac ggg acg    48
Met Asn Gln Lys Asn Tyr Glu Ile Ile Gly Ala Ser Thr Asn Gly Thr
 1               5                  10                  15 atc gag ctg ccc gag gat tac aac acg atc gtc agc ccg tac gac gcg    96
Ile Glu Leu Pro Glu Asp Tyr Asn Thr Ile Val Ser Pro Tyr Asp Ala
                20                  25                  30 cct gca tca gtg aca acc acc atc gag atc acg ggg aca atc ctg tct   144
Pro Ala Ser Val Thr Thr Thr Ile Glu Ile Thr Gly Thr Ile Leu Ser
            35                  40                  45 gac ctc ggt gtg cct gga gca agt tca gtc agc ctt ctg ctc aac aag   192
Asp Leu Gly Val Pro Gly Ala Ser Ser Val Ser Leu Leu Leu Asn Lys
        50                  55                  60 ctg atc aac ctg ctc tgg ccg aac gac acc aac acc gtg tgg ggt acg   240
Leu Ile Asn Leu Leu Trp Pro Asn Asp Thr Asn Thr Val Trp Gly Thr
65                  70                  75                  80
```

| | | | | | | | | | | | | | | | | |
|---|---|---|---|---|---|---|---|---|---|---|---|---|---|---|---|---|
| ttc | ggc | aag | gag | acg | gcc | gat | ctc | ctc | aac | gag | gtc | ctg | tca | cct | gat | 288 |
| Phe | Gly | Lys | Glu | Thr | Ala | Asp | Leu | Leu | Asn | Glu | Val | Leu | Ser | Pro | Asp | |
| | | | | 85 | | | | | 90 | | | | | 95 | | |
| gac | cca | gtt | gtc | aag | gac | gct | aat | acg | atc | ctc | aag | ggg | atc | aac | ggg | 336 |
| Asp | Pro | Val | Val | Lys | Asp | Ala | Asn | Thr | Ile | Leu | Lys | Gly | Ile | Asn | Gly | |
| | | | 100 | | | | | 105 | | | | | 110 | | | |
| tcg | ctg | aac | ctc | tac | ctg | aac | gcc | ctc | gag | atc | tgg | aag | aag | gac | ccg | 384 |
| Ser | Leu | Asn | Leu | Tyr | Leu | Asn | Ala | Leu | Glu | Ile | Trp | Lys | Lys | Asp | Pro | |
| | | | 115 | | | | | 120 | | | | | 125 | | | |
| aac | aac | ctg | act | act | atc | gag | aac | gtg | act | gac | tac | ttc | cgg | tca | ctc | 432 |
| Asn | Asn | Leu | Thr | Thr | Ile | Glu | Asn | Val | Thr | Asp | Tyr | Phe | Arg | Ser | Leu | |
| | 130 | | | | | 135 | | | | | 140 | | | | | |
| aac | gtc | gtg | ttc | acg | cac | gac | atg | ccc | tcg | ttc | gcc | gtc | cct | gga | tac | 480 |
| Asn | Val | Val | Phe | Thr | His | Asp | Met | Pro | Ser | Phe | Ala | Val | Pro | Gly | Tyr | |
| 145 | | | | | 150 | | | | | 155 | | | | | 160 | |
| gag | acc | aag | ctg | ctc | acc | atc | tac | gcc | cag | gct | gca | aac | ctc | cat | ctg | 528 |
| Glu | Thr | Lys | Leu | Leu | Thr | Ile | Tyr | Ala | Gln | Ala | Ala | Asn | Leu | His | Leu | |
| | | | | 165 | | | | | 170 | | | | | 175 | | |
| ctg | ttg | ctc | agg | gac | gca | tca | cgt | ttc | ggt | gag | gga | tgg | ggt | ttg | acc | 576 |
| Leu | Leu | Leu | Arg | Asp | Ala | Ser | Arg | Phe | Gly | Glu | Gly | Trp | Gly | Leu | Thr | |
| | | | 180 | | | | | 185 | | | | | 190 | | | |
| cag | gag | atc | atc | aac | acg | aac | tac | aac | gac | cag | ctc | cgc | ctc | acc | gcc | 624 |
| Gln | Glu | Ile | Ile | Asn | Thr | Asn | Tyr | Asn | Asp | Gln | Leu | Arg | Leu | Thr | Ala | |
| | | | 195 | | | | | 200 | | | | | 205 | | | |
| gaa | tac | acc | gac | cac | tgc | gtg | aag | tgg | tac | aac | gcc | ggc | ttg | gag | aag | 672 |
| Glu | Tyr | Thr | Asp | His | Cys | Val | Lys | Trp | Tyr | Asn | Ala | Gly | Leu | Glu | Lys | |
| | 210 | | | | | 215 | | | | | 220 | | | | | |
| ctg | aag | ggc | aac | ctc | acg | ggt | gag | aac | tgg | tac | acg | tac | aac | cgg | ttc | 720 |
| Leu | Lys | Gly | Asn | Leu | Thr | Gly | Glu | Asn | Trp | Tyr | Thr | Tyr | Asn | Arg | Phe | |
| 225 | | | | | 230 | | | | | 235 | | | | | 240 | |
| cgc | agg | gag | atg | acc | ctc | atg | gtg | ctg | gac | gtg | gtc | gca | ttg | ttc | cca | 768 |
| Arg | Arg | Glu | Met | Thr | Leu | Met | Val | Leu | Asp | Val | Val | Ala | Leu | Phe | Pro | |
| | | | | 245 | | | | | 250 | | | | | 255 | | |
| aac | tac | gac | acc | cgc | atg | tac | ccg | atc | ggg | aca | tca | agc | gag | ctt | acc | 816 |
| Asn | Tyr | Asp | Thr | Arg | Met | Tyr | Pro | Ile | Gly | Thr | Ser | Ser | Glu | Leu | Thr | |
| | | | 260 | | | | | 265 | | | | | 270 | | | |
| cgt | atg | atc | tac | act | gac | ccc | atc | gcc | tac | acc | cag | tcc | gac | cca | tgg | 864 |
| Arg | Met | Ile | Tyr | Thr | Asp | Pro | Ile | Ala | Tyr | Thr | Gln | Ser | Asp | Pro | Trp | |
| | | | 275 | | | | | 280 | | | | | 285 | | | |
| tac | aag | atc | acg | tcc | ctg | agc | ttc | tcg | aac | atc | gag | aac | agc | gcg | atc | 912 |
| Tyr | Lys | Ile | Thr | Ser | Leu | Ser | Phe | Ser | Asn | Ile | Glu | Asn | Ser | Ala | Ile | |
| | 290 | | | | | 295 | | | | | 300 | | | | | |
| ccc | tcc | cca | tcg | ttc | ttc | cgc | tgg | ctc | aag | tcc | gtc | agc | att | aac | tcc | 960 |
| Pro | Ser | Pro | Ser | Phe | Phe | Arg | Trp | Leu | Lys | Ser | Val | Ser | Ile | Asn | Ser | |
| 305 | | | | | 310 | | | | | 315 | | | | | 320 | |
| cag | tgg | tgg | ggt | tcc | gga | cct | tca | caa | acc | tac | tac | tgg | gtg | ggg | cac | 1008 |
| Gln | Trp | Trp | Gly | Ser | Gly | Pro | Ser | Gln | Thr | Tyr | Tyr | Trp | Val | Gly | His | |
| | | | | 325 | | | | | 330 | | | | | 335 | | |
| gaa | ctg | gtc | tac | agc | aac | agc | aac | agc | aac | cag | tcg | ctg | aag | gtg | aag | 1056 |
| Glu | Leu | Val | Tyr | Ser | Asn | Ser | Asn | Ser | Asn | Gln | Ser | Leu | Lys | Val | Lys | |
| | | | | 340 | | | | | 345 | | | | | 350 | | |
| tac | ggc | gac | cct | aac | agc | ttc | atc | gag | ccc | ccg | gat | tcc | ttc | tcc | ttc | 1104 |
| Tyr | Gly | Asp | Pro | Asn | Ser | Phe | Ile | Glu | Pro | Pro | Asp | Ser | Phe | Ser | Phe | |
| | | | 355 | | | | | 360 | | | | | 365 | | | |
| agc | agc | acg | gac | gtg | tac | agg | acc | atc | tca | gtc | gtg | cgt | aat | tcc | gtg | 1152 |
| Ser | Ser | Thr | Asp | Val | Tyr | Arg | Thr | Ile | Ser | Val | Val | Arg | Asn | Ser | Val | |
| | | 370 | | | | | 375 | | | | | 380 | | | | |
| tcg | aac | tac | atc | gtg | tcg | gag | gtg | cgg | ttc | aac | agc | atc | tcc | tcc | acc | 1200 |
| Ser | Asn | Tyr | Ile | Val | Ser | Glu | Val | Arg | Phe | Asn | Ser | Ile | Ser | Ser | Thr | |

```
                                      -continued
385                 390                 395                 400
aac cag atc agc gag gaa atc tac aag cac cag tct aac tgg agc cgg      1248
Asn Gln Ile Ser Glu Glu Ile Tyr Lys His Gln Ser Asn Trp Ser Arg
                405                 410                 415 cag gag aca aag gac tca atc acc gag ctg agc ctg gcc gcc aac ccg      1296
Gln Glu Thr Lys Asp Ser Ile Thr Glu Leu Ser Leu Ala Ala Asn Pro
            420                 425                 430 cca acc acg ttc gga aac gtt gcc gag tac agt cac cgc ctg gct tac      1344
Pro Thr Thr Phe Gly Asn Val Ala Glu Tyr Ser His Arg Leu Ala Tyr
        435                 440                 445 atc tca gag gcg tac cag tct cac aac cca tct aag tac ccg acc tat      1392
Ile Ser Glu Ala Tyr Gln Ser His Asn Pro Ser Lys Tyr Pro Thr Tyr
    450                 455                 460 atc ccc gtg ttc ggg tgg acc cac aca tcc gtg agg tac gac aac aag      1440
Ile Pro Val Phe Gly Trp Thr His Thr Ser Val Arg Tyr Asp Asn Lys
465                 470                 475                 480 att ttc ccg gac aag atc acg cag atc ccc gcg gtt aag agt agc tca      1488
Ile Phe Pro Asp Lys Ile Thr Gln Ile Pro Ala Val Lys Ser Ser Ser
                485                 490                 495 gct cag ggg gga agc tgg aag aat atc gtc aag ggg ccc gga ttc acg      1536
Ala Gln Gly Gly Ser Trp Lys Asn Ile Val Lys Gly Pro Gly Phe Thr
            500                 505                 510 ggt gga gac gtg acg acg gcg gtt tca cct gca act gtt acg gat att      1584
Gly Gly Asp Val Thr Thr Ala Val Ser Pro Ala Thr Val Thr Asp Ile
        515                 520                 525 atc aag atc cag gtt acc ctt gat ccc aac agt ctg agc cag aag tat      1632
Ile Lys Ile Gln Val Thr Leu Asp Pro Asn Ser Leu Ser Gln Lys Tyr
    530                 535                 540 cgg gca cgc ctt cgc tac gcc agc aac gcc ttc gtc ccg gca acc ctt      1680
Arg Ala Arg Leu Arg Tyr Ala Ser Asn Ala Phe Val Pro Ala Thr Leu
545                 550                 555                 560 tat acg aac acc tcg tca aac tac aac ttc gaa ctg aag aag ggc acg      1728
Tyr Thr Asn Thr Ser Ser Asn Tyr Asn Phe Glu Leu Lys Lys Gly Thr
                565                 570                 575 act gag cag ttc acg acc tac aac agc tac cag tac gtg gac atc ccc      1776
Thr Glu Gln Phe Thr Thr Tyr Asn Ser Tyr Gln Tyr Val Asp Ile Pro
            580                 585                 590 ggc agc atc cag ttc aac aat acg tcc gac acc gtg tcg gtc tac ctg      1824
Gly Ser Ile Gln Phe Asn Asn Thr Ser Asp Thr Val Ser Val Tyr Leu
        595                 600                 605 cac atg gac tca acc tcg aac gtg aac gtg cac gtg gac cgg atc gag      1872
His Met Asp Ser Thr Ser Asn Val Asn Val His Val Asp Arg Ile Glu
    610                 615                 620 ttc atc ccg atc gac tga                                              1890
Phe Ile Pro Ile Asp *
625

<210> SEQ ID NO 15
<211> LENGTH: 629
<212> TYPE: PRT
<213> ORGANISM: Artificial Sequence
<220> FEATURE:
<223> OTHER INFORMATION: synAXMI-028

<400> SEQUENCE: 15

Met Asn Gln Lys Asn Tyr Glu Ile Ile Gly Ala Ser Thr Asn Gly Thr
1               5                   10                  15

Ile Glu Leu Pro Glu Asp Tyr Asn Thr Ile Val Ser Pro Tyr Asp Ala
            20                  25                  30

Pro Ala Ser Val Thr Thr Thr Ile Glu Ile Thr Gly Thr Ile Leu Ser
```

-continued

```
                35                  40                  45
Asp Leu Gly Val Pro Gly Ala Ser Ser Val Ser Leu Leu Asn Lys
 50                  55                  60
Leu Ile Asn Leu Leu Trp Pro Asn Asp Thr Asn Thr Val Trp Gly Thr
 65                  70                  75                  80
Phe Gly Lys Glu Thr Ala Asp Leu Leu Asn Glu Val Leu Ser Pro Asp
                 85                  90                  95
Asp Pro Val Val Lys Asp Ala Asn Thr Ile Leu Lys Gly Ile Asn Gly
                100                 105                 110
Ser Leu Asn Leu Tyr Leu Asn Ala Leu Glu Ile Trp Lys Lys Asp Pro
                115                 120                 125
Asn Asn Leu Thr Thr Ile Glu Asn Val Thr Asp Tyr Phe Arg Ser Leu
130                 135                 140
Asn Val Val Phe Thr His Asp Met Pro Ser Phe Ala Val Pro Gly Tyr
145                 150                 155                 160
Glu Thr Lys Leu Leu Thr Ile Tyr Ala Gln Ala Ala Asn Leu His Leu
                165                 170                 175
Leu Leu Leu Arg Asp Ala Ser Arg Phe Gly Glu Gly Trp Gly Leu Thr
                180                 185                 190
Gln Glu Ile Ile Asn Thr Asn Tyr Asn Asp Gln Leu Arg Leu Thr Ala
                195                 200                 205
Glu Tyr Thr Asp His Cys Val Lys Trp Tyr Asn Ala Gly Leu Glu Lys
                210                 215                 220
Leu Lys Gly Asn Leu Thr Gly Glu Asn Trp Tyr Thr Tyr Asn Arg Phe
225                 230                 235                 240
Arg Arg Glu Met Thr Leu Met Val Leu Asp Val Val Ala Leu Phe Pro
                245                 250                 255
Asn Tyr Asp Thr Arg Met Tyr Pro Ile Gly Thr Ser Ser Glu Leu Thr
                260                 265                 270
Arg Met Ile Tyr Thr Asp Pro Ile Ala Tyr Thr Gln Ser Asp Pro Trp
                275                 280                 285
Tyr Lys Ile Thr Ser Leu Ser Phe Ser Asn Ile Glu Asn Ser Ala Ile
                290                 295                 300
Pro Ser Pro Ser Phe Phe Arg Trp Leu Lys Ser Val Ser Ile Asn Ser
305                 310                 315                 320
Gln Trp Trp Gly Ser Gly Pro Ser Gln Thr Tyr Tyr Trp Val Gly His
                325                 330                 335
Glu Leu Val Tyr Ser Asn Ser Asn Ser Asn Gln Ser Leu Lys Val Lys
                340                 345                 350
Tyr Gly Asp Pro Asn Ser Phe Ile Glu Pro Pro Asp Ser Phe Ser Phe
                355                 360                 365
Ser Ser Thr Asp Val Tyr Arg Thr Ile Ser Val Val Arg Asn Ser Val
370                 375                 380
Ser Asn Tyr Ile Val Ser Glu Val Arg Phe Asn Ser Ile Ser Ser Thr
385                 390                 395                 400
Asn Gln Ile Ser Glu Glu Ile Tyr Lys His Gln Ser Asn Trp Ser Arg
                405                 410                 415
Gln Glu Thr Lys Asp Ser Ile Thr Glu Leu Ser Leu Ala Ala Asn Pro
                420                 425                 430
Pro Thr Thr Phe Gly Asn Val Ala Glu Tyr Ser His Arg Leu Ala Tyr
                435                 440                 445
Ile Ser Glu Ala Tyr Gln Ser His Asn Pro Ser Lys Tyr Pro Thr Tyr
450                 455                 460
```

```
Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
            485                 490                 495

Ala Gln Gly Gly Ser Trp Lys Asn Ile Val Lys Gly Pro Gly Phe Thr
        500                 505                 510

Gly Gly Asp Val Thr Thr Ala Val Ser Pro Ala Thr Val Thr Asp Ile
        515                 520                 525

Ile Lys Ile Gln Val Thr Leu Asp Pro Asn Ser Leu Ser Gln Lys Tyr
    530                 535                 540

Arg Ala Arg Leu Arg Tyr Ala Ser Asn Ala Phe Val Pro Ala Thr Leu
545                 550                 555                 560

Tyr Thr Asn Thr Ser Ser Asn Tyr Asn Phe Glu Leu Lys Lys Gly Thr
                565                 570                 575

Thr Glu Gln Phe Thr Thr Tyr Asn Ser Tyr Gln Tyr Val Asp Ile Pro
            580                 585                 590

Gly Ser Ile Gln Phe Asn Asn Thr Ser Asp Thr Val Ser Val Tyr Leu
        595                 600                 605

His Met Asp Ser Thr Ser Asn Val Asn Val His Val Asp Arg Ile Glu
    610                 615                 620

Phe Ile Pro Ile Asp
625

<210> SEQ ID NO 16
<211> LENGTH: 2010
<212> TYPE: DNA
<213> ORGANISM: Artificial Sequence
<220> FEATURE:
<223> OTHER INFORMATION: synaxmi-029
<221> NAME/KEY: CDS
<222> LOCATION: (1)...(2010)

<400> SEQUENCE: 16 atg aac tgc ggc gat cat aac gag ttc gat atc atc gat gtc atc gag     48
Met Asn Cys Gly Asp His Asn Glu Phe Asp Ile Ile Asp Val Ile Glu
1               5                   10                  15 aac aac cag acc aag gcc tcc cgc cat gtc aac gag tca gat aac gtc     96
Asn Asn Gln Thr Lys Ala Ser Arg His Val Asn Glu Ser Asp Asn Val
            20                  25                  30 aac cgc cag cgc aac ctg agc aac acc atc ttc agc aac ctc agc tcc    144
Asn Arg Gln Arg Asn Leu Ser Asn Thr Ile Phe Ser Asn Leu Ser Ser
        35                  40                  45 aac tac ccc ctg gcc agc aac ccc aac acc ccc ttc cag aac atg aac    192
Asn Tyr Pro Leu Ala Ser Asn Pro Asn Thr Pro Phe Gln Asn Met Asn
    50                  55                  60 tac aag gag tac ctc aac atc acc gag ggc ggc atc atc aac ccc acc    240
Tyr Lys Glu Tyr Leu Asn Ile Thr Glu Gly Gly Ile Ile Asn Pro Thr
65                  70                  75                  80 ctc gcc ggc tct gct atc gtc gtc gct cag aac gtc tct aag acc atc    288
Leu Ala Gly Ser Ala Ile Val Val Ala Gln Asn Val Ser Lys Thr Ile
                85                  90                  95 ctc aag aag ctg ggc tca acc atc ctg ggc aag atc ctc ggc tct gtc    336
Leu Lys Lys Leu Gly Ser Thr Ile Leu Gly Lys Ile Leu Gly Ser Val
            100                 105                 110 ctg gat atc ctc tgg cct acc aac acc gag gaa atc tgg ctg gag ctg    384
Leu Asp Ile Leu Trp Pro Thr Asn Thr Glu Glu Ile Trp Leu Glu Leu
        115                 120                 125 atc gat gag gtc gag gag ctg atc aac cag aag atc gag cag cag gtc    432
```

```
                Ile Asp Glu Val Glu Leu Ile Asn Gln Lys Ile Glu Gln Gln Val
                    130                 135                 140 atc atc gat gcc gag acc gcc ctg gag tca gtc aag ctg aac gtc gat       480
Ile Ile Asp Ala Glu Thr Ala Leu Glu Ser Val Lys Leu Asn Val Asp
145                 150                 155                 160 ctc tac ctc aac gcc ttc gaa gag tgg gag aag cgc cct acc aac gag       528
Leu Tyr Leu Asn Ala Phe Glu Glu Trp Glu Lys Arg Pro Thr Asn Glu
                165                 170                 175 tac tca acc gag ctc gtc tac aag cgc ttc acc gat gcc tac aac tac       576
Tyr Ser Thr Glu Leu Val Tyr Lys Arg Phe Thr Asp Ala Tyr Asn Tyr
            180                 185                 190 gcc cgc act tcc atc ccc ttc ttc cgc gtt aag acc tac gag gtc agc       624
Ala Arg Thr Ser Ile Pro Phe Phe Arg Val Lys Thr Tyr Glu Val Ser
        195                 200                 205 ctg ctg tct gtc tac gct cag gct gct aac atc agc ctc ctc ctg agc       672
Leu Leu Ser Val Tyr Ala Gln Ala Ala Asn Ile Ser Leu Leu Leu Ser
    210                 215                 220 agg gat gct cag att tac ggc gat ctg tgg ggt ttc gat gag cat gat       720
Arg Asp Ala Gln Ile Tyr Gly Asp Leu Trp Gly Phe Asp Glu His Asp
225                 230                 235                 240 aag gcc acc ttc gat tca gag cgc aag ctg ttc cgc gcc gag tac atc       768
Lys Ala Thr Phe Asp Ser Glu Arg Lys Leu Phe Arg Ala Glu Tyr Ile
                245                 250                 255 gat cat tgc acc aag tac tac aag gtc ggc ctc gat cgc ctg aag ggc       816
Asp His Cys Thr Lys Tyr Tyr Lys Val Gly Leu Asp Arg Leu Lys Gly
            260                 265                 270 tcc tcc tac ggc tcc tgg gtc aac tac aac cgc tac cgc cgc gag atg       864
Ser Ser Tyr Gly Ser Trp Val Asn Tyr Asn Arg Tyr Arg Arg Glu Met
        275                 280                 285 acc ctc atg atc ctg gat acc atc gcc gcc ttc cct tac tac gat atc       912
Thr Leu Met Ile Leu Asp Thr Ile Ala Ala Phe Pro Tyr Tyr Asp Ile
    290                 295                 300 gag gag tac ccc atc gag gtc tct acc cag ctc gcc agg gag gtt tac       960
Glu Glu Tyr Pro Ile Glu Val Ser Thr Gln Leu Ala Arg Glu Val Tyr
305                 310                 315                 320 acc gat ccc atc atc acc tca ttc gtc gag agc gat cat ggc ccc agc      1008
Thr Asp Pro Ile Ile Thr Ser Phe Val Glu Ser Asp His Gly Pro Ser
                325                 330                 335 ttc tcc ttc atg gag agc aac gcc atc cgc aag cct cat ctg gtc gat      1056
Phe Ser Phe Met Glu Ser Asn Ala Ile Arg Lys Pro His Leu Val Asp
            340                 345                 350 tac ctg gat aac ctg tac atc tac acc agc cgc ttc cgc acc ttc tcc      1104
Tyr Leu Asp Asn Leu Tyr Ile Tyr Thr Ser Arg Phe Arg Thr Phe Ser
        355                 360                 365 aac gag ttc cag ccc gat ctg aac tac tgg gcc gcc cat aag gtc aag      1152
Asn Glu Phe Gln Pro Asp Leu Asn Tyr Trp Ala Ala His Lys Val Lys
    370                 375                 380 tac aag tac tca ggc gat ccc acc ctg cat gag acc ccc atc tac ggc      1200
Tyr Lys Tyr Ser Gly Asp Pro Thr Leu His Glu Thr Pro Ile Tyr Gly
385                 390                 395                 400 aac gcc tcc aac tac gag agc acc ggc aac tac agc ttc cgc ggc aac      1248
Asn Ala Ser Asn Tyr Glu Ser Thr Gly Asn Tyr Ser Phe Arg Gly Asn
                405                 410                 415 tcc atc tac cag acc ctg agc gcc cct agc gct atc ctc acc cct aac      1296
Ser Ile Tyr Gln Thr Leu Ser Ala Pro Ser Ala Ile Leu Thr Pro Asn
            420                 425                 430 tac atc tac tac ggc atc gag cag gtc gag ttc tac ggc aac aag ggc      1344
Tyr Ile Tyr Tyr Gly Ile Glu Gln Val Glu Phe Tyr Gly Asn Lys Gly
        435                 440                 445
```

```
aac gtc tac tac cgc ggc ggc aac aag tac ccc ctg tca gtc gat tcc      1392
Asn Val Tyr Tyr Arg Gly Gly Asn Lys Tyr Pro Leu Ser Val Asp Ser
    450                 455                 460 gcc aac cag ctg cct cct gat gtc gag cct atc acc gag aac tac aac      1440
Ala Asn Gln Leu Pro Pro Asp Val Glu Pro Ile Thr Glu Asn Tyr Asn
465                 470                 475                 480 cat gtc ctg tgc cat gcc acc gcc gtc cct gtt aag gat ggc ggc acc      1488
His Val Leu Cys His Ala Thr Ala Val Pro Val Lys Asp Gly Gly Thr
                485                 490                 495 gtc cct atc ttc agc tgg acc cat cgc tct gct gat tac tac aac acc      1536
Val Pro Ile Phe Ser Trp Thr His Arg Ser Ala Asp Tyr Tyr Asn Thr
            500                 505                 510 atc tac ccc gat aag atc acc cag ctc ccc gcc gtc aag tcc acc ccc      1584
Ile Tyr Pro Asp Lys Ile Thr Gln Leu Pro Ala Val Lys Ser Thr Pro
        515                 520                 525 tca cct gag gtc gag ggt ttg aag gtc cag gag ggt cct ggt ttc act      1632
Ser Pro Glu Val Glu Gly Leu Lys Val Gln Glu Gly Pro Gly Phe Thr
    530                 535                 540 ggt ggt gat ctg gtc gtc gct aag tcc agc aac cag acc atc gtc cgt      1680
Gly Gly Asp Leu Val Val Ala Lys Ser Ser Asn Gln Thr Ile Val Arg
545                 550                 555                 560 ctc aag gtc acc gtc gat agc cct ggc acc cag aag tac cgc atc agg      1728
Leu Lys Val Thr Val Asp Ser Pro Gly Thr Gln Lys Tyr Arg Ile Arg
                565                 570                 575 ctc aag tac gcc gct act tcc aac ttc tac ctc ggc gcc tac gct ggt      1776
Leu Lys Tyr Ala Ala Thr Ser Asn Phe Tyr Leu Gly Ala Tyr Ala Gly
            580                 585                 590 tcc aac ggt ggt aac ggt atc ccc ggt atc tca acc gtt cct aag acc      1824
Ser Asn Gly Gly Asn Gly Ile Pro Gly Ile Ser Thr Val Pro Lys Thr
        595                 600                 605 atg aac atc gag gac ccc ctg agc tac acc agc ttc gcc tac atc gat      1872
Met Asn Ile Glu Asp Pro Leu Ser Tyr Thr Ser Phe Ala Tyr Ile Asp
    610                 615                 620 ctc ccc gat agc tac acc ttc agc cag aag gat gag gtc atc cgc ttc      1920
Leu Pro Asp Ser Tyr Thr Phe Ser Gln Lys Asp Glu Val Ile Arg Phe
625                 630                 635                 640 acc atc aac atc tac gag agc ggc ggc gcc gtc tac gcc gat aag gtc      1968
Thr Ile Asn Ile Tyr Glu Ser Gly Gly Ala Val Tyr Ala Asp Lys Val
                645                 650                 655 gag ttc atc ccc gtc gat gcc gat tac gat gag ggc gtc tag              2010
Glu Phe Ile Pro Val Asp Ala Asp Tyr Asp Glu Gly Val *
            660                 665

<210> SEQ ID NO 17
<211> LENGTH: 669
<212> TYPE: PRT
<213> ORGANISM: Artificial Sequence
<220> FEATURE:
<223> OTHER INFORMATION: synAXMI-029

<400> SEQUENCE: 17

Met Asn Cys Gly Asp His Asn Glu Phe Asp Ile Ile Asp Val Ile Glu
 1               5                  10                  15

Asn Asn Gln Thr Lys Ala Ser Arg His Val Asn Glu Ser Asp Asn Val
            20                  25                  30

Asn Arg Gln Arg Asn Leu Ser Asn Thr Ile Phe Ser Asn Leu Ser Ser
        35                  40                  45

Asn Tyr Pro Leu Ala Ser Asn Pro Asn Thr Pro Phe Gln Asn Met Asn
    50                  55                  60

Tyr Lys Glu Tyr Leu Asn Ile Thr Glu Gly Gly Ile Ile Asn Pro Thr
```

-continued

```
                65                  70                  75                  80
Leu Ala Gly Ser Ala Ile Val Val Ala Gln Asn Val Ser Lys Thr Ile
                    85                  90                  95

Leu Lys Lys Leu Gly Ser Thr Ile Leu Gly Lys Ile Leu Gly Ser Val
                    100                 105                 110

Leu Asp Ile Leu Trp Pro Thr Asn Thr Glu Glu Ile Trp Leu Glu Leu
                    115                 120                 125

Ile Asp Glu Val Glu Glu Leu Ile Asn Gln Lys Ile Glu Gln Gln Val
                    130                 135                 140

Ile Ile Asp Ala Glu Thr Ala Leu Glu Ser Val Lys Leu Asn Val Asp
145                 150                 155                 160

Leu Tyr Leu Asn Ala Phe Glu Glu Trp Glu Lys Arg Pro Thr Asn Glu
                    165                 170                 175

Tyr Ser Thr Glu Leu Val Tyr Lys Arg Phe Thr Asp Ala Tyr Asn Tyr
                    180                 185                 190

Ala Arg Thr Ser Ile Pro Phe Phe Arg Val Lys Thr Tyr Glu Val Ser
                    195                 200                 205

Leu Leu Ser Val Tyr Ala Gln Ala Ala Asn Ile Ser Leu Leu Leu Ser
                    210                 215                 220

Arg Asp Ala Gln Ile Tyr Gly Asp Leu Trp Gly Phe Asp Glu His Asp
225                 230                 235                 240

Lys Ala Thr Phe Asp Ser Glu Arg Lys Leu Phe Arg Ala Glu Tyr Ile
                    245                 250                 255

Asp His Cys Thr Lys Tyr Tyr Lys Val Gly Leu Asp Arg Leu Lys Gly
                    260                 265                 270

Ser Ser Tyr Gly Ser Trp Val Asn Tyr Asn Arg Tyr Arg Arg Glu Met
                    275                 280                 285

Thr Leu Met Ile Leu Asp Thr Ile Ala Ala Phe Pro Tyr Tyr Asp Ile
                    290                 295                 300

Glu Glu Tyr Pro Ile Glu Val Ser Thr Gln Leu Ala Arg Glu Val Tyr
305                 310                 315                 320

Thr Asp Pro Ile Ile Thr Ser Phe Val Glu Ser Asp His Gly Pro Ser
                    325                 330                 335

Phe Ser Phe Met Glu Ser Asn Ala Ile Arg Lys Pro His Leu Val Asp
                    340                 345                 350

Tyr Leu Asp Asn Leu Tyr Ile Tyr Thr Ser Arg Phe Arg Thr Phe Ser
                    355                 360                 365

Asn Glu Phe Gln Pro Asp Leu Asn Tyr Trp Ala Ala His Lys Val Lys
                    370                 375                 380

Tyr Lys Tyr Ser Gly Asp Pro Thr Leu His Glu Thr Pro Ile Tyr Gly
385                 390                 395                 400

Asn Ala Ser Asn Tyr Glu Ser Thr Gly Asn Tyr Ser Phe Arg Gly Asn
                    405                 410                 415

Ser Ile Tyr Gln Thr Leu Ser Ala Pro Ser Ala Ile Leu Thr Pro Asn
                    420                 425                 430

Tyr Ile Tyr Tyr Gly Ile Glu Gln Val Glu Phe Tyr Gly Asn Lys Gly
                    435                 440                 445

Asn Val Tyr Tyr Arg Gly Gly Asn Lys Tyr Pro Leu Ser Val Asp Ser
450                 455                 460

Ala Asn Gln Leu Pro Pro Asp Val Glu Pro Ile Thr Glu Asn Tyr Asn
465                 470                 475                 480

His Val Leu Cys His Ala Thr Ala Val Pro Val Lys Asp Gly Gly Thr
                    485                 490                 495
```

```
Val Pro Ile Phe Ser Trp Thr His Arg Ser Ala Asp Tyr Tyr Asn Thr
            500                 505                 510

Ile Tyr Pro Asp Lys Ile Thr Gln Leu Pro Ala Val Lys Ser Thr Pro
        515                 520                 525

Ser Pro Glu Val Glu Gly Leu Lys Val Gln Glu Gly Pro Gly Phe Thr
    530                 535                 540

Gly Gly Asp Leu Val Val Ala Lys Ser Ser Asn Gln Thr Ile Val Arg
545                 550                 555                 560

Leu Lys Val Thr Val Asp Ser Pro Gly Thr Gln Lys Tyr Arg Ile Arg
                565                 570                 575

Leu Lys Tyr Ala Ala Thr Ser Asn Phe Tyr Leu Gly Ala Tyr Ala Gly
            580                 585                 590

Ser Asn Gly Gly Asn Gly Ile Pro Gly Ile Ser Thr Val Pro Lys Thr
        595                 600                 605

Met Asn Ile Glu Asp Pro Leu Ser Tyr Thr Ser Phe Ala Tyr Ile Asp
    610                 615                 620

Leu Pro Asp Ser Tyr Thr Phe Ser Gln Lys Asp Glu Val Ile Arg Phe
625                 630                 635                 640

Thr Ile Asn Ile Tyr Glu Ser Gly Gly Ala Val Tyr Ala Asp Lys Val
                645                 650                 655

Glu Phe Ile Pro Val Asp Ala Asp Tyr Asp Glu Gly Val
            660                 665

<210> SEQ ID NO 18
<211> LENGTH: 2115
<212> TYPE: DNA
<213> ORGANISM: Artificial Sequence
<220> FEATURE:
<223> OTHER INFORMATION: axmi-029ER
<221> NAME/KEY: CDS
<222> LOCATION: (1)...(2115)

<400> SEQUENCE: 18 atg ggt tac agc tcc ttc gtc gcc atc gct ctc ctc atg tcc gtc gtc     48
Met Gly Tyr Ser Ser Phe Val Ala Ile Ala Leu Leu Met Ser Val Val
 1               5                  10                  15 gtc gtt tgc aac ggc ggt aag acc agc act tac gtc agg aac ctg atg     96
Val Val Cys Asn Gly Gly Lys Thr Ser Thr Tyr Val Arg Asn Leu Met
            20                  25                  30 aac tgc ggc gat cat aac gag ttc gat atc atc gat gtc atc gag aac    144
Asn Cys Gly Asp His Asn Glu Phe Asp Ile Ile Asp Val Ile Glu Asn
        35                  40                  45 aac cag acc aag gcc tcc cgc cat gtc aac gag tca gat aac gtc aac    192
Asn Gln Thr Lys Ala Ser Arg His Val Asn Glu Ser Asp Asn Val Asn
    50                  55                  60 cgc cag cgc aac ctg agc aac acc atc ttc agc aac ctc agc tcc aac    240
Arg Gln Arg Asn Leu Ser Asn Thr Ile Phe Ser Asn Leu Ser Ser Asn
65                  70                  75                  80 tac ccc ctg gcc agc aac ccc aac acc ccc ttc cag aac atg aac tac    288
Tyr Pro Leu Ala Ser Asn Pro Asn Thr Pro Phe Gln Asn Met Asn Tyr
                85                  90                  95 aag gag tac ctc aac atc acc gag ggc ggc atc atc aac ccc acc ctc    336
Lys Glu Tyr Leu Asn Ile Thr Glu Gly Gly Ile Ile Asn Pro Thr Leu
            100                 105                 110 gcc ggc tct gct atc gtc gtc gct cag aac gtc tct aag acc atc ctc    384
Ala Gly Ser Ala Ile Val Val Ala Gln Asn Val Ser Lys Thr Ile Leu
        115                 120                 125 aag aag ctg ggc tca acc atc ctg ggc aag atc ctc ggc tct gtc ctg    432
```

```
                Lys Lys Leu Gly Ser Thr Ile Leu Gly Lys Ile Leu Gly Ser Val Leu
                130                 135                 140 gat atc ctc tgg cct acc aac acc gag gaa atc tgg ctg gag ctg atc                    480
Asp Ile Leu Trp Pro Thr Asn Thr Glu Glu Ile Trp Leu Glu Leu Ile
145                 150                 155                 160 gat gag gtc gag gag ctg atc aac cag aag atc gag cag cag gtc atc                    528
Asp Glu Val Glu Glu Leu Ile Asn Gln Lys Ile Glu Gln Gln Val Ile
                165                 170                 175 atc gat gcc gag acc gcc ctg gag tca gtc aag ctg aac gtc gat ctc                    576
Ile Asp Ala Glu Thr Ala Leu Glu Ser Val Lys Leu Asn Val Asp Leu
            180                 185                 190 tac ctc aac gcc ttc gaa gag tgg gag aag cgc cct acc aac gag tac                    624
Tyr Leu Asn Ala Phe Glu Glu Trp Glu Lys Arg Pro Thr Asn Glu Tyr
        195                 200                 205 tca acc gag ctc gtc tac aag cgc ttc acc gat gcc tac aac tac gcc                    672
Ser Thr Glu Leu Val Tyr Lys Arg Phe Thr Asp Ala Tyr Asn Tyr Ala
    210                 215                 220 cgc act tcc atc ccc ttc ttc cgc gtt aag acc tac gag gtc agc ctg                    720
Arg Thr Ser Ile Pro Phe Phe Arg Val Lys Thr Tyr Glu Val Ser Leu
225                 230                 235                 240 ctg tct gtc tac gct cag gct gct aac atc agc ctg ctc ctg agc agg                    768
Leu Ser Val Tyr Ala Gln Ala Ala Asn Ile Ser Leu Leu Leu Ser Arg
                245                 250                 255 gat gct cag att tac ggc gat ctg tgg ggt ttc gat gag cat gat aag                    816
Asp Ala Gln Ile Tyr Gly Asp Leu Trp Gly Phe Asp Glu His Asp Lys
            260                 265                 270 gcc acc ttc gat tca gag cgc aag ctg ttc cgc gcc gag tac atc gat                    864
Ala Thr Phe Asp Ser Glu Arg Lys Leu Phe Arg Ala Glu Tyr Ile Asp
        275                 280                 285 cat tgc acc aag tac tac aag gtc ggc ctc gat cgc ctg aag ggc tcc                    912
His Cys Thr Lys Tyr Tyr Lys Val Gly Leu Asp Arg Leu Lys Gly Ser
    290                 295                 300 tcc tac ggc tcc tgg gtc aac tac aac cgc tac cgc cgc gag atg acc                    960
Ser Tyr Gly Ser Trp Val Asn Tyr Asn Arg Tyr Arg Arg Glu Met Thr
305                 310                 315                 320 ctc atg atc ctg gat acc atc gcc gcc ttc cct tac tac gat atc gag                   1008
Leu Met Ile Leu Asp Thr Ile Ala Ala Phe Pro Tyr Tyr Asp Ile Glu
                325                 330                 335 gag tac ccc atc gag gtc tct acc cag ctc gcc agg gag gtt tac acc                   1056
Glu Tyr Pro Ile Glu Val Ser Thr Gln Leu Ala Arg Glu Val Tyr Thr
            340                 345                 350 gat ccc atc atc acc tca ttc gtc gag agc gat cat ggc ccc agc ttc                   1104
Asp Pro Ile Ile Thr Ser Phe Val Glu Ser Asp His Gly Pro Ser Phe
        355                 360                 365 tcc ttc atg gag agc aac gcc atc cgc aag cct cat ctg gtc gat tac                   1152
Ser Phe Met Glu Ser Asn Ala Ile Arg Lys Pro His Leu Val Asp Tyr
    370                 375                 380 ctg gat aac ctg tac atc tac acc agc cgc ttc cgc acc ttc tcc aac                   1200
Leu Asp Asn Leu Tyr Ile Tyr Thr Ser Arg Phe Arg Thr Phe Ser Asn
385                 390                 395                 400 gag ttc cag ccc gat ctg aac tac tgg gcc gcc cat aag gtc aag tac                   1248
Glu Phe Gln Pro Asp Leu Asn Tyr Trp Ala Ala His Lys Val Lys Tyr
                405                 410                 415 aag tac tca ggc gat ccc acc ctg cat gag acc ccc atc tac ggc aac                   1296
Lys Tyr Ser Gly Asp Pro Thr Leu His Glu Thr Pro Ile Tyr Gly Asn
            420                 425                 430 gcc tcc aac tac gag agc acc ggc aac tac agc ttc cgc ggc aac tcc                   1344
Ala Ser Asn Tyr Glu Ser Thr Gly Asn Tyr Ser Phe Arg Gly Asn Ser
        435                 440                 445
```

```
atc tac cag acc ctg agc gcc cct agc gct atc ctc acc cct aac tac    1392
Ile Tyr Gln Thr Leu Ser Ala Pro Ser Ala Ile Leu Thr Pro Asn Tyr
450             455                 460 atc tac tac ggc atc gag cag gtc gag ttc tac ggc aac aag ggc aac    1440
Ile Tyr Tyr Gly Ile Glu Gln Val Glu Phe Tyr Gly Asn Lys Gly Asn
465                 470                 475                 480 gtc tac tac cgc ggc ggc aac aag tac ccc ctg tca gtc gat tcc gcc    1488
Val Tyr Tyr Arg Gly Gly Asn Lys Tyr Pro Leu Ser Val Asp Ser Ala
                485                 490                 495 aac cag ctg cct cct gat gtc gag cct atc acc gag aac tac aac cat    1536
Asn Gln Leu Pro Pro Asp Val Glu Pro Ile Thr Glu Asn Tyr Asn His
            500                 505                 510 gtc ctg tgc cat gcc acc gcc gtc cct gtt aag gat ggc ggc acc gtc    1584
Val Leu Cys His Ala Thr Ala Val Pro Val Lys Asp Gly Gly Thr Val
        515                 520                 525 cct atc ttc agc tgg acc cat cgc tct gct gat tac tac aac acc atc    1632
Pro Ile Phe Ser Trp Thr His Arg Ser Ala Asp Tyr Tyr Asn Thr Ile
    530                 535                 540 tac ccc gat aag atc acc cag ctc ccc gcc gtc aag tcc acc ccc tca    1680
Tyr Pro Asp Lys Ile Thr Gln Leu Pro Ala Val Lys Ser Thr Pro Ser
545                 550                 555                 560 cct gag gtc gag ggt ttg aag gtc cag gag ggt cct ggt ttc act ggt    1728
Pro Glu Val Glu Gly Leu Lys Val Gln Glu Gly Pro Gly Phe Thr Gly
                565                 570                 575 ggt gat ctg gtc gtc gct aag tcc agc aac cag acc atc gtc cgt ctc    1776
Gly Asp Leu Val Val Ala Lys Ser Ser Asn Gln Thr Ile Val Arg Leu
                580                 585                 590 aag gtc acc gtc gat agc cct ggc acc cag aag tac cgc atc agg ctc    1824
Lys Val Thr Val Asp Ser Pro Gly Thr Gln Lys Tyr Arg Ile Arg Leu
            595                 600                 605 aag tac gcc gct act tcc aac ttc tac ctc ggc gcc tac gct ggt tcc    1872
Lys Tyr Ala Ala Thr Ser Asn Phe Tyr Leu Gly Ala Tyr Ala Gly Ser
        610                 615                 620 aac ggt ggt aac ggt atc ccc ggt atc tca acc gtt cct aag acc atg    1920
Asn Gly Gly Asn Gly Ile Pro Gly Ile Ser Thr Val Pro Lys Thr Met
    625                 630                 635                 640 aac atc gag gac ccc ctg agc tac acc agc ttc gcc tac atc gat ctc    1968
Asn Ile Glu Asp Pro Leu Ser Tyr Thr Ser Phe Ala Tyr Ile Asp Leu
                645                 650                 655 ccc gat agc tac acc ttc agc cag aag gat gag gtc atc cgc ttc acc    2016
Pro Asp Ser Tyr Thr Phe Ser Gln Lys Asp Glu Val Ile Arg Phe Thr
                660                 665                 670 atc aac atc tac gag agc ggc ggc gcc gtc tac gcc gat aag gtc gag    2064
Ile Asn Ile Tyr Glu Ser Gly Gly Ala Val Tyr Ala Asp Lys Val Glu
            675                 680                 685 ttc atc ccc gtc gat gcc gat tac gat gag ggc gtc aag gat gag ctg    2112
Phe Ile Pro Val Asp Ala Asp Tyr Asp Glu Gly Val Lys Asp Glu Leu
        690                 695                 700 tag                                                                2115
*

<210> SEQ ID NO 19
<211> LENGTH: 704
<212> TYPE: PRT
<213> ORGANISM: Artificial Sequence
<220> FEATURE:
<223> OTHER INFORMATION: AXMI-029ER

<400> SEQUENCE: 19

Met Gly Tyr Ser Ser Phe Val Ala Ile Ala Leu Leu Met Ser Val Val
1               5                   10                  15
```

-continued

Val Val Cys Asn Gly Gly Lys Thr Ser Thr Tyr Val Arg Asn Leu Met
             20                  25                  30

Asn Cys Gly Asp His Asn Glu Phe Asp Ile Ile Asp Val Ile Glu Asn
             35                  40                  45

Asn Gln Thr Lys Ala Ser Arg His Val Asn Glu Ser Asp Asn Val Asn
             50                  55                  60

Arg Gln Arg Asn Leu Ser Asn Thr Ile Phe Ser Asn Leu Ser Ser Asn
 65                  70                  75                  80

Tyr Pro Leu Ala Ser Asn Pro Asn Thr Pro Phe Gln Asn Met Asn Tyr
                 85                  90                  95

Lys Glu Tyr Leu Asn Ile Thr Glu Gly Gly Ile Ile Asn Pro Thr Leu
                100                 105                 110

Ala Gly Ser Ala Ile Val Val Ala Gln Asn Val Ser Lys Thr Ile Leu
            115                 120                 125

Lys Lys Leu Gly Ser Thr Ile Leu Gly Lys Ile Leu Gly Ser Val Leu
            130                 135                 140

Asp Ile Leu Trp Pro Thr Asn Thr Glu Glu Ile Trp Leu Glu Leu Ile
145                 150                 155                 160

Asp Glu Val Glu Glu Leu Ile Asn Gln Lys Ile Glu Gln Val Ile
                165                 170                 175

Ile Asp Ala Glu Thr Ala Leu Glu Ser Val Lys Leu Asn Val Asp Leu
            180                 185                 190

Tyr Leu Asn Ala Phe Glu Glu Trp Glu Lys Arg Pro Thr Asn Glu Tyr
            195                 200                 205

Ser Thr Glu Leu Val Tyr Lys Arg Phe Thr Asp Ala Tyr Asn Tyr Ala
            210                 215                 220

Arg Thr Ser Ile Pro Phe Phe Arg Val Lys Thr Tyr Glu Val Ser Leu
225                 230                 235                 240

Leu Ser Val Tyr Ala Gln Ala Ala Asn Ile Ser Leu Leu Leu Ser Arg
                245                 250                 255

Asp Ala Gln Ile Tyr Gly Asp Leu Trp Gly Phe Asp Glu His Asp Lys
            260                 265                 270

Ala Thr Phe Asp Ser Glu Arg Lys Leu Phe Arg Ala Glu Tyr Ile Asp
            275                 280                 285

His Cys Thr Lys Tyr Tyr Lys Val Gly Leu Asp Arg Leu Lys Gly Ser
            290                 295                 300

Ser Tyr Gly Ser Trp Val Asn Tyr Asn Arg Tyr Arg Arg Glu Met Thr
305                 310                 315                 320

Leu Met Ile Leu Asp Thr Ile Ala Ala Phe Pro Tyr Tyr Asp Ile Glu
                325                 330                 335

Glu Tyr Pro Ile Glu Val Ser Thr Gln Leu Ala Arg Glu Val Tyr Thr
            340                 345                 350

Asp Pro Ile Ile Thr Ser Phe Val Glu Ser Asp His Gly Pro Ser Phe
            355                 360                 365

Ser Phe Met Glu Ser Asn Ala Ile Arg Lys Pro His Leu Val Asp Tyr
    370                 375                 380

Leu Asp Asn Leu Tyr Ile Tyr Thr Ser Arg Phe Arg Thr Phe Ser Asn
385                 390                 395                 400

Glu Phe Gln Pro Asp Leu Asn Tyr Trp Ala Ala His Lys Val Lys Tyr
                405                 410                 415

Lys Tyr Ser Gly Asp Pro Thr Leu His Glu Thr Pro Ile Tyr Gly Asn
            420                 425                 430

```
Ala Ser Asn Tyr Glu Ser Thr Gly Asn Tyr Ser Phe Arg Gly Asn Ser
        435                 440                 445

Ile Tyr Gln Thr Leu Ser Ala Pro Ser Ala Ile Leu Thr Pro Asn Tyr
450                 455                 460

Ile Tyr Tyr Gly Ile Glu Gln Val Glu Phe Tyr Gly Asn Lys Gly Asn
465                 470                 475                 480

Val Tyr Tyr Arg Gly Gly Asn Lys Tyr Pro Leu Ser Val Asp Ser Ala
                485                 490                 495

Asn Gln Leu Pro Pro Asp Val Glu Pro Ile Thr Glu Asn Tyr Asn His
            500                 505                 510

Val Leu Cys His Ala Thr Ala Val Pro Val Lys Asp Gly Gly Thr Val
        515                 520                 525

Pro Ile Phe Ser Trp Thr His Arg Ser Ala Asp Tyr Tyr Asn Thr Ile
    530                 535                 540

Tyr Pro Asp Lys Ile Thr Gln Leu Pro Ala Val Lys Ser Thr Pro Ser
545                 550                 555                 560

Pro Glu Val Glu Gly Leu Lys Val Gln Glu Gly Pro Gly Phe Thr Gly
                565                 570                 575

Gly Asp Leu Val Val Ala Lys Ser Ser Asn Gln Thr Ile Val Arg Leu
            580                 585                 590

Lys Val Thr Val Asp Ser Pro Gly Thr Gln Lys Tyr Arg Ile Arg Leu
        595                 600                 605

Lys Tyr Ala Ala Thr Ser Asn Phe Tyr Leu Gly Ala Tyr Ala Gly Ser
    610                 615                 620

Asn Gly Gly Asn Gly Ile Pro Gly Ile Ser Thr Val Pro Lys Thr Met
625                 630                 635                 640

Asn Ile Glu Asp Pro Leu Ser Tyr Thr Ser Phe Ala Tyr Ile Asp Leu
                645                 650                 655

Pro Asp Ser Tyr Thr Phe Ser Gln Lys Asp Glu Val Ile Arg Phe Thr
            660                 665                 670

Ile Asn Ile Tyr Glu Ser Gly Gly Ala Val Tyr Ala Asp Lys Val Glu
        675                 680                 685

Phe Ile Pro Val Asp Ala Asp Tyr Asp Glu Gly Val Lys Asp Glu Leu
    690                 695                 700

<210> SEQ ID NO 20
<211> LENGTH: 93
<212> TYPE: DNA
<213> ORGANISM: Lupinus albus
<220> FEATURE:
<221> NAME/KEY: misc_feature
<222> LOCATION: (0)...(0)
<223> OTHER INFORMATION: acid phosphatase leader sequence

<400> SEQUENCE: 20
atgggttaca gctccttcgt cgccatcgct ctcctcatgt ccgtcgtcgt cgtttgcaac    60
ggcggtaaga ccagcactta cgtcaggaac ctg                                 93

<210> SEQ ID NO 21
<211> LENGTH: 31
<212> TYPE: PRT
<213> ORGANISM: Lupinus albus
```

```
<400> SEQUENCE: 21

Met Gly Tyr Ser Ser Phe Val Ala Ile Ala Leu Leu Met Ser Val Val
 1               5                  10                  15

Val Val Cys Asn Gly Gly Lys Thr Ser Thr Tyr Val Arg Asn Leu
            20                  25                  30
```